United States Patent
Chen et al.

(10) Patent No.: US 9,944,682 B2
(45) Date of Patent: Apr. 17, 2018

(54) NANOBODY-FLOURESCENT PROTEIN FUSION

(71) Applicant: National University of Singapore, Singapore (SG)

(72) Inventors: Swaine Chen, Singapore (SG); Majid Eshaghi, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/117,147

(22) PCT Filed: Feb. 6, 2015

(86) PCT No.: PCT/SG2015/000033
§ 371 (c)(1),
(2) Date: Aug. 5, 2016

(87) PCT Pub. No.: WO2015/119576
PCT Pub. Date: Aug. 13, 2015

(65) Prior Publication Data
US 2017/0174732 A1    Jun. 22, 2017

Related U.S. Application Data

(60) Provisional application No. 61/965,782, filed on Feb. 7, 2014, provisional application No. 62/078,269, filed on Nov. 11, 2014.

(51) Int. Cl.
| | | |
|---|---|---|
| C07K 16/14 | (2006.01) | |
| C07K 14/435 | (2006.01) | |
| C07K 16/18 | (2006.01) | |
| G01N 33/533 | (2006.01) | |

(52) U.S. Cl.
CPC ........ *C07K 14/43595* (2013.01); *C07K 16/18* (2013.01); *G01N 33/533* (2013.01); *C07K 2317/569* (2013.01); *C07K 2319/60* (2013.01)

(58) Field of Classification Search
None
See application file for complete search history.

(56) References Cited

U.S. PATENT DOCUMENTS

2011/0159571 A1*  6/2011  Barry .................. C07K 16/2863
                                                        435/212
2014/0004037 A1*  1/2014  Wilton ................ C07K 16/2887
                                                        424/1.49

FOREIGN PATENT DOCUMENTS

WO    2012104791 A1    8/2012

OTHER PUBLICATIONS

Kirchhofer, et al., "Modulation of protein properties in living cells using nanobodies", Nature Structural & Molecular Biology, vol. 17, No. 1, Jan. 2010, 7 pages.
Kubala, et al., "Structural and thermodynamic analysis of the GFP:GFP-nanobody complex", Protein Science, vol. 19:2389-2401, Oct. 13, 2010, 13 pages.
Li, et al., "Cell-penetrating anti-GFAP VHH and corresponding flourescent fusion protein VHH-GFP spontaneously cross the blood-brain barrier and specifically recognize astrocytes: application to brain imaging", The FASEB Journal, vol. 26, No. 10, pp: 3969-3979, Oct. 2012, 12 pages.
PCT/SG2015/000033, "International Search Report and Written Opinion", dated Mar. 13, 2015, 11 pages.

* cited by examiner

*Primary Examiner* — James S Ketter
(74) *Attorney, Agent, or Firm* — Kilpatrick Townsend & Stockton LLP

(57) ABSTRACT

We describe the rational structure-based design of monomeric and dimeric forms of a nanobody-enhanced GFP (termed vsfGFP) that demonstrates ~1.3-fold higher brightness than sfGFP in a monomeric form and ~2.5-fold higher brightness in a dimeric form. These new vsfGFP variants demonstrate high stability and brightness in both bacterial and eukaryotic cells and are thus ideal for in vivo imaging applications. The combination of higher brightness, facile folding, stable expression, and tunable dimerization makes them ideal partners in essentially all in vitro applications already described for fluorescent proteins, including antibody fusion-based molecular probes, for which the higher brightness and tunable dimerization provide distinct advantages. Furthermore, the vsfGFP variants retain folding properties of sfGFP that enable bright fluorescence in oxidizing environments such as the bacterial periplasm. In particular, periplasmic expression enables the general construction of functional, fluorescent single domain antibody fusions, markedly enhancing the breadth and utility and reducing the cost of these molecular probes. Generalization of the vGFP strategy should provide similar improvements to other fluorescent proteins and may be extendable to higher order (and thus higher brightness) complexes.

23 Claims, 23 Drawing Sheets

Figure 1.
A
GFP            GFP-binding enhancer
B
GFP
Unenhanced
Brightness: 1
Long linker - monomer
Intramolecularly enhanced GFP
Brightness: 4
Short linker - dimer
Intermolecularly enhanced GFP
Brightness: 8

Figure 6
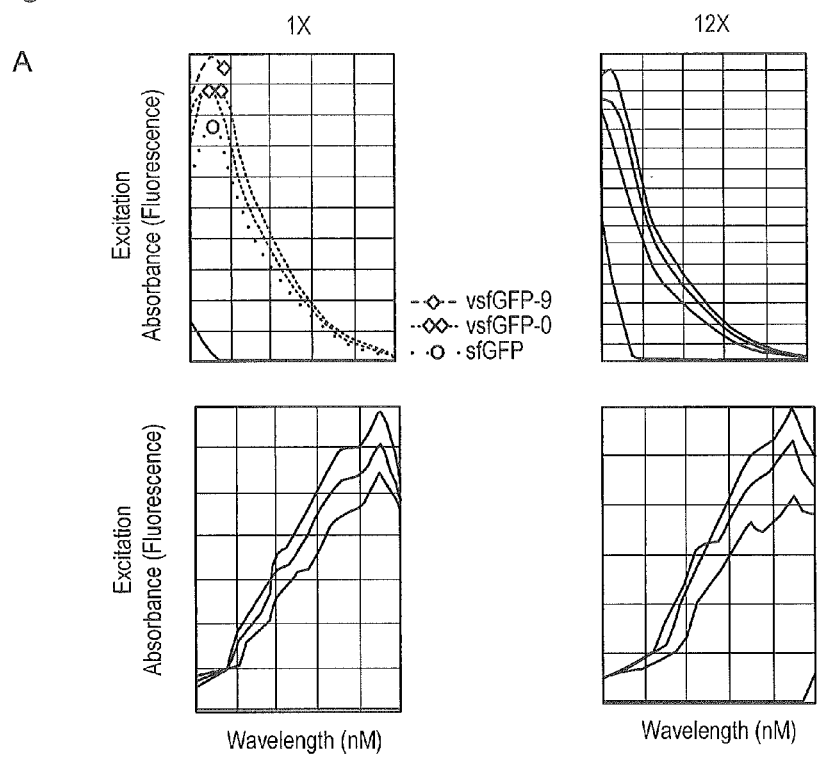
| Protein | Calculated MW | ε | Slope | Brightness (per mole) | Relative brightness |
|---------|---------------|-------|-------|----------------------|---------------------|
| sfGFP | 27604 | 19035 | 91642 | 1.74E+09 | 1 |
| vsfGFP-0 | 39210.9 | 44600 | 59056 | 2.63E+09 | 1.51 |
| vsfGFP-9 | 40286.1 | 46090 | 59834 | 2.76E+09 | 1.58 |
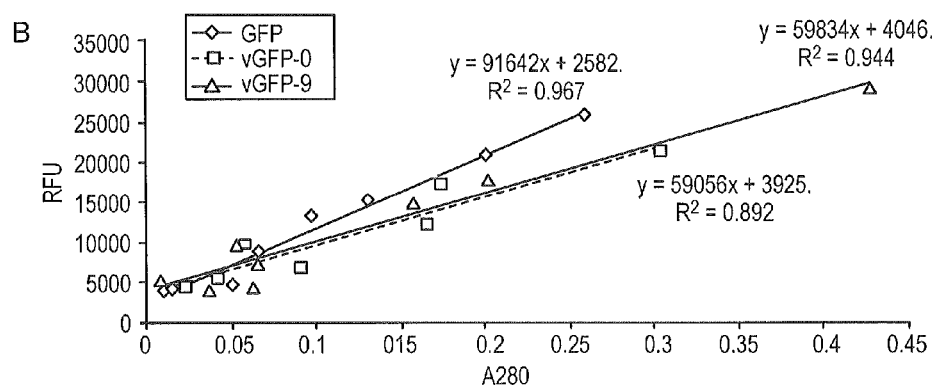

Figure 15
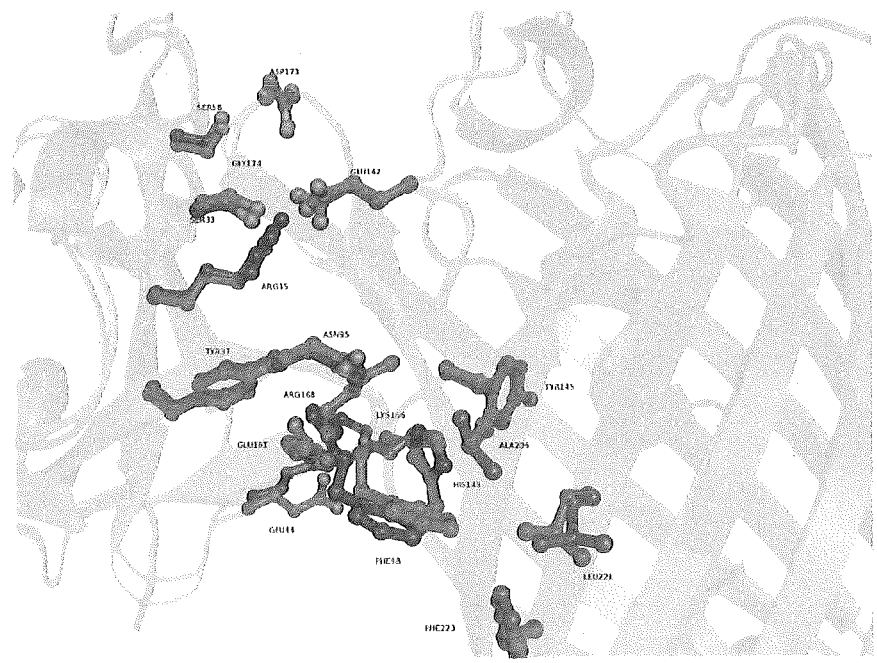
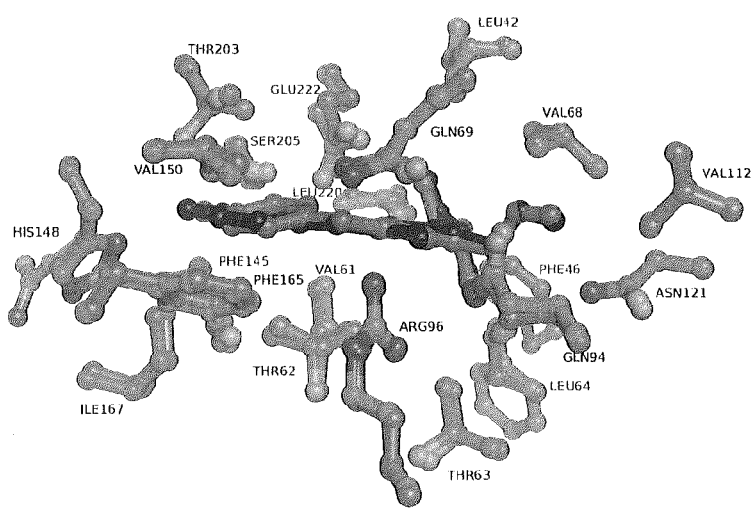

Figure 16
A
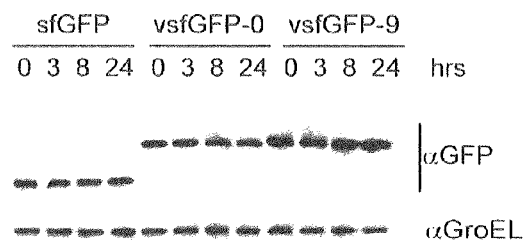
B
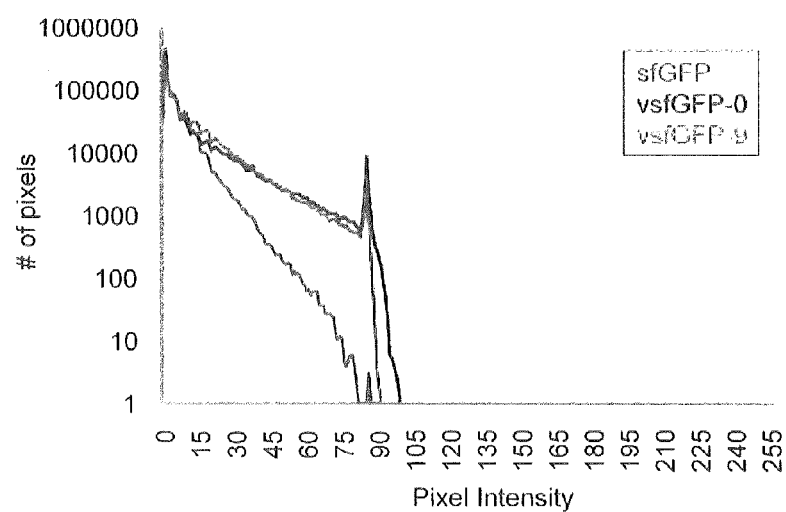
C
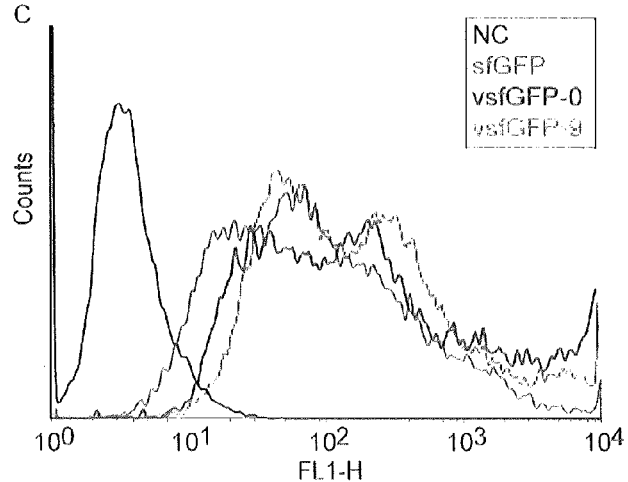
D
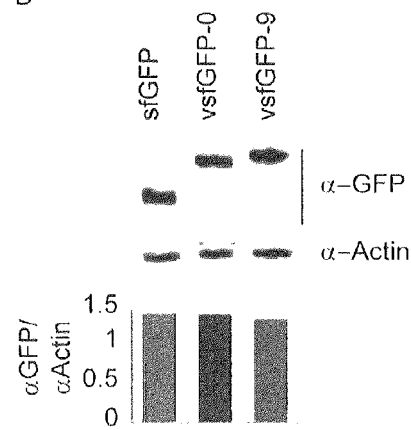

Figure 18A

```
Met Ala Asp Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Gly Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
        50                  55                  60

Ser Val Lys Gly Arg Phe Thr Ile Ser Arg Asp Asp Ala Arg Asn Thr
65                      70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser Arg Asn Ser Ile Ser Ser Leu Ser Ile Pro Ser
        115                 120                 125

Thr Val Pro Arg Ala Arg Asp Pro Pro Val Asp Met Ala Ser Ser Glu
        130                 135                 140

Asp Val Ile Lys Glu Phe Met Arg Phe Lys Val Arg Met Glu Gly Ser
145                 150                 155                 160

Val Asn Gly His Glu Phe Glu Ile Glu Gly Glu Gly Glu Gly Arg Pro
```

Figure 18A (continued)

```
Tyr Glu Gly Thr Gln Thr Ala Lys Leu Lys Val Thr Lys Gly Gly Pro
            180                 185                 190

Leu Pro Phe Ala Trp Asp Ile Leu Ser Pro Gln Phe Gln Tyr Gly Ser
        195                 200                 205

Lys Ala Tyr Val Lys His Pro Ala Asp Ile Pro Asp Tyr Leu Lys Leu
    210                 215                 220

Ser Phe Pro Glu Gly Phe Lys Trp Glu Arg Val Met Asn Phe Glu Asp
225                 230                 235                 240

Gly Gly Val Val Thr Val Thr Gln Asp Ser Ser Leu Gln Asp Gly Glu
                245                 250                 255

Phe Ile Tyr Lys Val Lys Leu Arg Gly Thr Asn Phe Pro Ser Asp Gly
            260                 265                 270

Pro Val Met Gln Lys Lys Thr Met Gly Trp Glu Ala Ser Thr Glu Arg
            275                 280                 285

Met Tyr Pro Glu Asp Gly Ala Leu Lys Gly Glu Ile Lys Met Arg Leu
    290                 295                 300

Lys Leu Lys Asp Gly Gly His Tyr Asp Ala Glu Val Lys Thr Thr Tyr
305                 310                 315                 320

Met Ala Lys Lys Pro Val Gln Leu Pro Gly Ala Tyr Lys Thr Asp Ile
            325                 330                 335

Lys Leu Asp Ile Thr Ser His Asn Glu Asp Tyr Thr Ile Val Glu Gln
                340                 345                 350

Tyr Glu Arg Ala Glu Gly Arg His Ser Thr Gly Ala Gly Leu Tyr Lys
        355                 360                 365
```

Figure 18B

```
atggccgatg tgcagctgct ggagtctggg ggagccttgg tgcagccggg ggggtctctg     60
agactctcct gtgcagcctc tggattcccc gtcaatcgct atagtatggg gtggtaccgc    120
caggctccag ggaaggagcg cgagtgggtc gcgggtatga gtagtgctgg tgatcgttca    180
agttatgaag actccgtgaa gggccgattc accatctcca gagacgacgc caggaatacg    240
gtgtatctgc aaatgaacag cctgaaacct gaggacacgg ccgtgtatta ctgtaatgtc    300
aatgtgggct ttgagtactg gggccagggg accaggtca ccgtctcctc aaggaattcg    360
atatcaagct tatcgatacc gtcgacggta ccgcgggccc gggatccacc ggtcgacatg    420
gcctcctccg aggacgtcat caaggagttc atgcgcttca aggtgcgcat ggagggctcc    480
gtgaacggcc acgagttcga gatcgagggc gagggcgagg gccgcccta cgagggcacc    540
cagaccgcca agctgaaggt gaccaagggc ggccccctgc cttcgcctg ggacatcctg    600
tcccctcagt tccagtacgg ctccaaggcc tacgtgaagc acccgccga catccccgac    660
tacttgaagc tgtccttccc cgagggcttc aagtgggagc gcgtgatgaa cttcgaggac    720
ggcggcgtgg tgaccgtgac ccaggactcc tccctgcagg acggcgagtt catctacaag    780
gtgaagctgc gcggcaccaa cttcccctcc gacggccccg taatgcagaa gaagaccatg    840
ggctgggagg cctccaccga gcggatgtac cccgaggacg gcgcctgaa ggcgagatc    900
aagatgaggc tgaagctgaa ggacggcggc cactacgacg ccgaggtcaa gaccacctac    960
atggccaaga agcccgtgca gctgcccggc gcctacaaga ccgacatcaa gctggacatc   1020
acctcccaca accaggacta caccatcgtg gaacagtacg agcgcgccga gggccgccac   1080
tccaccggcg ccggcctgta caagtaa                                        1107
```

Figure 19A

```
Met Ala Asp Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
            35                  40                  45

Trp Val Ala Gly Met Ser Ser Ala Gly Asp Arg Ser Ser Tyr Glu Asp
        50              55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Ser Asn Val Asn Val Gly Phe Glu Tyr Trp Gly Gln Gly Thr Gln
            100                 105                 110

Val Thr Val Ser Ser Arg Asn Ser Ile Ser Ser Leu Ser Ile Pro Ser
            115                 120                 125

Thr Val Pro Arg Ala Arg Asp Pro Pro Val Asp Met Ala Ser Ser Glu
        130             135                 140

Asp Val Ile Lys Glu Phe Met Arg Phe Lys Val Arg Met Glu Gly Ser
145                 150                 155                 160

Val Asn Gly His Glu Phe Glu Ile Glu Gly Glu Gly Glu Gly Arg Pro
                165                 170                 175

Tyr Glu Gly Thr Gln Thr Ala Lys Leu Lys Val Thr Lys Gly Gly Pro
            180                 185                 190

Leu Pro Phe Ala Trp Asp Ile Leu Ser Pro Gln Phe Gln Tyr Gly Ser
        195                 200                 205

Lys Ala Tyr Val Lys His Pro Ala Asp Ile Pro Asp Tyr Leu Lys Leu
    210                 215                 220
```

Figure 19A (continued)

```
Ser Phe Pro Glu Gly Phe Lys Trp Glu Arg Val Met Asn Phe Glu Asp
225                 230                 235                 240

Gly Gly Val Val Thr Val Thr Gln Asp Ser Ser Leu Gln Asp Gly Glu
            245                 250                 255

Phe Ile Tyr Lys Val Lys Leu Arg Gly Thr Asn Phe Pro Ser Asp Gly
            260                 265                 270

Pro Val Met Gln Lys Lys Thr Met Gly Trp Glu Ala Ser Thr Glu Arg
        275                 280                 285

Met Tyr Pro Glu Asp Gly Ala Leu Lys Gly Glu Ile Lys Met Arg Leu
    290                 295                 300

Lys Leu Lys Asp Gly Gly His Tyr Asp Ala Glu Val Lys Thr Thr Tyr
305                 310                 315                 320

Met Ala Lys Lys Pro Val Gln Leu Pro Gly Ala Tyr Lys Thr Asp Ile
                325                 330                 335

Lys Leu Asp Ile Thr Ser His Asn Glu Asp Tyr Thr Ile Val Glu Gln
            340                 345                 350

Tyr Glu Arg Ala Glu Gly Arg His Ser Thr Gly Ala Gly Leu Tyr Lys
        355                 360                 365
```

Figure 19B

```
atggccgatg tgcagctggt ggagtctggg ggagccttgg tgcagccggg ggggtctctg      60
agactctcct gtgcagcctc tggattcccc gtcaatcgct atagtatgag gtggtaccgc     120
caggctccag ggaaggagcg cgagtgggtc gcggttatga gtagtgctgg tgatcgttca     180
agttatgaag actccgtgaa gggccgattc accatctcca gagacgacgc caggaatacg     240
gtgtatctgc aaatgaacag cctgaaacct gaggacacgg ccgtgtatta ctcgaatgtc     300
aatgtgggct ttgagtactg gggccagggg acccaggtca ccgtctcctc aaggaattcg     360
atatcaagct tatcgatacc gtcgacggta ccgcgggccc gggatccacc ggtcgacatg     420
gcctcctccg aggacgtcat caaggagttc atgcgcttca aggtgcgcat ggagggctcc     480
gtgaacggcc acgagttcga gatcgagggc gagggcgagg gccgccccta cgagggcacc     540
cagaccgcca agctgaaggt gaccaagggc ggccccctgc cttcgcctg ggacatcctg     600
tcccctcagt tccagtacgg ctccaaggcc tacgtgaagc accccgccga catccccgac     660
tacttgaagc tgtccttccc cgagggcttc aagtgggagc gcgtgatgaa cttcgaggac     720
ggcggcgtgg tgaccgtgac ccaggactcc tccctgcagg acggcgagtt catctacaag     780
gtgaagctgc gcggcaccaa cttcccctcc gacggcccc taatgcagaa gaagaccatg     840
ggctgggagg cctccaccga gcggatgtac cccgaggacg gcgccctgaa gggcgagatc     900
aagatgaggc tgaagctgaa ggacggcggc cactacgacg ccgaggtcaa gaccacctac     960
atggccaaga gccccgtgca gctgccggc gcctacaaga ccgacatcaa gctggacatc    1020
acctcccaca acgaggacta caccatcgtg gaacagtacg agcgcgccga gggccgccac    1080
tccaccggcg ccggcctgta caagtaa                                        1107
```

Figure 20

```
M A Q V Q L Q E S G G G L V
Q A G G S L T L S C T Y S G L T F D D Y
N M G W F R Q G P G K E R E R V S A I S
F R G I T Y Y V D S V K G R F T I S R D
N A K K T L Y L Q M N G L T P D D T A T
Y Y C A G S R F L S P F V R D G D T K L
I N D W G Q G T Q V T V S S
```

NANOBODY-FLOURESCENT PROTEIN FUSION

CROSS REFERENCE TO RELATED APPLICATIONS

This application is a U.S. National Stage entry of PCT/SG2015/000033, filed Feb. 6, 2015, which claims the benefit of priority to U.S. Provisional Application No. 61/965,782, filed Feb. 7, 2014, and U.S. Provisional Application No. 62/078,269, filed Nov. 11, 2014, the entire contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 3, 2015, is named 97520-922222.txt and is 34,244 bytes in size.

FIELD OF THE INVENTION

This invention is generally related to fluorescent reporters, fusion proteins, custom antibody generation, cell labeling, expression analysis, protein engineering, and single-domain antibodies (nanobodies).

BACKGROUND OF THE INVENTION

The discovery of the green fluorescent protein (GFP) in 1962 by Osamu Shimomura and coworkers (1) was a seminal event that spawned subsequent revolution in genetically encoded fluorescent proteins. Since then, GFP has remained the archetypal fluorescent protein and has received the greatest attention and widest application (2). GFP and other fluorescent proteins are now solidly foundational tools in cell biology and numerous biotechnological applications including molecular probes (3). Past and current work on GFP and other fluorescent proteins may be conceptually divided into the pursuit of general improvements as well as specific application development (4, 5). Notable general advancements include the development of brighter fluorescence, higher photostability, alternative colors, and defined oligomerization state (6-11). More specific applications are enabled by specialized variants that are sensitive to pH, oxygen tension, cation concentrations, or other environmental conditions; recently, this has been further extended to photoswitching/photoactivation behavior that has been leveraged for super-resolution imaging applications (12-15).

Novel variants of existing fluorescent proteins as well as new fluorescent proteins continue to be an active area of research (2). Typically, control of both spectral and biochemical characteristics has been sought. Spectrally, this includes increasing or decreasing brightness, photostability, and quantum yield and modulation of excitation and emission peaks and curves. Biochemically, control of protein oligomerization, stability, folding kinetics, and other interactions (either up or down for all of these) enable different usage scenarios as well (6, 9, 16-20). At the core, spectral characteristics, primarily overall brightness during imaging applications (a complex function of excitation quantum cross section, quantum yield for fluorescence, Stokes shift, and specific imaging system components) are still deeply useful when improved. This has driven the extensive in vitro mutagenesis and evolution of GFP as well as the search for other naturally fluorescent proteins (4, 13, 17, 18, 20-22). Simplistically, this pursuit of brightness still seems reasonable because small molecule (i.e., non-genetically encodable) fluorophores continue to boast higher overall brightness than fluorescent proteins (ex. fluorescein is still brighter than all GFP variants (10). Therefore, variants of GFP and other fluorescent proteins that exhibit improved overall brightness are still valuable additions to the fluorescent protein toolbox and, if biochemical characteristics are preserved, are immediately available for upgrading most existing applications.

The key biochemical feature of GFP that enables the vast majority of applications is its ability to spontaneously fold as a single domain, resulting in a (generally) facile, nontoxic, stable fusion partner for a variety of proteins (11). Fusion to a protein of interest enables studies of protein localization, interactions, and stability (3, 23-25). Fusion to antigen binding proteins, notably antibodies, enables a large array of in vivo and in vitro affinity tagging, purification, identification, and visualization applications (7, 9, 13, 24, 26-29). Recently, identification of single domain antibodies, or nobodies, that bind to GFP and modulate its fluorescence has resulted in several additional novel tools for further application development (30-33). Like GFP itself, nanobodies are ideal fusion partners that fold spontaneously into a single stable domain (34-36). Thus, these GFP binding nanobodies have been used for intentional association of proteins (one fused to GFP and one fused to the nanobody) in vivo, resulting in an enhanced or reduced fluorescence readout (33). Furthermore, chromobodies couple a nanobody with arbitrary specificity to any fluorophore for detection, enabling in vivo as well as in vitro fluorescent molecular probe or localization reagents (31, 37-40). Despite several reported exceptions (24, 27, 41), however, one major drawback for antibody-fluorescent protein fusions remains the general production of these reagents, as the disulfide bonds often required in nanobodies and other antibodies typically require oxidizing conditions that preclude proper folding of GFP (39) and thereby require modified host strains (39, 42-44) or tolerating low periplasmic yields (43, 45-47).

Recent results have demonstrated that one GFP variant, termed sfGFP (48), is capable of folding properly in the bacterial periplasm (49-51), where most variants (notably wtGFP and EGFP) are very dim or nonfluorescent. Furthermore, sfGFP has been shown to enhance the proper folding of protein domains fused to it (48). Therefore, in addition to expanding the use of GFP variants to the study of the bacterial periplasm and eukaryotic endoplasmic reticulum compartments, sfGFP could have an additional benefit in improving cytoplasmic expression of antibody domains.

BRIEF SUMMARY OF THE INVENTION

In one aspect, a fluorescent fusion protein is provided, the fusion protein comprising a fluorescent protein fused to a single domain antibody. In some embodiments, the fluorescent protein is fused to the single domain antibody via a linker. In some embodiments, the linker joins the C-terminal end of the fluorescent protein to the N-terminus of the single domain antibody. In some embodiments, the fluorescent fusion protein converts between a monomeric complex and dimeric complex by varying the length of the linker. In some embodiments, the linker comprises natural or non-natural amino acids. In some embodiments, the amino acids are fused in frame with the coding regions for the fluorescent protein and the single domain antibody. In some embodiments the fluorescent fusion protein is a dimer having a short linker. In some embodiments the fluorescent fusion protein is a monomer having a longer linker. In some embodiments, the fluorescent protein is a green fluorescent protein (GFP) or variant thereof.

Thus, in some embodiments, a fluorescent fusion protein is provided, the protein comprising:
a green fluorescent protein (GFP) or variant thereof;
a single domain antibody; and
a linker linking the C-terminal of GFP to the N-terminal of the single domain antibody,
wherein the fluorescent fusion protein converts between a monomeric complex and dimeric complex by varying the linker length.

In some embodiments, the GFP is selected from wild-type GFP (SEQ ID NO:11), sfGFP (SEQ ID NO:6), CFP (SEQ ID NO:18), sfCFP (SEQ ID NO:4), YFP (SEQ ID NO:16) or sfYFP (SEQ ID NO:8). In some embodiments, the GFP comprises or consists of an amino acid sequence that is substantially identical to the amino acid sequence of wild-type GFP, sfGFP, CFP, sfCFP, YFP or sfYFP. In some embodiments, the GFP comprises or consists of an amino acid sequence at least 90%, 91%, 92%, 93%, 94%, 95%, 96%, 97%, 98%, or 99% identical to SEQ ID NOs: 11, 6, 18, 4, 16, or 8.

In some embodiments, the GFP is a GFP variant that is capable of binding a single domain antibody. In some embodiments, the linker comprises 0 to 9 amino acids.

In some embodiments, the fluorescent fusion protein is a dimer. In some embodiments, the dimer comprises two GFP polypeptides or variants thereof, and two single domain antibody polypeptides. In some embodiments, the dimer comprises zero (0), one, two, or three amino acids linking the C-terminal of GFP to the N-terminal of the single domain antibody.

In some embodiments, the fluorescent fusion protein is a monomer. In some embodiments, the monomer comprises four, five, six, seven, eight, or nine amino acids linking the C-terminal of GFP to the N-terminal of the single domain antibody.

In some embodiments, the linker comprises 9 amino acids, and the fusion protein has a single particle brightness at least about 1.3 times greater than the single particle brightness of GFP alone under identical excitation conditions.

In some embodiments, the linker comprises 0 amino acids, and the fusion protein has a single particle brightness at least about 2.5 times greater than the single particle brightness of GFP alone under identical excitation conditions.

In some embodiments, the fluorescence of the fluorescent fusion proteins described herein is increased about 7-fold compared to GFP or sfGFP alone at a pH of about 3.5.

In some embodiments, the single domain antibody is a single chain $V_HH$ nanobody. In some embodiments, the single domain antibody comprises or consists of the amino acid sequence of SEQ ID NO:1. In some embodiments, the single domain antibody comprises or consists of an amino acid sequence substantially identical to SEQ ID NO:1. In some embodiments, the single domain antibody comprises or consists of an amino acid sequence at least 90%, 91%, 92%, 93%, 94%, 95%, 96%, 97%, 98%, or 99% identical to SEQ ID NO: 1. In some embodiments, the nanobody comprises or consists of the amino acid sequence shown in FIG. 18A, 19A, or 20, or an amino acid sequence at least 90%, 91%, 92%, 93%, 94%, 95%, 96%, 97%, 98%, or 99% identical to the amino acid sequence shown in FIG. 18A, 19A, or 20.

In some embodiments, the fusion protein comprises (i) a GFP or variant thereof comprising an amino acid sequence at least 90%, 91%, 92%, 93%, 94%, 95%, 96%, 97%, 98%, or 99% identical to SEQ ID NOs: 11, 6, 18, 4, 16, or 8, and (ii) a single domain antibody comprising an amino acid sequence at least 90%, 91%, 92%, 93%, 94%, 95%, 96%, 97%, 98%, or 99% identical to SEQ ID NO: 1 or the amino acid sequence shown in FIG. 18A, 19A, or 20.

In another aspect, a nucleic acid molecule encoding the fluorescent fusion proteins described herein is provided. In some embodiments, the nucleic acid molecule comprises:
a nucleic acid sequence encoding a green fluorescent protein (GFP) or variant thereof;
a nucleic acid sequence encoding a single domain antibody; and
a nucleic acid sequence encoding a linker located between the C-terminus of GFP and the N-terminus of the single domain antibody.

In some embodiments, the nucleic acid molecule comprises a nucleic acid sequence encoding (i) a GFP, or variant thereof, selected from wild-type GFP, sfGFP, CFP, sfCFP, YFP or sfYFP, and/or (ii) an amino acid sequence that is substantially identical to the amino acid sequence of wild-type GFP, sfGFP, CFP, sfCFP, YFP or sfYFP, and/or (iii) an amino acid sequence at least 90%, 91%, 92%, 93%, 94%, 95%, 96%, 97%, 98%, or 99% identical to SEQ ID NOs: 11, 6, 18, 4, 16, or 8. In some embodiments, the nucleic acid molecule comprises a nucleic acid sequence encoding a single domain antibody. In some embodiments, the nucleic acid molecule comprises a nucleic acid sequence encoding a single domain antibody comprising (i) the amino acid sequence of SEQ ID NO:1, and/or (ii) an amino acid sequence substantially identical to SEQ ID NO:1, and/or (iii) an amino acid sequence at least 90%, 91%, 92%, 93%, 94%, 95%, 96%, 97%, 98%, or 99% identical to SEQ ID NO: 1. In some embodiments, the nucleic acid molecule comprises a nucleic acid sequence encoding a linker having the amino acid sequence THGMDELYK (SEQ ID NO:10). In some embodiments, the nucleic acid sequence encoding the linker of SEQ ID NO:10 comprises or consists of SEQ ID NO:9.

In another aspect, an expression cassette comprising nucleic acid sequences, e.g., polynucleotide sequences, that encode the fluorescent fusion proteins described herein is provided. In some embodiments, the expression cassette comprises:
a nucleic acid sequence encoding a green fluorescent protein (GFP) or variant thereof;
a nucleic acid sequence encoding a single domain antibody; and
a nucleic acid sequence encoding a linker located between the C-terminus of GFP and the N-terminus of the single domain antibody.

In some embodiments, the nucleic acid sequence encoding a green fluorescent protein (GFP) or variant thereof comprises or consists of SEQ ID NOs: 12, 5, 17, 3, 15, or 7, and/or a nucleic acid sequence at least 90%, 91%, 92%, 93%, 94%, 95%, 96%, 97%, 98%, or 99% identical to SEQ ID NOs: 12, 5, 17, 3, 15, or 7.

In some embodiments, the expression cassette comprises regulatory sequences that regulate expression of the nucleic acid sequences. For example, the expression cassette can comprise a promoter sequence and terminator sequences.

In another aspect, a cell that comprises the fluorescent fusion proteins described herein is provided. In some embodiments, the cell comprises an expression cassette comprising nucleic acid sequences that encode the fluorescent fusion proteins described herein. In one embodiment, the cell is a bacterial cell. In some embodiments, the cell is a modified cell, e.g., a modified bacterial cell, that does not exist in nature. In some embodiments, the cell comprises a heterologous nucleic acid molecule or vector that encodes a fluorescent fusion protein described herein.

In another aspect, a method for producing a fusion protein is provided. The method comprises fusing a single domain antibody to a fluorescent protein via a linker, where the length of the linker determines the oligomeric structure of the fusion protein. In some embodiments, the C-terminus of the fluorescent protein is linked to the N-terminus of the single domain antibody. In some embodiments, the linker comprises 0 to 9 amino acids. In some embodiments, the fusion protein is a monomer and comprises a linker of zero, one or two amino acids. In some embodiments, the fusion protein is a dimer and comprises a linker of four, five, six, seven, eight, or nine amino acids. In some embodiments, the fluorescent protein is GFP or a variant thereof.

In another aspect, a method for expressing a fluorescent fusion protein in the periplasm of a bacterial cell is provided. In some embodiments, the method comprises transfecting (or transforming) an expression cassette comprising nucleic acid sequences that encode the fluorescent fusion proteins described herein into a bacterial cell, and expressing the fusion protein encoded by the expression cassette in the periplasm. In some embodiments, the method results in a properly folded and functional fluorescent fusion protein that is expressed in the periplasm. In some embodiments, the method further comprises expressing a properly folded and functional fluorescent fusion protein in the cytoplasm of the transfected bacterial cell. In some embodiments, the properly folded and functional fluorescent fusion protein is expressed in both the periplasm and cytoplasm of the transfected bacterial cell.

BRIEF DESCRIPTION OF THE DRAWINGS

FIG. 1. Schematic of the fusion protein. (A) Diagram of the fusion protein. Gene encoding GFP is in green, GFP-binding enhancer nanobody in red. Variable length peptide linker is shown as a black line joining the two domains. (B) Model of expected fusion protein behavior. With a long linker, the enhancer from one fusion protein has enough conformational freedom to bind to the GFP it is already attached to through the linker. With a short linker, the relative orientation of the enhancer and GFP is constrained so that an intramolecular interaction is impossible; in this case, forming a dimeric complex with another fusion protein results in two enhanced GFPs with a predicted corresponding increase in specific fluorescence, as measured per protein complex.

FIG. 6. Macromolecular characterization of sfGFP and the new variants. A, Absorption, fluorescence excitation and emission spectra of sfGFP, vsfGFP-0 and vsfGFP-9. Samples were measured at two different concentrations. The emission spectra were measured from 500 nm to 600 nm under 520 nm excitation. The samples were emitted at 490 nm to obtain fluorescence excitation spectra from 400 nm to 500 nm. B. Measurement of relative brightness (fluorescence intensity over extinction coefficient).

FIG. 15. Detailed structural comparison of the vGFP-0 and GFP:Enhancer complex structures. (A) Positions of amino acids at the interface of the GFP:Enhancer complex (cyan) and of the vGFP-0 complex (red, Enhancer; green, sfGFP; domains are from different proteins). A cartoon representation of the GFP:Enhancer complex is shown in transparent cyan and of the vGFP-0 complex in red (Enhancer domain) and green (sfGFP domain). (B) Positions of amino acids within 4.0 Å of the chromophore of the GFP:Enhancer complex (residues in cyan, chromophore in black) and of the vGFP-0 complex (residues in green, chromophore in red).

FIG. 16. Additional analyses for in vivo expression of vsfGFP proteins. (A) In vivo stability assay. Equal quantities of *E. coli* expressing sfGFP or vsfGFP variants at different time points were analyzed by immunoblotting with α-GFP and α-GroEL. Times indicate the time after a 3-hour induction period (i.e., 0 is immediately after stopping the 3 hour induction) at which the sample was collected. (B) Quantification of fluorescence brightness in 293T cells. Intensity histograms of the images in FIG. 3C are shown. sfGFP, green; vsfGFP-0, blue; vsfGFP-9, red. All images were acquired with constant illumination and capture parameters and scaled in Adobe Photoshop simultaneously with identical parameters. vsfGFP-0 and vsfGFP-9 images have more bright pixels despite similar cell density. (C) Flow cytometry analysis of 293T cells expressing sfGFP (green), vsfGFP-0 (blue), and vsfGFP-9 (red) proteins. NC, negative control (cells transfected, with empty vector). Geometric means for NC, sfGFP, vsfGFP-0, and vsfGFP-9 are 3, 77, 211, and 177, respectively. (D) Quantification of GFP protein levels in 293T cells. (top) Immunoblot of samples from panel C using α-GFP antibody. α-actin was used as a loading control. (bottom) Densitometric quantification of GFP levels relative to actin.

FIG. 18. (A) shows the amino acid sequence and (B) shows the nucleotide sequence of a representative anti-GFP nanobody (see European patent application EP 2 055 718 A1, sequence listing, which is incorporated by reference herein).

FIG. 19. (A) shows the amino acid sequence and (B) shows the nucleotide sequence of another representative anti-GFP nanobody (referred to as mutant C92S) (see European patent application EP 2 055 718 A1, sequence listing, which is incorporated by reference herein).

FIG. 20. The amino acid sequence of $V_HH$ fragment of fluorescent chromobody against cytokeratin-8.

DEFINITIONS

Figure 2:
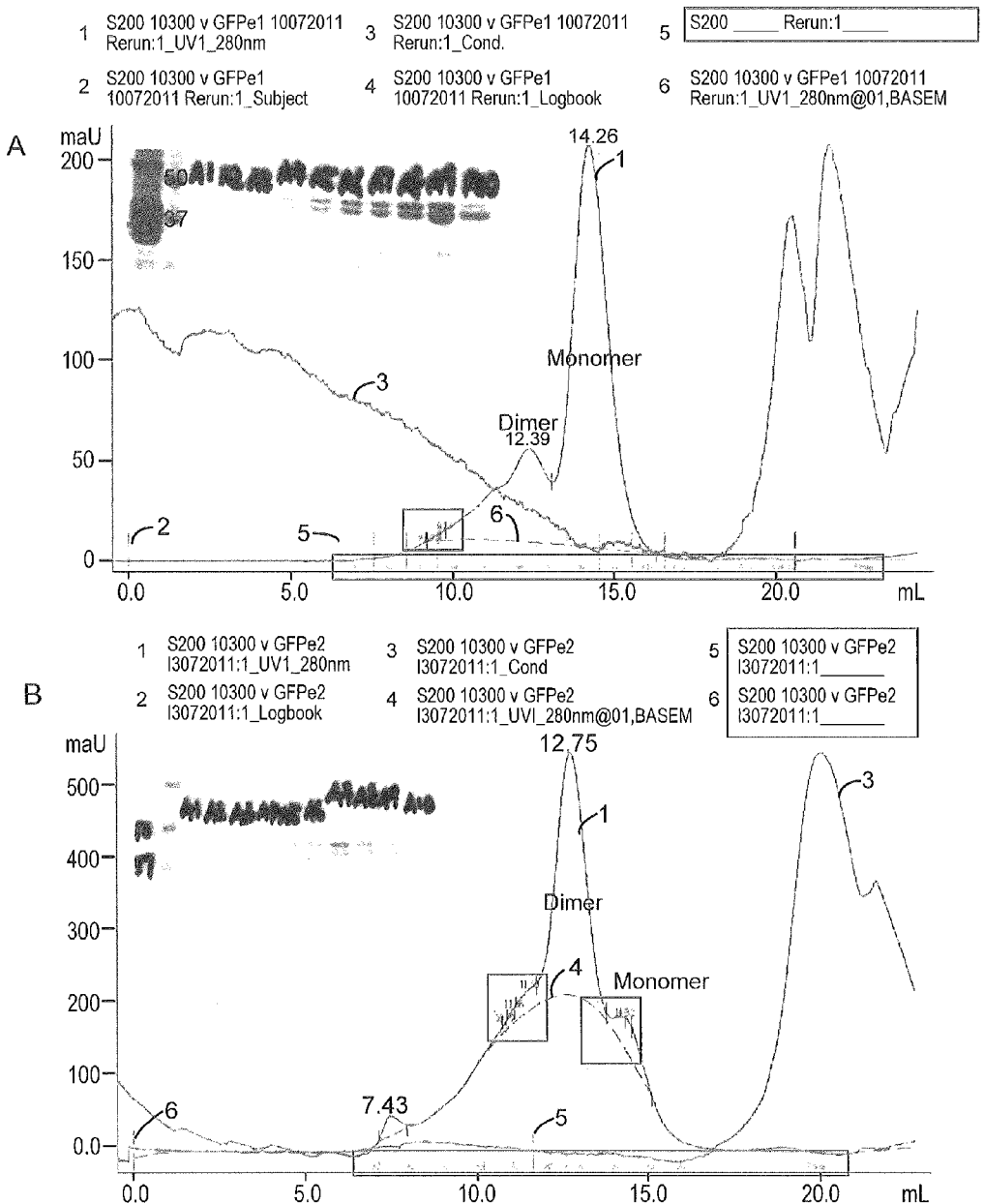
FIG. 2. A GFP-enhancer fusion protein forms a monomer or dimer dependent on linker length. (A) Gel filtration and SDS-PAGE analysis of purified. GFP-enhancer fusion protein containing a long (9aa) linker. The UV absorbance (protein concentration) from a gel filtration run is shown in blue. Fractions collected are indicated in red just above the x-axis (A1-A15). Peaks corresponding to the monomer and dimer of the fusion protein are indicated. Inset shows SDS-PAGE analysis. The first lane is input protein, the second lane is a molecular weight marker with 50 kD and 37 kD markers shown. Fractions from the gel filtration run are indicated in black in the subsequent lanes. The predicted molecular weight of the GFP-enhancer fusion is approximately 40 kD. (B) As in (A), but using a fusion protein with a 0 aa linker length. The predicted molecular weight of this fusion protein is approximately 1 kD less than the protein shown in (A).

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989); Ausubel et al., CURRENT PROTOCOLS IN MOLECULAR BIOLOGY, John Wiley and Sons (Hoboken, N.Y. 1995). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine. (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences or subsequences that have a specified percentage of amino acid residues or nucleotides that are the same (i.e., at least about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see e.g., NCBI web site http://www.ncbi.nlm.nih.gov/BLAST/ or the like). The definition includes sequences that have deletions and/or additions, as well as those that have substitutions. As described below, algorithms can account for gaps and the like. When not specified, identity or substantial identity is determined over the entire length of the reference sequence. When specified, identity can be determined over a region that is at least about 10 amino acids or nucleotides in length, at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An exemplary algorithm suitable for determining percent sequence identity and sequence similarity is BLAST 2.0 algorithm, which is described in Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915).

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

To determine which amino acid of a first protein "corresponds" to the position of an amino acid in a second protein, the amino acid sequences of the two proteins are optimally aligned (e.g., using a BLAST algorithm). This is particularly useful, for example, where two proteins have high homology but where one protein contains one or more insertions or deletions relative to the second protein. In such cases, for example, position 57 of a first protein may align with position 51 in a second protein when the two proteins are optimally aligned. Thus position 51 of the second protein "corresponds" to position 57 of the first protein.

A "heterologous sequence," "heterologous polypeptide," or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA or by being linked to a heterologous promoter or by being linked to a reporter gene, etc.

"Expression cassette" or "expression vector" refers to a polynucleotide comprising a promoter or other regulatory sequence operably linked to a sequence encoding a protein.

As used herein, the term "single-domain antibody" (sdAb) refers to an antibody fragment consisting of a single monomeric variable antibody domain. In some embodiments, the sdAb comprises a heavy chain (e.g., a $V_HH$ fragment). The term single-domain antibody is used interchangeably with the term "nanobody".

DETAILED DESCRIPTION OF THE INVENTION

Multiple single-domain antibodies (nanobodies) to GFP have been developed and reported. One has an interesting property of enhancing GFP fluorescence upon binding (the nanobody is termed the "enhancer"), and the crystal structure for the complex is known. Typical applications have focused on the explicit use of the specific binding of enhancer to GFP, allowing fluorescent readouts of colocalization or engineering artificial interactions/colocalization. The crystal structure of the GFP-enhancer nanobody complex is known. In this structure, the GFP appears as a cylindrical beta-barrel structure. The enhancer nanobody binds to the GFP cylinder on the side close to one of the "ends" (i.e., towards the edge of the flat part or "lid" of a cylinder). The C-terminus of GFP in this complex is on the same side of the cylinder but on the other "lid" and thus distant from the nanobody. The N-terminus of the nanobody is found opposite to the interaction surface of the nanobody. Thus, a direct fusion of GFP to the nanobody, where the GFP C-terminus is joined to the nanobody N-terminus, results in a fusion protein that is predicted to have a structure that precludes interaction of the nanobody with its attached GFP (i.e., an internal complex is not possible). The most favorable interaction is therefore predicted to be a dimer between two GFP-nanobody fusions, where the nanobody of one fusion binds the GFP of the other and vice versa. This dimer enhances the fluorescence of both GFPs and also results in a tight association between them, such that the specific fluorescence signal is expected to be 8-fold greater than a single GFP protein alone. Adding a peptide linker of sufficient length between the GFP and the nanobody allows an intramolecular complex to be formed, resulting in a monomer with enhanced GFP fluorescence.

We have created a fusion between GFP and enhancer (e.g., the protein comprising SEQ ID NO:1) based on the crystal structure of the complex that results in either a monomeric or dimeric enhanced GFP protein (FIG. 1A, B); these fusion proteins result in higher specific fluorescence and thus more useful fluorescent proteins compared with the original GFP protein. In the case of the dimeric protein, there is an additional theoretical two-fold improvement in specific fluorescence over the single GFP-enhancer complex (FIG. 1B). This results in an outstanding reporter that can be used to label cells or as a reporter for gene or protein expression. Furthermore, this invention converts cognate binding (where GFP binds only to enhancer, i.e., two different molecules bind) into a homodimer interaction (where two GFP-enhancer fusions bind each other, i.e., two of the same molecules bind), thereby complementing existing fluorescent fusion protein strategies using GFP-enhancer complexes. When used with a superfolder GFP variant, this construct is able to fold properly in both the cytoplasm and periplasm of bacteria, indicating robustness to redox conditions. This overcomes traditional limitations in antibody-GFP fusions where the antibody requires oxidizing conditions to fold (such as the periplasm) while the GFP requires reducing conditions to fold (such as the cytoplasm).

We developed a class of GFP variants we denote as vGFP. We have fused sfGFP to a GFP-binding nanobody termed the Enhancer (33) that increases the brightness of EGFP 1.5-fold. Structure-based design has enabled us to engineer reflexive binding of the enhancer to its fused sfGFP (leading to a monomeric species) as well as enforced binding of the enhancer to a non-fused sfGFP (leading to a dimeric species). Other properties of the enhancer-bound sfGFP, namely increased brightness relative to unbound sfGFP and proper folding in oxidizing environments, are preserved. The monomeric vsfGFP variant provides a compact, spontaneously folding, stable, and nontoxic genetically encoded fluorophore that demonstrates superior brightness to sfGFP in vitro and in vivo in both bacteria and eukaryotic cells as well as at the single molecule level. The dimeric vsfGFP variant provides a stable complex with an additional 2-fold increased single-particle brightness that is an ideal fluorophore for many molecular probe applications, as it naturally presents a bidentate binding platform when fused with another antibody or other binding determinants. Fusion of vGFP to nanobodies enables generalized production of fluorescently tagged antibodies in either the bacterial cytoplasm or periplasm with tunable dimerization. The vGFP strategy is generalizable to other fluorophores including all close GFP variants (such as CFP and YFP) but also should be viable for improving the fluorescence and controlling the oligomerization state of other proteins such as mCherry. Therefore, the successful engineering of these vGFP variants represents a novel platform for further upgrades to nearly all currently available fluorescent proteins.

This disclosure provides a very strong fluorophore that can be encoded genetically to be used for promoter/expression analysis as a simple reporter gene, as a cell label for microscopy and protein localization studies, and potentially as a fusion to another protein that can then report both on localization and homodimerization. The high specific fluorescence of this fusion is a distinct advantage for increasing the sensitivity for measuring promoters and proteins that are expressed at low levels. In addition, the homodimerization is distinct from the GFP-enhancer interaction binding mode (i.e., A binds to A versus A binds to B), so additional protein localization and interaction assays could be implemented that complement existing strategies that tag different proteins with GFP and enhancer. The use of superfolder GFP as the base GFP is found to enable fusion in general to different nanobodies and potentially other antibodies. This solves the problem of creating functional nanobodies fused to GFP; in the past this was not generally possible due to opposing redox requirements for folding of the nanobody (oxidizing) and GFP (reducing).

This disclosure also describes a general strategy (we term the vGFP strategy) for creating arbitrary monomers and dimers of proteins so long as a nanobody that binds with a compatible conformation to the protein of interest is available. This strategy could be further generalized to enable higher order complexes (tetramers or higher) depending on the orientation of binding of the nanobody to the target protein.

Other fluorescent proteins (e.g., CFP, YFP, BFP, and other GFP derivatives) could be used as alternative high sensitivity fluorophores alone or in combination with the present GFP-enhancer fusion, enabling additional assays (such as FRET) or multiple color labeling.

In summary, vsfGFP proteins are 30-50% brighter than superfolder GFP (sfGFP) in vitro and over twice as bright in vivo, with markedly improved pH resistance down to pH 3.5. Folding of protein domains fused to a vsfGFP is improved, solving the problem of differential redox requirements for producing fluorescently labeled antibodies in bacteria and resulting in a tripling of the brightness of molecular probes. The vGFP strategy is applicable to other fluorescent proteins, provides an improved GFP for upgrading nearly all existing applications, and enables new methods for tuning dimerization of arbitrary proteins and optimizing protein properties in general.

General Methods

Unless defined otherwise, all technical and scientific terms used herein have the meaning commonly understood by one of ordinary skill in the art to which this invention belongs. Practitioners are particularly directed to Green, M. R. and Sambrook, J., eds., *Molecular Cloning: A Laboratory Manual*, 4th ed., Cold Spring Harbor Laboratory Press, Cold Spring Harbor, N.Y. (2012), and Ausubel, F. M., et al. *Current Protocols in Molecular Biology* (Supplement 99), John Wiley & Sons, New York (2012), which are incorporated herein by reference, for definitions and terms of the art. Standard methods also appear in Bindereif, Schön, & Westhof (2005) *Handbook of RNA Biochemistry*, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al. (Id.); Berger and Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990), which are incorporated by reference herein.

Methods for protein purification, chromatography, electrophoresis, centrifugation, and crystallization are described in Coligan et al. (2000) *Current Protocols in Protein Science*, Vol. 1, John Wiley and Sons, Inc., New York. Methods for cell-free synthesis are described in Spirin & Swartz (2008) *Cell-free Protein Synthesis*, Wiley-VCH, Weinheim, Germany. Methods for incorporation of non-native amino acids into proteins using cell-free synthesis are described in Shimizu et al. (2006) *FEBS Journal*, 273, 4133-4140.

PCR amplification methods are well known in the art and are described, for example, in Innis et al. *PCR Protocols: A Guide to Methods and Applications*, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al. *Short Protocols in Molecular Biology*, 5th Edition, Wiley, 2002, and Innis et al. *PCR Protocols*, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al. *Proc. Natl. Acad. Sci. U.S.A.* 87:1663-1667, 1990; Eberwine et al. *Proc. Natl. Acad. Sci. U.S.A.* 89:3010-3014, 1992).

When the proteins described herein are referred to by name, it is understood that this includes proteins with similar functions and similar amino acid sequences. Thus, the proteins described herein include the wild-type prototype protein, as well as homologs, polymorphic variations and recombinantly created muteins. For example, the name "green fluorescent protein" includes the wild-type prototype protein from *Aequorea victoria* (e.g., SEQ ID NO:11), as well as homologs from other species, polymorphic variations and recombinantly created muteins. Proteins such as GFP, CFP, and YFP are defined as having similar functions if they have substantially the same biological activity or functional capacity as the wild type protein (e.g., at least 80% of either). Proteins such as GFP, CFP, and YFP are defined as having similar amino acid sequences if they have at least 80%, 85%, 90%, 91%, 92%, 93%, 94%, 95%, 96%, 97%, 98%, or 99% sequence identity to the prototype protein (e.g., SEQ ID NOs: 11, 18, and 16, respectively). The sequence identity of a protein is determined using the BLASTP program with the defaults wordlength of 3, an expectation (E) of 10, and the BLOSUM62 scoring matrix (see Henikoff and Henikoff, *Proc. Natl. Acad. Sci. USA* 89:10915-10919, 1992).

A readily conventional test to determine if a protein homolog, polymorphic variant or recombinant mutein is inclusive of a protein chaperone described herein is by specific binding to polyclonal antibodies generated against the prototype protein. For example, a green fluorescent protein includes proteins that bind to polyclonal antibodies generated against the prototype protein of SEQ ID NO:11.

Linker Molecules

The linker molecules described herein are long enough to enable reflexive binding between the nanobody and the fluorescent protein of the fusion protein. Thus, in some embodiments, the linker comprises zero to 20, zero to 15, zero to 10, or zero to nine amino acids. In some embodiments, the linker comprises from zero to 9 amino acids, e.g., zero, one, two, three, four, five, six, seven, eight, or nine amino acids. The linker can comprise natural or non-natural amino acids. In some embodiments, the linker comprises any amino acid, combinations of different amino acids, or the same amino acid. In some embodiments, the linker comprises the C-terminal amino acids of GFP. In one embodiment, the linker comprises the amino acid sequence THGMDELYK (SEQ ID NO: 10). In some embodiments, the linker comprises a subset of the amino acids of SEQ ID NO: 10.

In some embodiments, the fusion protein is a dimer, and the linker comprises zero, 1, or 3 amino acids. In some embodiments, the fusion protein is a dimer, and the linker comprises zero amino acids, the amino acid T, the amino acid sequence TH, or the amino acid sequence THG. In some embodiments, the fusion protein is a monomer, and the linker comprises 4, 5, 6, 7, 8, or 9 amino acids. In some embodiments, the fusion protein is a monomer, and the linker comprises the amino acid sequence THGM, THGMD, THGMDE, THGMDEL, THGMDELY, or THGMDELYK.

Expression Cassettes

In order to produce the fluorescent fusion proteins described herein, an expression cassette comprising a nucleic acid template can be used. The template can also used to produce proteins in cell-free systems. The templates for cell-free protein synthesis can be either mRNA or DNA. In some embodiments, the template comprises sequences that encode the fluorescent fusion proteins described herein. Nucleic acids that serve as protein synthesis templates are optionally derived from a natural source or they can be synthetic or recombinant. For example, the nucleic acid template can comprise recombinant DNAs, e.g., plasmids, viruses or the like. In some embodiments, the nucleic acid template encodes a signal sequence for inserting the fusion protein into a bacterial or eukaryotic cell membrane.

A DNA template that encodes the fluorescent fusion proteins described herein can be operably linked to at least one promoter and to one or more other regulatory sequences including without limitation repressors, activators, transcription and translation enhancers, DNA-binding proteins, etc. Suitable quantities of DNA template for use herein can be produced by amplifying the DNA in well known cloning vectors and hosts, or by polymerase chain reaction (PCR).

The expression cassette comprising the nucleic acid template is used to express the recombinant fluorescent fusion protein in a cell, or to synthesize the recombinant fluorescent fusion protein in a cell-free translation system. For example, the template can be added to a cell lysate under conditions sufficient to translate the template into protein. The cell lysate can be from bacterial cells or eukaryotic cells. The expressed protein can then be purified using methods known in the art, as described in the Examples.

EXAMPLES

Example 1

Figure 3:
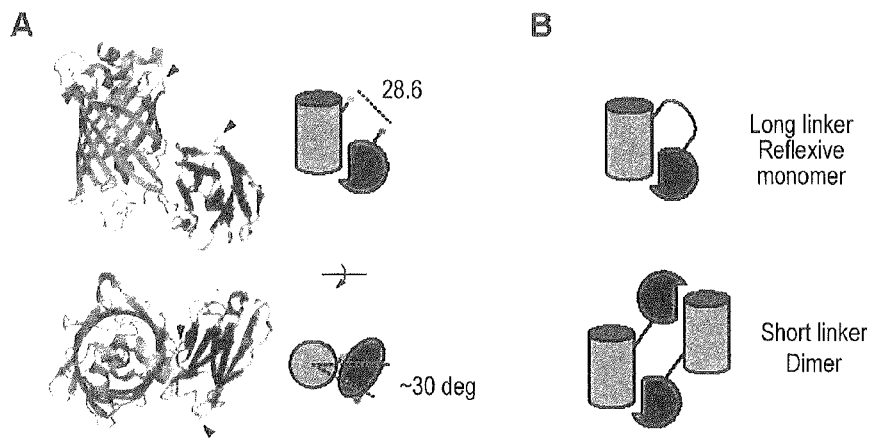
FIG. 3. Rational design to generate new variants of sfGFP. A, Binding sites of Enhancer (blue ribbon model) to sfGFP (green ribbon model) in Enhancer-sfGFP complex in two different angles. B, Schematic illustration of the genetically encoded fusion of enhancer and sfGFP to form monomer and dimer.

Results
Structure-Based Design of an Enhanced GFP Complex with Tunable Dimerization The isolation, characterization, and structure of several GFP-binding nanobodies were recently reported (33) one of which (the Enhancer, not to be confused with the "enhanced" in EGFP) confers 4-fold and 1.5-fold brighter fluorescence to wtGFP and EGFP, respectively. The crystal structure (33) indicates that the Enhancer binds to GFP on the edge of the β-barrel. We noted that the C-terminus of the GFP β-barrel terminates at a radial location that overlaps the Enhancer, but it emerges from the opposite "lid" of the β-barrel. Furthermore, we saw that the N-terminus of the Enhancer is found at a similar radial position and lies on the most proximal surface of the Enhancer to the GFP C-terminus, at a distance of 29.5 Å (C-terminal carboxyl carbon of GFP to N-terminal amino N of the enhancer) (FIG. 3A). Finally, the crystal structure of GFP, whether alone (52) or in complex with the Enhancer, does not include the C-terminal 9 amino acids, as these are unordered.

It was clear that a direct fusion of the Enhancer N-terminus to the GFP β-barrel C-terminus would be incompatible with the existing GFP-Enhancer crystal structure without drastically disrupting either the β-barrel or the Enhancer's modified immunoglobulin domain. We reasoned that the 9 unstructured C-terminal amino acids of GFP (spanning 31.5 Å if extended in a β-strand) would be sufficient to join the C-terminal residues of the GFP β-barrel to the N terminus of the Enhancer, allowing enough flexibility for the native complex to form (FIG. 3B, top). Further examination of the relative orientation of the C-terminal residues of the GFP β-barrel and the N-terminus of the Enhancer led to a second idea: direct fusion of the Enhancer to the structured C-terminus of the GFP β-barrel would enable the fused Enhancer to still interact with a second GFP molecule, and it would also leave the Enhancer binding site available on the fused GFP. Thus, we reasoned that such a direct fusion could result in a dimeric complex that would effectively contain two native complexes of GFP bound to Enhancer (FIG. 3B, bottom). As shown in FIG. 2, the 9 amino acid linker resulted in predominantly a monomeric species (FIG. 2A), whereas the 0 amino acid linker resulted in a large increase in the dimeric species (FIG. 2B), confirming our hypothesis. We refer to the direct β-barrel fusion to the Enhancer as vGFP-0, while the fusion including the 9 unstructured C-terminal amino acids of GFP is referred to as vGFP-9.

We predicted based on entropic considerations that vGFP-9, while also capable of forming a dimer, would tend to form a monomer via intramolecular binding of GFP to the linked Enhancer. This should result in a highly stable and bright monomeric fluorophore that would provide all the reported improved spectral characteristics of an enhanced GFP without the need for multiple components; in other words, it could serve as a drop-in replacement for GFP. vGFP-0, on the other hand, would theoretically have a single particle brightness of up to twice that of vGFP-9, and even greater than that of monomeric GFP. This complex would not be as versatile as vGFP-9, but in applications where dimerization is beneficial or at least not detrimental, the higher brightness would be a distinct advantage.

Construction of vGFP Variants Demonstrates Control Over Oligomeric State

Figure 12:
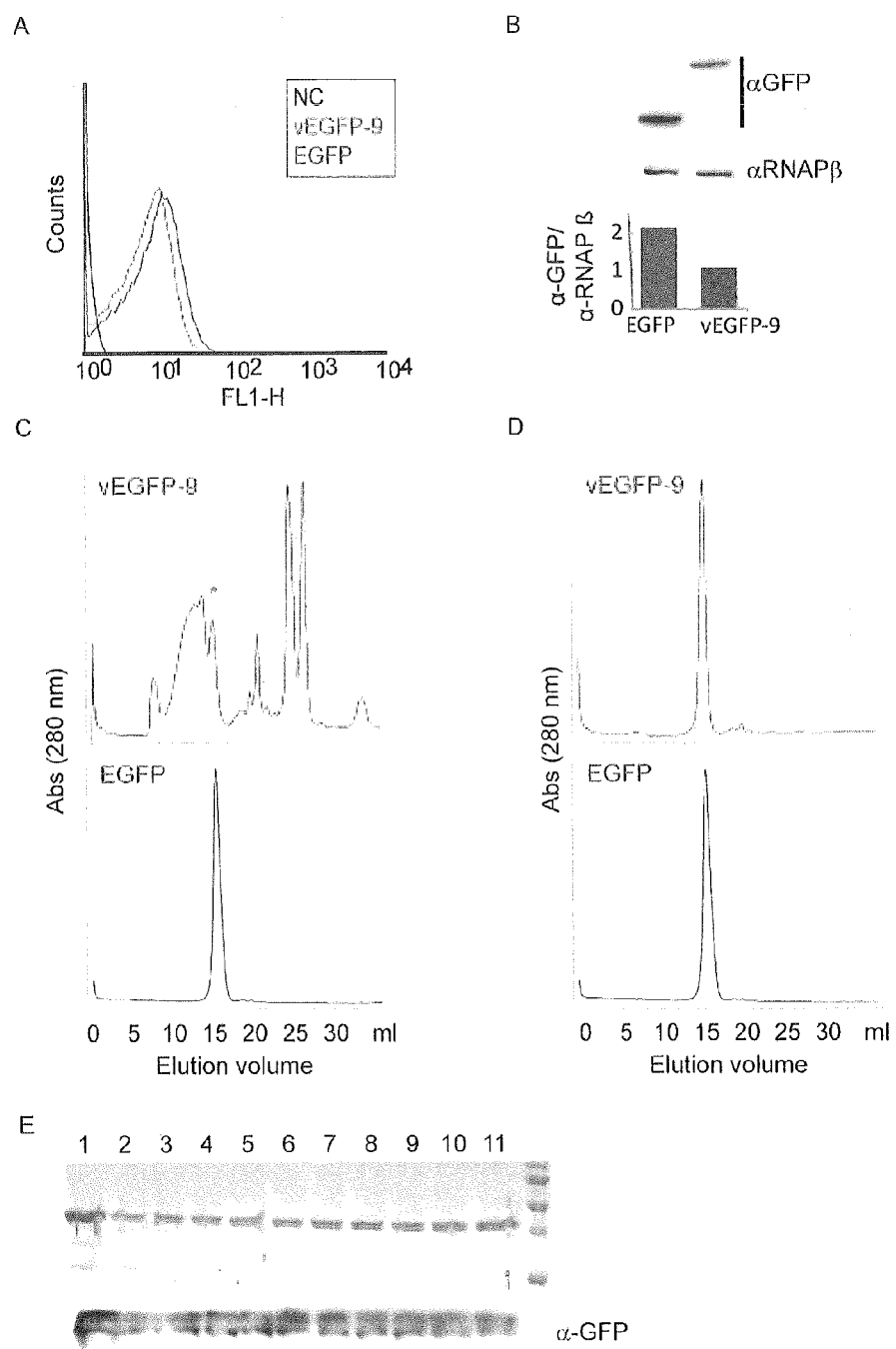
FIG. 12. vEGFP-9 is not brighter than EGFP. (A) Flow cytometry analysis of *E. coli* expressing EGFP (green) and vEGFP-9 (orange) proteins. NC, negative control (bacteria carrying empty plasmid only). For each sample a histogram of fluorescence (FL1-H) for 30,000 cells is plotted. Geometric means for NC, vEGFP, and EGFP are 1.1, 5.6, and 7.3, respectively. (B) Quantification of GFP protein levels in *E. coli*. (top) The samples in (A) were subjected to immunoblot analysis using α-GFP antibody. α-RNAP-β was used as a loading control. (bottom) Quantification of GFP levels relative to GroEL. Under the same conditions, vEGFP has lower overall protein levels which may explain its overall lower brightness compared with EGFP. (C) Gel filtration analysis of affinity purified EGFP (bottom) and vEGFP-9 (top) showing formation of aggregates by vEGFP-9. *, peak corresponding to the expected molecular weight for vEGFP-9. (D) Gel filtration analysis of the isolated fraction corresponding to the expected molecular weight of vEGFP-9 (* in panel C) with EGFP (bottom, the same sample as C bottom). As expected, these fractions contain only monomers. (E) Coomassie blue and western blot analysis of fractions from vEGFP-9 purifications. 1, sample after affinity purification; 2, samples from gel filtration chromatography corresponding to the expected size of the vEGFP-9 (* in panel C). 3 to 11, samples corresponding to fractions taken at MW higher than vEGFP-9. All samples contain the same protein band when denatured, demonstrating that the extra peaks in panel C are likely higher order oligomers or aggregates of vEGFP-9.

We initially used EGFP as the base GFP to create vGFP constructs and cloned these into E. coli BL21. The Enhancer has been shown to boost EGFP fluorescence by 1.5× (Kirchhofer NSMB). However, we saw no increase in brightness for the vEGFP constructs compared with EGFP, and in fact there was a slight decrease in brightness as measured by FACS (FIG. 12A). These initial constructs produced cytoplasmic protein; previous studies have shown that many nanobodies are unable to fold properly in the reducing cytoplasmic environment due to impaired disulfide bond formation (27, 29, 36). In keeping with this, we noted that cytoplasmic expression of both vEGFP proteins (but not EGFP itself) resulted in formation of aggregates by gel filtration chromatography (FIG. 12B). Therefore, we attached an ompA signal sequence to our constructs to express them in the periplasm. Again, however, initial examination of bacteria carrying the vEGFP constructs showed relatively low fluorescence of these constructs. As previously noted, EGFP does not fluoresce brightly in the E. coli periplasm, and while the periplasmic vEGFP proteins do fluoresce, we found that despite the ompA signal sequence, some vEGFP protein was localized to the cytoplasm (data not shown).

Therefore, we decided to create vGFP constructs using another GFP variant, sfGFP. sfGFP carries mutations from "cycle 3" GFP (48) and EGFP as well as six new mutations: S30R, Y39N, N105T, Y145F, I171V and A206V (48). These mutations improve its folding and maturation, and fusion of sfGFP to other domains can confer improved folding and stability to the fused domain (48, 50, 53, 54). Furthermore, these improvements to sfGFP folding enable it to fold properly and attain fluorescence in the bacterial periplasm (50, 51). Therefore, we reasoned that sfGFP might confer proper folding to the Enhancer nanobody in the cytoplasm as well as enable bright fluorescence of vGFP constructs in the periplasm, surmounting the problem of divergent redox requirements for fluorophore and antibody folding. We thus created vsfGFP-0 and vsfGFP-9 constructs for both cytoplasmic and periplasmic expression, along with sfGFP controls.

Figure 4:
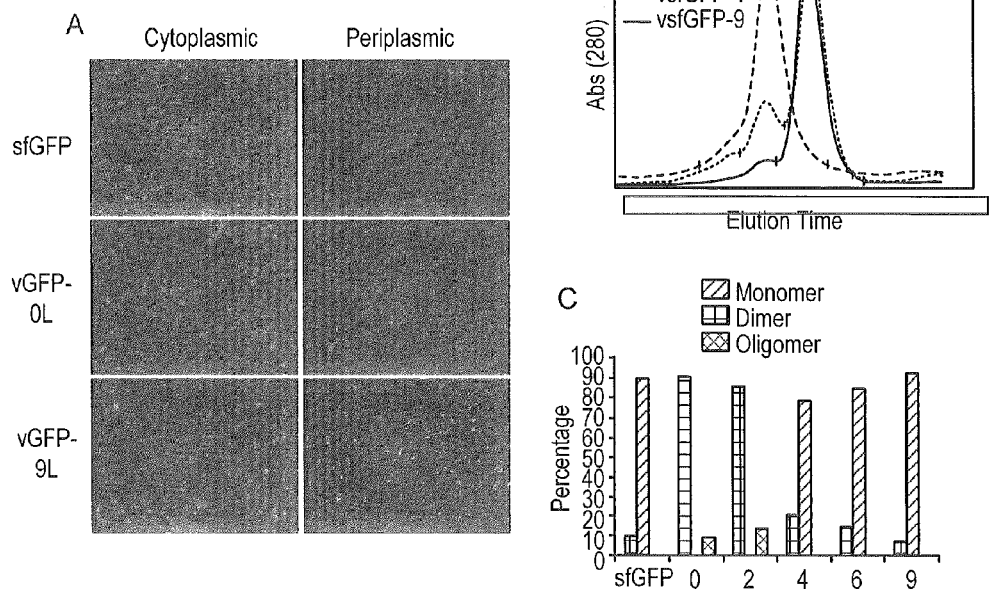
FIG. 4. Generating new sfGFP variants with different oligomeric state. A, Microscopic analysis of the bacterial cells expressing cytoplasmic and periplasmic sfGFP, vsfGFP-0 and vsfGFP-9. B, Gel filtration analysis of affinity purified sfGFP and the genetically fusion of sfGFP and enhancer with different linker size. C, Percentage of the monomer, dimer and oligomers in the gel filtration samples of sfGFP and vsfGFP-0, 2, 4, 6 and 9 amino acid linkers.
Figure 13:
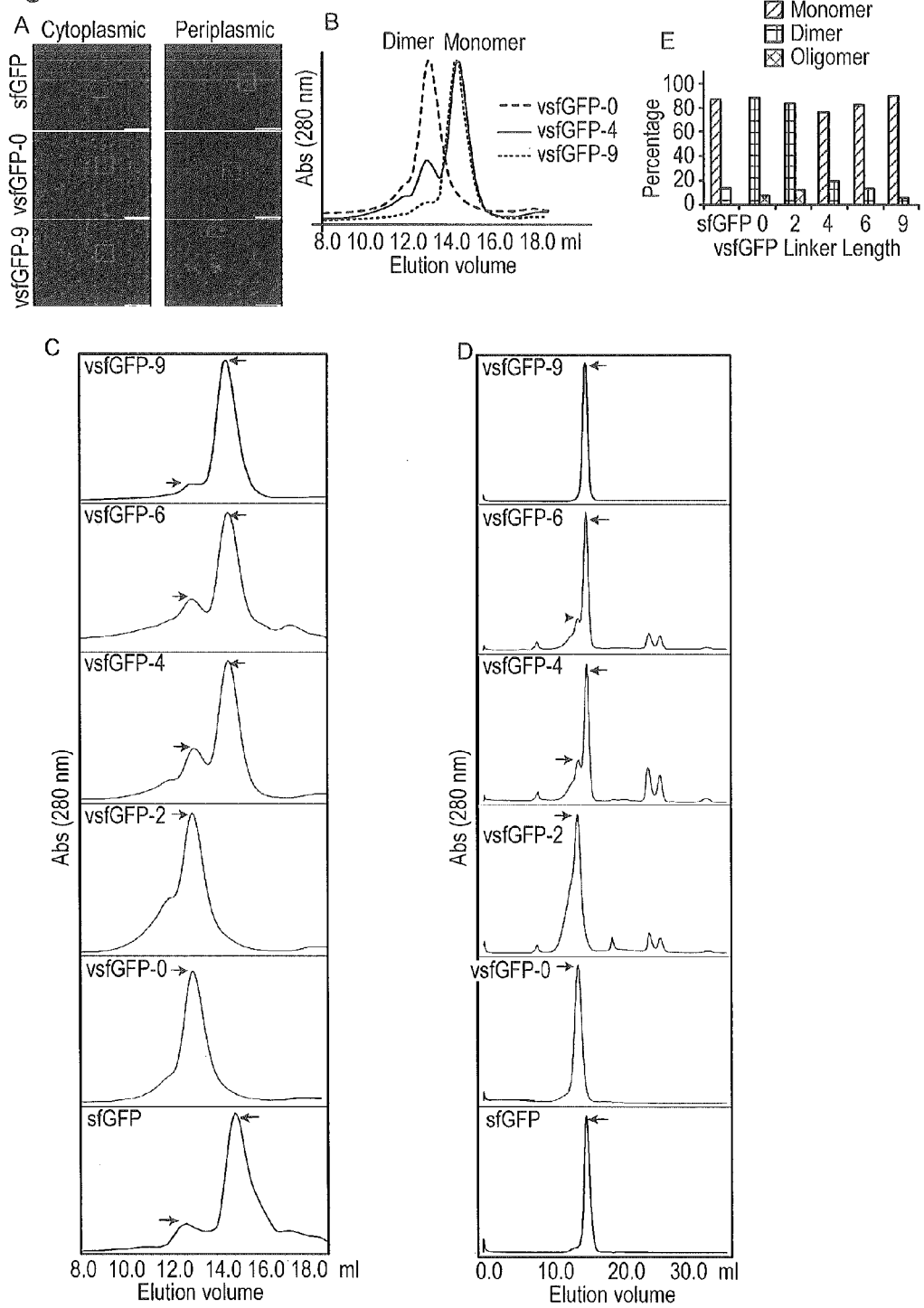
FIG. 13. Characterization of vsfGFP variants. (A) Fluorescent micrographs (100×; Scale bar, 30 μm) of *E. coli* expressing cytoplasmic (left) and periplasmic (right) sfGFP, vsfGFP-0, and vsfGFP-9. Regions boxed in green are those shown in FIG. 12C. (B) Gel filtration analysis of metal ion affinity purified vsfGFP-0 (blue), vsfGFP-4 (red), and vsfGFP-9 (green). Peaks corresponding to monomeric and dimeric proteins are indicated. (C) and (D) Gel filtration analysis of metal ion affinity purified sfGFP and vsfGFP variants with different linker sizes at two different concentrations: (C) 10 mg/mL and (D) 5 mg/ml. Peaks corresponding to monomeric and dimeric proteins are indicated by red and green arrows, respectively. (E) Percentage of monomer (green), dimer (blue), and oligomers (cyan) for vsfGFP with linkers of varying length (indicated on X axis).

We noted bright, uniform fluorescence for both the cytoplasmic vsfGFP-0 and vsfGFP-9 proteins (FIG. 4A). Metal ion affinity chromatography was used to purify them from whole cell extracts, and then we tested for the presence of higher order aggregation using gel filtration as with the vEGFP constructs. We saw a clear peak at the expected dimer size for vsfGFP-0 with no larger species, and we saw a predominant monomer peak for vsfGFP-9 with a small shoulder at a retention time corresponding to the molecular weight of a dimer (verified by SDS-PAGE) (FIG. 4B). sfGFP is known to form a weak dimer, especially at high concentrations; however, at both low and high concentrations (5 mg/mL and 10 mg/ml), the fraction of vsfGFP-9 found as a dimer was less than that of sfGFP (FIGS. 13C and D).

The vGFP design achieved tuning between monomeric and dimeric complexes by varying the linker length between the GFP and the nanobody. We chose 9 amino acids initially for the monomeric design based on the fact that GFP already contained these amino acids and that 9 aa was sufficient to span the distance between the C-terminal end of the GFP β-barrel and the N-terminal end of the bound enhancer. Based on a 3.5 Å axial Cα-Cα distance for extended β-strands (55), 9 amino acids should be the shortest linker that could span the 29.5 Å distance, assuming rigid GFP and Enhancer structures. If shorter linkers could be used, optimizing linker length might be useful for increasing protein stability (proteases tend to cleave extended unordered protein loops more efficiently) as well. We therefore created a series of vsfGFP constructs that varied in linker length from 0 to 9 amino acids. We found a monotonic increase in monomer:dimer ratio as linker length increased from 0 to 9aa, and the vsfGFP-9 construct was essentially fully monomeric (more than sfGFP itself), based on gel filtration analysis (FIGS. 4C and 13B-E). We therefore focused the rest of our studies on vsfGFP-0 and vsfGFP-9.

To further validate that the purified vsfGFP-0 and vsf-GFP-9 constructs were-indeed dimeric and monomeric, respectively, we measured their molecular weight and oligomerization state using SEC-dynamic light scattering (DLS). We measured the molecular weights of sfGFP, and vsfGFP-9 as 25140 and 39090 Daltons, respectively, in good agreement with the predicted MW based on their sequence (27604.0, and 40286.1 D). This also verified that both sfGFP and vsfGFP-9 were monomeric. In contrast, we measured a single particle MW of 78530 for vsfGFP-0, consistent with vsfGFP-0 being dimeric (predicted monomeric MW of 39210.9 D, dimeric mass 78421.8). We saw no significant aggregates in any of the samples (FIG. 13C-E).

Crystal Structure of the Dimeric vGFP Variant

Figure 5:
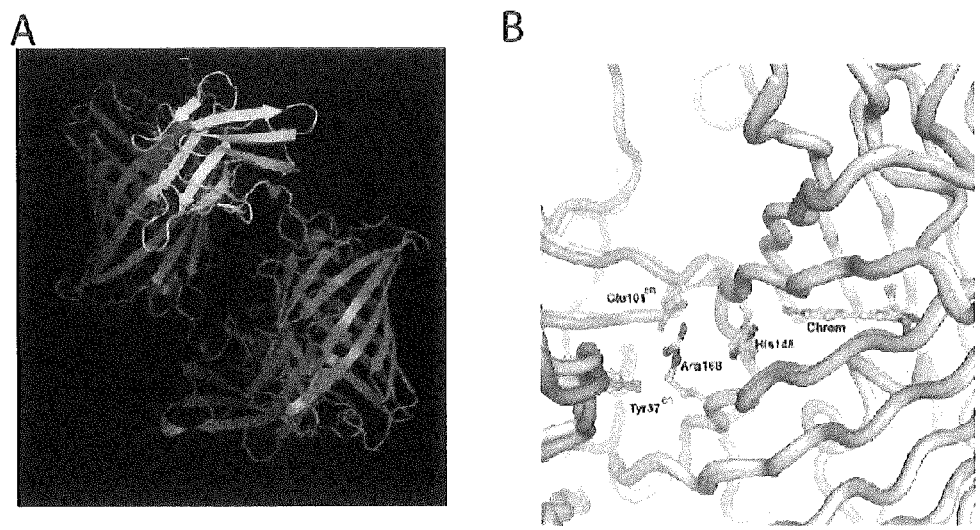
FIG. 5. Crystal structure of the dimeric sfGFP (vsfGFP-0) complex. A, Unit cell of vsfGFP-0 crystal structure showing dimeric configuration due to mutual binding of Enhancer domains to non-fused GFP domains. B, Fluorophore configuration is the same as in previously published Enhancer-GFP structure (3K1K).

To verify that our truncated linker strategy for vGFP-0 created a dimer that contained the expected Enhancer-GFP interaction, we determined the crystal structure of vsfGFP-0. Purified protein was crystallized in xx conditions, yielding a crystal that diffracted to xx Å (statistics in Table 3). Analysis of the structure showed clear electron density for the linker, verifying that a dimer between two vsfGFP-0 molecules was formed (FIG. 5A). We further examined the binding interface between the Enhancer and GFP, and found that the contacts were highly similar to that found in the Enhancer-GFP complex (FIG. 5B, Cα RMSD=xx Å) (33). Because the binding interface was preserved, we expected that the positions of key residues in the vicinity of the chromophore would also match those previously observed to be important for the enhancement of fluorescence. Looking at residues 142-148 and 168 of sfGFP (numbering based on wtGFP coordinates), we again saw a similar configuration compared with the Enhancer-GFP complex (FIG. 5B), side chain atom RMSD=xx Å). Therefore, based on the structural similarity, we expected to find an equivalent enhancement of fluorescence intensity due to the stabilization of the phenolate anion state of the GFP chromophore by Enhancer binding (33) in the vsfGFP constructs as well.

vGFP Variants Retain Enhanced Brightness Relative to GFP In Vitro

We next tested the structural prediction that the vsfGFP proteins would exhibit enhanced fluorescence. To do this, we first characterized the excitation and emission spectra of the vsfGFP-0 and vsfGFP-9 proteins. We found that both vsf-GFPs had identical excitation and emission spectra to their parental sfGFP (FIG. 6A) and that these were similar to the spectra for EGFP bound to Enhancer (33). We then proceeded to measure the brightness of each of these proteins. We first purified sfGFP, vGFP-0, and vGFP-9 to >95% purity as assessed by SDS-PAGE and gel filtration analysis. We normalized protein concentrations using both UV absorbance for aromatic amino acids and a Bradford assay. Serial dilutions of protein were assayed for relative fluorescence using a plate reader at constant illumination, and the slope of the regression between RFU and protein concentration was used as a measure of relative brightness. We found that both vsfGFP-0 and vsfGFP-9 were 1.51- and 1.58-fold brighter, respectively, than sfGFP on a molar basis (FIG. 6B).

vGFP Variants Provide Superior Brightness In Vivo

Because effective fluorescence brightness depends on the structure of the molecule as well as the cellular environment of the expressed proteins, we asked whether the newly generated variants were also brighter when expressed in living cells. As mentioned above, FACS analysis of the EGFP and vEGFP proteins expressed in bacterial cells showed that vEGFP had lower florescence intensity than EGFP (FIG. 12A), and this correlated with lower vEGFP protein levels by Western blot (FIG. 12B). This was consistent with improper folding, aggregation, and subsequent degradation of vEGFP due to the improperly folded Enhancer.

Figure 7:
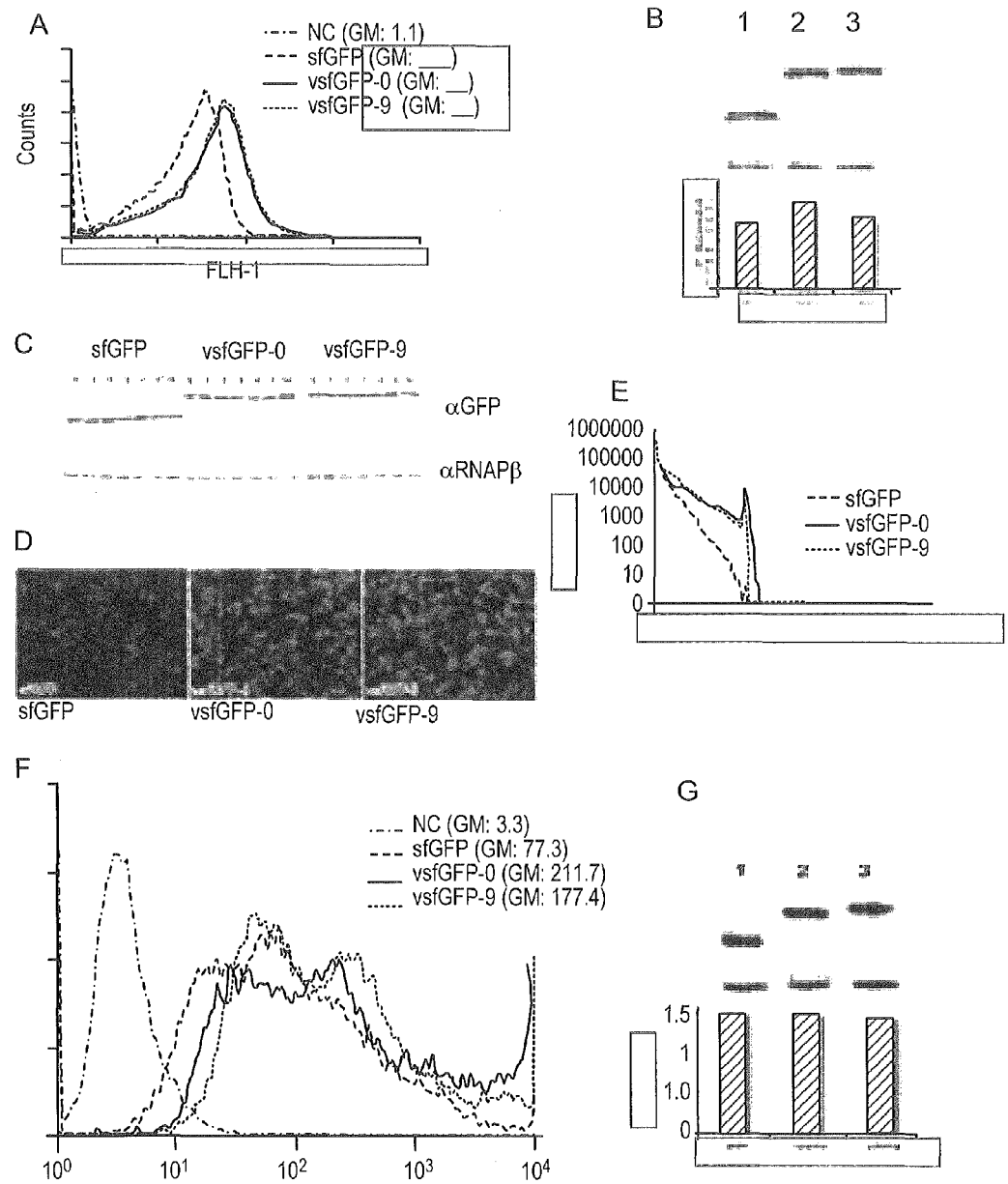
FIG. 7. In vivo brightness of the sfGFP and the new variants. A, FACS analysis of the bacterial cells expressing sfGFP, vsfGFP-0 and vsfGFP-9 proteins. B, western blot and optical density analysis of the above samples. C, Western blot analysis showing protein stability between sfGFP and the new variants vsfGFP-0 and vsfGFP-9. D, Fluorescence microscopy of 293T cells expressing sfGFP, vsfGFP-0 and vsfGFP-9 proteins. E, Intensity Histogram of images in (D). F, FACS analysis of the 293T cells expressing sfGFP, vsfGFP-0 and vsfGFP-9 proteins (NC, negative control which is the 293T cells carrying no insert vector). G, Western blot and optical density analysis of 293T cells expressing sfGFP, vsfGFP-0 and vsfGFP-9 proteins (GM, geometric mean).

We then expressed sfGFP, vsfGFP-0, and vsfGFP-9 under identical conditions in E. coli BL21 cells. By FACS analysis, we found that the median cell brightness of both vsfGFP-0 and vsfGFP-9 were 1.81 and 1.87 times higher than cells expressing sfGFP (FIG. 7A). To verify that higher brightness was due to the Enhancer and not increased expression or decreased degradation, we checked steady-state protein levels and protein degradation rates by Western blot. Under identical induction conditions, we found that full-length vsfGFP-0 and vsfGFP-9 were expressed at 1.32 and 1.10 times the level of sfGFP, leaving a brightness factor of 1.3- to 1.7-fold that could be attributed to the Enhancer (FIG. 7B). There were no visible degradation products in blots probed with α-GFP antibody, suggesting that the fluorescence we measured was due exclusively to the expected full-length proteins. To further test for the potential for protein degradation, we induced expression with 0.2% arabinose for 3 hours then switched off expression by washing the cells and resuspending them in media containing 2% glucose. We found that there was little to no visible protein degradation of sfGFP or either vsfGFP fusion (either by reduction of the full length product or appearance of smaller degradation products) over 24 hours (FIG. 7C). Therefore, neither higher vsfGFP expression levels nor additional fluorescence signal due to non-enhanced vsfGFP breakdown products could account for the brighter fluorescence levels of the vsfGFP-expressing cells.

We then asked whether the vsfGFP variants were brighter in a eukaryotic system. We cloned sfGFP, vsfGFP-0, and vsfGFP-9 under a Tet-ON expression system and transfected these constructs into 293T cells. Microscopy demonstrated that the majority of cells expressing vsfGFP-0 and vsfGFP-9 were brighter than cells expressing sfGFP at the same illumination and acquisition settings (FIG. 7D, quantified in FIG. 7E). We noticed that the fluorescence of vsfGFP-0 expressing cells was not uniform, with many highly fluorescent foci. However, the fluorescence signals from sfGFP and vsfGFP-9 were evenly distributed in the cytoplasm in all expressing cells. We further verified by FACS that individual cells expressing vsfGFP-0 and vsfGFP-9 were 2.73 and 2.50-fold brighter than cells expressing sfGFP (FIG. 7F). Western blot analysis of these cells showed no significant change in steady-state expression level of the vsfGFP variants (FIG. 7G).

vGFP Variants are Brighter than GFP on a Single Molecule Basis

Key points: 1. Molecular brightness correlates with our quantification above (i.e., 30% brighter for monomer, 160% brighter for dimer); 2. Diffusion coefficient verifies our other data above for monomer/dimer with 9/0 linker; 3. Photobleaching isn't noticeably affected. Should also note that while in vivo the brightness seems the same between vsfGFP-9/0, this is because total number of sfGFPs is the same—but on single molecule/particle analysis, one vsfGFP-0 dimer has two sfGFPs so only then appears twice as bright.

Figure 10:
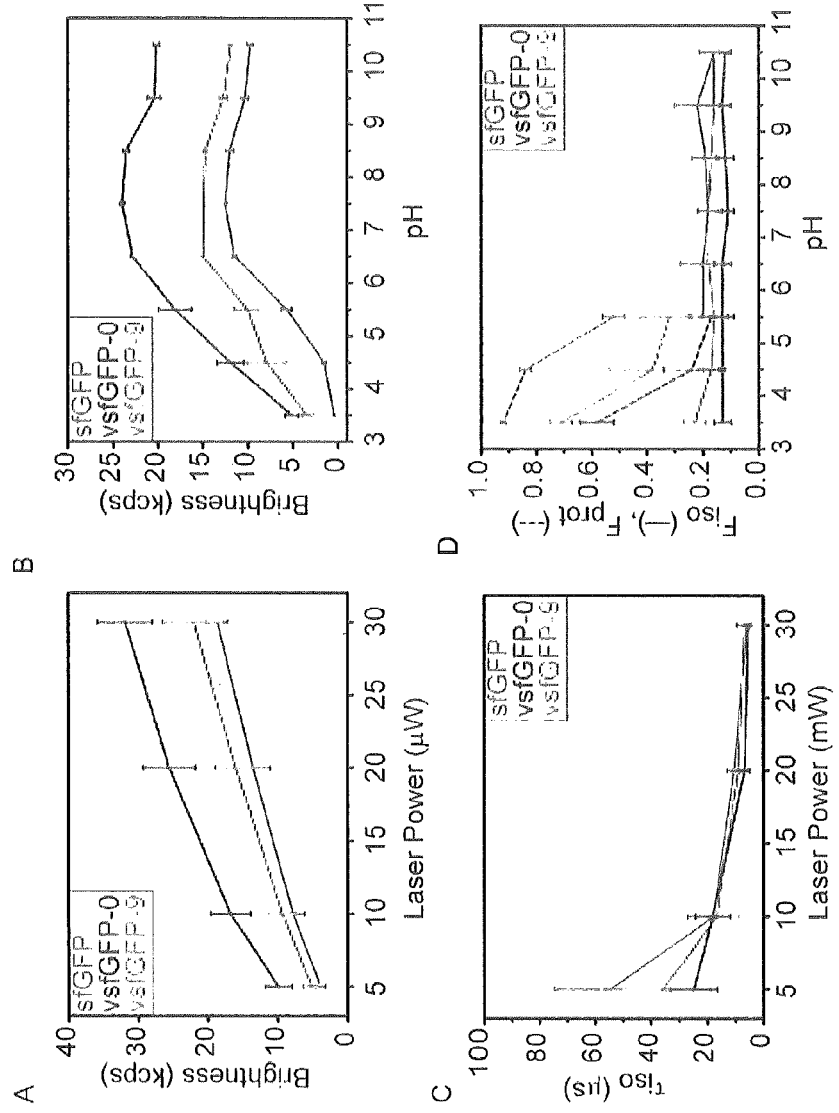
FIG. 10. FCS measurements of brightness and dark states. (A) Single particle brightness as a function of laser power at pH 7.5. (B) Single particle brightness as a function of pH at 20 uW laser power. (C) Relaxation time ($\tau_{iso}$) of the dark state from a single dark state model as a function of laser power. (D) Fraction of dark states from a model using one ($F_{iso}$, pH>5.5) or two ($F_{iso}$ and $F_{prot}$, pH<=5.5) dark states. In all panels, data is shown for sfGFP (green), vsfGFP-0 (blue), and vsfGFP-9 (red). Error bars denote standard deviation.

While our vGFP variants demonstrated higher brightness under identical expression conditions in vivo in both bacteria and human cells, we wanted to demonstrate conclusively that protein levels could not account for this increased brightness. We turned to fluorescence correlation spectroscopy (FCS), a technique that can provide single molecule brightness values as well as diffusion constants (which is related to molecular weight and oligomerization status) and some information about photostability. Using affinity and gel filtration purified samples, we measured brightness, diffusion, and photostability values for EGFP and sfGFP that were similar to published values. Again, vEGFP constructs showed similar or slightly reduced brightness compared with EGFP. vsfGFP-9 demonstrated 32.5% higher brightness on a single molecule basis compared with sfGFP at 5 $\mu W$ laser power. The diffusion coefficient was also very close to sfGFP, again verifying that the large gel filtration peak of fluorescent molecules of vsfGFP-9 are indeed monomers. vsfGFP-0 showed 154% higher brightness than sfGFP at 5 $\mu W$, with a diffusion coefficient ~30% lower than sfGFP. Both of these are consistent with our prediction that the dominant gel filtration peak of vsfGFP-0 is a dimer with twice the molecular brightness of vsfGFP-9. Photostability (as inferred from relative brightness changes as a function of laser power) was similar between vsfGFP-9 and sfGFP, while vsfGFP-0 was slightly less photostable (decreasing from a relative single particle brightness of 2.54 (at 5 $\mu W$) to 1.71 (at 20 $\mu W$) relative to sfGFP). Fraction of fluorescent fluorophores (accounting for misfolded, immature, or bleached proteins) was similar for all' sfGFP and vsfGFP proteins. Finally, as expected from the stabilization of the phenolate anion state in the presence of the Enhancer, we found that blinking rates (largely reflecting fluorophore protonation state) for the vsfGFP proteins were significantly lower than those for sfGFP (FIG. 10 and Table 1).

In summary, the nanobody fusions described herein can be used to produce fluorescent proteins that are functional in the cytoplasm and periplasm, and have brighter detection in immunostaining assays.

Discussion

Based on a careful analysis of the GFP:Enhancer crystal structure, we have devised the vGFP strategy for tuning dimerization of GFP fused with the Enhancer nanobody. These vGFP fusions retained the Enhancer-mediated fluorescence brightness boost. The monomeric vsfGFP-9 protein has similarly stability to sfGFP in vivo, provides brighter fluorescence signal in both bacteria and eukaryotes, and has slightly decreased dimerization potential in vitro. Therefore, vsfGFP-9 is an ideal candidate for an improved drop-in replacement for sfGFP in essentially all current applications. In addition, use of sfGFP in this strategy further surmounts several long standing and vexing problems for genetically encoded fluorescent antibody probes. We demonstrated that both sfGFP and the Enhancer are functional when expressed in either the reducing cytoplasm or the oxidizing periplasm of unmodified bacteria, thus providing two solutions to the problem of opposing redox requirements for folding of fluorescent proteins and nanobody antibodies.

Our initial efforts with vEGFP constructs demonstrated reduced fluorescence in the bacterial cytoplasm but reasonable (though less than expected) fluorescence in the periplasm. In the cytoplasm, EGFP is known to fold properly and fluoresce brightly. Many (but not all) nanobodies require the formation of a disulfide bond for proper folding and function, and therefore they are usually not functional when expressed in the cytoplasm of unmodified bacteria (though several exceptions have been reported) (27, 39, 42, 43). Given that higher order aggregates were observed during vEGFP purification and that vEGFP brightness was essentially similar to EGFP when corrected for expression level, it appears that the vEGFP fusion protein did not form the proper GFP:Enhancer complex and therefore showed no boost in brightness; in other words, the Enhancer was not functional when expressed in the E. coli cytoplasm. In the periplasm, EGFP is known to be very dim or non-fluorescent, while most nanobodies should readily fold into functional binding domains. Interestingly, we did see reasonable brightness when vEGFP was expressed in the periplasm, suggesting that the properly folded Enhancer was able to rescue the misfolding of EGFP in this oxidizing environment. This is one of few demonstrations of proper EGFP folding in the bacterial periplasm (24, 37) and demonstrates a novel chaperone-like function for the Enhancer protein. Nanobody binding has been shown to stabilize otherwise unordered structures, for example, enabling measurement of electron density for peptide loops during crystallography (56). Our results now demonstrate that this stabilization can influence protein folding and maturation in vivo and thus extends the potential utility of nanobodies as customizable chaperones.

Successful periplasmic expression and folding of nanobody-fluorescent protein fusions in general would provide a reasonable solution to the traditional problem of different redox requirements for the nanobody and GFP. However, cytoplasmic expression is generally superior to periplasmic expression due to higher yields and simpler purification. Previous studies have highlighted individual nanobodies that can fold in the cytoplasm (42, 44, 45). A novel solution was recently reported that used cytoplasmic expression of DsbC (a periplasmic disulfide bond isomerase) to facilitate cytoplasmic folding of nanobodies (39). By switching from EGFP to sfGFP, which is known to improve the folding reliability of fused protein domains, we found that vsfGFP-9 was monomeric and bright in both the cytoplasm and periplasm of bacteria and that this did not require any modification of the host or expression of additional proteins. Thus we have now provided two solutions to the bacterial production of nanobody-GFP fusions, including a practical, high yield, and low cost cytoplasmic strategy. Furthermore, we have now shown that sfGFP can additionally mediate the proper cytoplasmic folding of a second nanobody fused to its N-terminus. This extends the ability of sfGFP to mediate proper folding of attached domains.

Under controlled and identical expression conditions, we consistently saw higher levels of expression of the vsfGFP complexes relative to sfGFP in bacteria but not in eukaryotic cells. We examined transcription levels, but this was unable to account for these higher steady-state protein levels. Protein stability was quite high for all constructs we tested in bacteria, with negligible degradation observed over 24 hours. Since we were observing expression levels after 3 hours of induction, we therefore concluded that degradation should have little effect on protein levels during our experiment. This left the possibility that protein folding efficiency was higher for the vsfGFP fusions compared with sfGFP.

This is somewhat curious, as sfGFP, by design, already folds extremely efficiently, and the Enhancer nanobody does not fold efficiently in general in the cytoplasm (such as when fused to EGFP). Nevertheless, through quantification and correlation with in vitro bulk and single molecule measurements, we were still able to conclude that the vsfGFP variants were brighter than sfGFP. The effectively higher steady state protein levels, regardless of the underlying mechanism, are extremely useful for reporter applications using vsfGFP, particularly when examining genes or proteins with low expression. Furthermore, the apparent improved folding is certainly generally advantageous and may contribute to the success of fusing yet another nanobody to the N-terminus of the vsfGFP constructs.

We have also applied the vGFP strategy to closely related sfGFP variants, including sfYFP and sfCFP. A recent report showed that the Enhancer does not bind to CFP due to a mutation relative to GFP on the surface of the n-barrel that interacts with the Enhancer (57). However, reversion of this mutation re-establishes Enhancer binding, and sfCFP does not have this mutation. Similar brightness enhancement and tunable dimerization was observed for these vsfYFP and vsfCFP constructs. Therefore, in general, all GFP variants should be amenable to this type of fusion with the GFP Enhancer, providing an additional level of control over oligomerization and potentially increasing brightness. Due to the structural similarity of other fluorescent proteins, the vGFP strategy should also be applicable once suitable nanobodies are identified; notably, nanobodies that bind to mCherry have already been reported (45, 58). Finally, the disruption of the Enhancer:CFP complex by a single point mutation raises the possibility that a compensatory mutation(s) might be achievable in the Enhancer to restore binding to the wt CFP. This would enable several additional applications, as these could be used to design intentional heterodimers of GFP proteins by creating two vGFP-0 constructs, one containing the wt Enhancer and wt CFP (that can't be bound by wt Enhancer) and the second containing the mutated Enhancer with the mutated CFP (that can bind to wt Enhancer), for example. Combining this with N-terminal nanobody fusions would then allow rationally designed bifunctional fluorescently labeled nanobody reagents.

We have carefully measured the single molecule fluorescence of the GFP:Enhancer complex for the first time. Previous reports had only measured bulk brightness, which was rationalized based on the crystal structure of the complex (33, 57). These previous studies, while providing a reasonable explanation for the enhanced brightness, left open alternative explanations including a combination of altered protein stability, folding efficiency, extinction coefficient, and quantum yield that, when averaged over a population of molecules, resulted in an effective brightness increase of 1.5×. We have now shown that at the single molecule level, sfGFP:Enhancer complexes are indeed 1.3× brighter than sfGFP alone. Interestingly, by creating a stable dimer, we were able to calculate the fraction of sfGFP:Enhancer complexes that were fluorescent—the dimers can contain zero, one, or two fluorescing complexes, and this can be modeled with a binomial distribution. Importantly, this calculation can be done in the absence of highly accurate and precise protein quantification. We found that the fraction of bright sfGFP:Enhancer complexes was similar to previous reports for sfGFP, indicating that the Enhancer does not markedly affect overall mechanisms leading to dark sfGFP states. Therefore, we conclude that the increased brightness of individual sfGFP:Enhancer complexes is due to the previously proposed Enhancer-mediated optimization of the sfGFP fluorophore configuration, and that this enhancement (as opposed to other factors such as protein stability or folding) is responsible for the increased brightness we observe in bulk measurements in vitro as well as in bacterial and eukaryotic cells in vivo.

These in vitro, in vivo, and single molecule results are also confirmed by the crystal structure of vsfGFP-0; This structure demonstrates the overall quaternary structure we had predicted in our initial vGFP design. Furthermore, at the level of tertiary structure, the binding interface between GFP and the Enhancer and the internal configuration of the GFP chromophore environment are similar to those found in the GFP:Enhancer complex. Therefore, the increased brightness of the vsfGFP proteins is well explained by existing structural and thermodynamic studies of the GFP:Enhancer complex (33, 57).

In short, we have invented and implemented the vGFP strategy, incorporating GFP-binding nanobodies and rational structural design. We have verified that for vsfGFP, the strategy enables engineering of the oligomerization state while retaining enhanced brightness. Furthermore, vsfGFP variants provide a platform that facilitates folding of fused proteins and that is robust to redox changes. The strategy is generally applicable to other GFP variants and potentially the entire class of β-barrel fluorescent proteins. The dimerization strategy may be further generalized to other fluorescent and nonfluorescent proteins, depending on the availability of nanobodies bound in the proper orientation. Furthermore, identification of nanobodies with different relative GFP binding configurations may enable the engineering of higher order complexes that contain, for example, 4 or more GFP proteins. Thus, the vGFP strategy is a general platform for further expanding the utility and versatility of GFP and other fluorescent proteins.

TABLE 1

Summary of Fluorescence Correlation Spectroscopy (FCS) analysis of the samples in FIG. 10.

| Fluorescent Protein | Laser Power (µW) | Diffusion Time (µs) | Apparent Diffusion Coefficient (µm²/s) | Normalized Intensity | Brightness (kcpm) | Triplet Time (µs) | $F_{trip}$ (%) |
|---|---|---|---|---|---|---|---|
| EGFP | 5 | 203 ± 72 | 93 ± 26 | 0.24 | 3.18 ± 0.67 | 57 ± 64 | 28 ± 12 |
|  | 10 | 165 ± 20 | 113 ± 13 | 0.44 | 6.29 ± 0.41 | 36 ± 28 | 15 ± 4 |
|  | 20 | 148 ± 13 | 123 ± 10 | 0.76 | 11.72 ± 0.55 | 14 ± 11 | 17 ± 5 |
|  | 30 | 140 ± 7 | 128 ± 6 | 1 | 15.68 ± 0.35 | 16 ± 10 | 13 ± 2 |
| Vegfp | 5 | 171 ± 35 | 104 ± 18 | 0.23 | 3.26 ± 0.4 | 51 ± 46 | 17 ± 8 |
|  | 10 | 169 ± 33 | 113 ± 20 | 0.44 | 6.28 ± 0.7 | 36 ± 32 | 23 ± 9 |
|  | 20 | 139 ± 4 | 131 ± 4 | 0.75 | 11.91 ± 0.27 | 11 ± 10 | 18 ± 4 |
|  | 30 | 135 ± 6 | 133 ± 6 | 1 | 15.67 ± 0.32 | 7 ± 3 | 17 ± 2 |

TABLE 1-continued

Summary of Fluorescence Correlation Spectroscopy (FCS) analysis of the samples in FIG. 10.

| Fluorescent Protein | Laser Power (µW) | Diffusion Time (µs) | Apparent Diffusion Coefficient (µm²/s) | Normalized Intensity | Brightness (kcpm) | Triplet Time (µs) | $F_{trip}$ (%) |
|---|---|---|---|---|---|---|---|
| sfGFP | 5 | 181 ± 20 | 102 ± 16 | 0.24 ± 0.01 | 3.90 ± 0.71 | 33 ± 28 | 22 ± 4 |
|  | 10 | 146 ± 12 | 127 ± 9 | 0.44 ± 0.03 | 7.82 ± 1.61 | 18 ± 9 | 18 ± 3 |
|  | 20 | 137 ± 6 | 137 ± 10 | 0.76 ± 0.07 | 13.57 ± 2.84 | 10 ± 2 | 18 ± 2 |
|  | 30 | 127 ± 4 | 147 ± 5 | 1 | 18.63 ± 1.46 | 5 ± 1 | 19 ± 1 |
| vsfGFP-9 | 5 | 170 ± 22 | 103 ± 12 | 0.36 ± 0.04 | 5.17 ± 1.18 | 36 ± 17 | 15 ± 2 |
|  | 10 | 151 ± 10 | 123 ± 7 | 0.54 ± 0.03 | 9.35 ± 2.14 | 16 ± 8 | 14 ± 2 |
|  | 20 | 137 ± 11 | 134 ± 10 | 0.76 ± 0.01 | 16.03 ± 2.91 | 9 ± 3 | 17 ± 1 |
|  | 30 | 129 ± 18 | 145 ± 19 | 1 | 22.08 ± 4.36 | 7 ± 3 | 18 ± 3 |
| vsfGFP-0 | 5 | 232 ± 14 | 74 ± 4 | 0.29 ± 0.02 | 9.93 ± 1.91 | 25 ± 8 | 12 ± 1 |
|  | 10 | 213 ± 8 | 87 ± 3 | 0.49 ± 0.004 | 16.80 ± 2.86 | 18 ± 6 | 11 ± 1 |
|  | 20 | 191 ± 7 | 95 ± 3 | 0.76 ± 0.01 | 25.58 ± 3.74 | 7 ± 2 | 13 ± 2 |
|  | 30 | 179 ± 6 | 102 ± 4 | 1 | 31.94 ± 3.95 | 5 ± 0.2 | 14 ± 1 |

REFERENCES

1. Shimomura O, Johnson F H, & Saiga Y (1962) Extraction, purification and properties of aequorin, a bioluminescent protein from the luminous hydromedusan, *Aequorea*. *Journal of cellular and comparative physiology* 59(3):223-239.
2. Jones A M, Ehrhardt D W, & Frommer W B (2012) A never ending race for new and improved fluorescent proteins. *BMC biology* 10(1):39.
3. Zhang J, Campbell R E, Ting A Y, & Tsien R Y (2002) Creating new fluorescent probes for cell biology. *Nature Reviews Molecular Cell Biology* 3(12):906-918.
4. Zacharias D A & Tsien R Y (2005) Molecular biology and mutation of green fluorescent protein. *Methods of Biochemical Analysis, Green Fluorescent Protein: Properties, Applications and Protocols* 47:83.
5. Day R N & Davidson M W (2009) The fluorescent protein palette: tools for cellular imaging. *Chemical Society Reviews* 38(10):2887-2921.
6. Shaner N C, Steinbach P A, & Tsien R Y (2005) A guide to choosing fluorescent proteins. *Nature methods* 2(12):905-909.
7. Tsien R Y (1998) The green fluorescent protein. *Annual review of biochemistry* 67(1):509-544.
8. Bates M, Huang B, Dempsey G T, & Zhuang X (2007) Multicolor super-resolution imaging with photo-switchable fluorescent probes. *Science* 317(5845):1749-1753.
9. Szymborska A, et al. (2013) Nuclear pore scaffold structure analyzed by super-resolution microscopy and particle averaging. *Science* 341(6146):655-658.
10. Cabantous S p, Terwilliger T C, & Waldo G S (2004) Protein tagging and detection with engineered self-assembling fragments of green fluorescent protein. *Nature biotechnology* 23(1):102-107.
11. Casey J L, Coley A M, Tilley L M, & Foley M (2000) Green fluorescent antibodies: novel in vitro tools. *Protein engineering* 13(6):445-452.
12. Snapp E (2005) Design and use of fluorescent fusion proteins in cell biology. *Current Protocols in Cell Biology*: 21.24. 21-21.24. 13.
13. Morino K, et al. (2001) Antibody fusions with fluorescent proteins: a versatile reagent for profiling protein expression. *Journal of immunological methods* 257(1):175-184.
14. Chames P, Van Regenmortel M, Weiss E, & Baty D (2009) Therapeutic antibodies: successes, limitations and hopes for the future. *British journal of pharmacology* 157(2):220-233.
15. Rothbauer U, et al. (2008) A versatile nanotrap for biochemical and functional studies with fluorescent fusion proteins. *Molecular & cellular proteomics* 7(2):282-289.
16. Schmidthals K, Helma J, Zolghadr K, Rothbauer U, & Leonhardt H (2010) Novel antibody derivatives for proteome and high-content analysis. *Analytical and bioanalytical chemistry* 397(8):3203-3208.
17. Tang J C, et al. (2013) A Nanobody-Based System Using Fluorescent Proteins as Scaffolds for Cell-Specific Gene Manipulation. *Cell* 154(4):928-939.
18. Kirchhofer A, et al. (2009) Modulation of protein properties in living cells using nobodies. *Nature structural & molecular biology* 17(1):133-138.
19. Saerens D, Ghassabeh G H, & Muyldermans S (2008) Single-domain antibodies as building blocks for novel therapeutics. *Current opinion in pharmacology* 8(5):600-608.
20. Wesolowski J, et al. (2009) Single domain antibodies: promising experimental and therapeutic tools in infection and immunity. *Medical microbiology and immunology* 198(3):157-174.
21. Griep R A, van Twisk C, van der Wolf J M, & Schots A (1999) Fluobodies: green fluorescent single-chain Fv fusion proteins. *Journal of immunological methods* 230(1):121-130.
22. Olichon A I & Surrey T (2007) Selection of genetically encoded fluorescent single domain antibodies engineered, for efficient expression in *Escherichia coli*. *Journal of Biological Chemistry* 282(50):36314-36320.
23. Markiv A, Beatson R, Burchell J, Durvasula R V, & Kang A S (2011) Expression of recombinant multi-coloured fluorescent antibodies in gor-/trxB-*E. coli* cytoplasm. *BMC biotechnology* 11(1):117.
24. Haas A K, von Schwerin C, Matscheko D, & Brinkmann U (2010) Fluorescent Citrine-IgG fusion proteins produced in mammalian cells. *MAbs*, (Landes Bioscience), pp 648-661.
25. Luria Y, Raichlin D, & Benhar I (2012) Fluorescent IgG fusion proteins made in *E. coli*. *mAbs*, (Landes Bioscience), pp 373-384.

26. Zarschler K, Witecy S, Kapplusch F, Foerster C, & Stephan H (2013) High-yield production of functional soluble single-domain antibodies in the cytoplasm of *Escherichia coli*. *Microbial cell factories* 12(1):97.
27. Hannig G & Makrides S C (1998) Strategies for optimizing heterologous protein expression in *Escherichia coli*. *Trends in biotechnology* 16(2):54-60.
28. Schlegel S, et al. (2013) Optimizing heterologous protein production in the periplasm of *E. coli* by regulating gene expression levels. *Microbial cell factories* 12(1):24.
29. Pedelacq J-D, Cabantous S, Tran T, Terwilliger T C, & Waldo G S (2005) Engineering and characterization of a superfolder green fluorescent protein. *Nature biotechnology* 24(1):79-88.
30. Aronson D E, Costantini L M, & Snapp E L (2011) Superfolder GFP is fluorescent in oxidizing environments when targeted via the Sec translocon. *Traffic* 12(5):543-548.
31. Dammeyer T & Tinnefeld P (2012) Engineered fluorescent proteins illuminate the bacterial periplasm. *Computational and Structural Biotechnology Journal* 3.
32. Dinh T & Bernhardt T G (2011) Using superfolder green fluorescent protein for periplasmic protein localization studies. *Journal of bacteriology* 193(18):4984-4987.
33. Ormö M, et al. (1996) Crystal structure of the *Aequorea victoria* green fluorescent protein. *Science* 273(5280): 1392-1395.
34. Branden C & Tooze J (1991) *Introduction to protein structure* (Garland N.Y.).
35. Widengren J, Mets Ü, & Rigler R (1999) Photodynamic properties of green fluorescent proteins investigated by fluorescence correlation spectroscopy. *Chemical Physics* 250(2):171-186.
36. Haupts U, Maiti S, Schwille P, & Webb W W (1998) Dynamics of fluorescence fluctuations in green fluorescent protein observed by fluorescence correlation spectroscopy. *Proceedings of the National Academy of Sciences* 95(23):13573-13578.
37. Rothbauer U, et al. (2006) Targeting and tracing antigens in live cells with fluorescent nanobodies. (Translated from eng) *Nat Methods* 3(11):887-889 (in eng).
38. Loris R, et al. (2003) Crystal structure of the intrinsically flexible addiction antidote MazE. *Journal of Biological Chemistry* 278(30):28252-28257.
39. Kubala M H, Kovtun O, Alexandrov K, & Collins B M (2010) Structural and thermodynamic analysis of the GFP: GFPâ€ nanobody complex. *Protein Science* 19(12): 2389-2401.
40. Ries J, Kaplan C, Platonova E, Eghlidi H, & Ewers H (2012) A simple, versatile method for GFP-based super-resolution microscopy via nanobodies. *Nature methods* 9(6):582-584.

Example 2

Results

I. Structure-Based Design of an Enhanced GFP Complex with Tunable Dimerization

Figure 8:
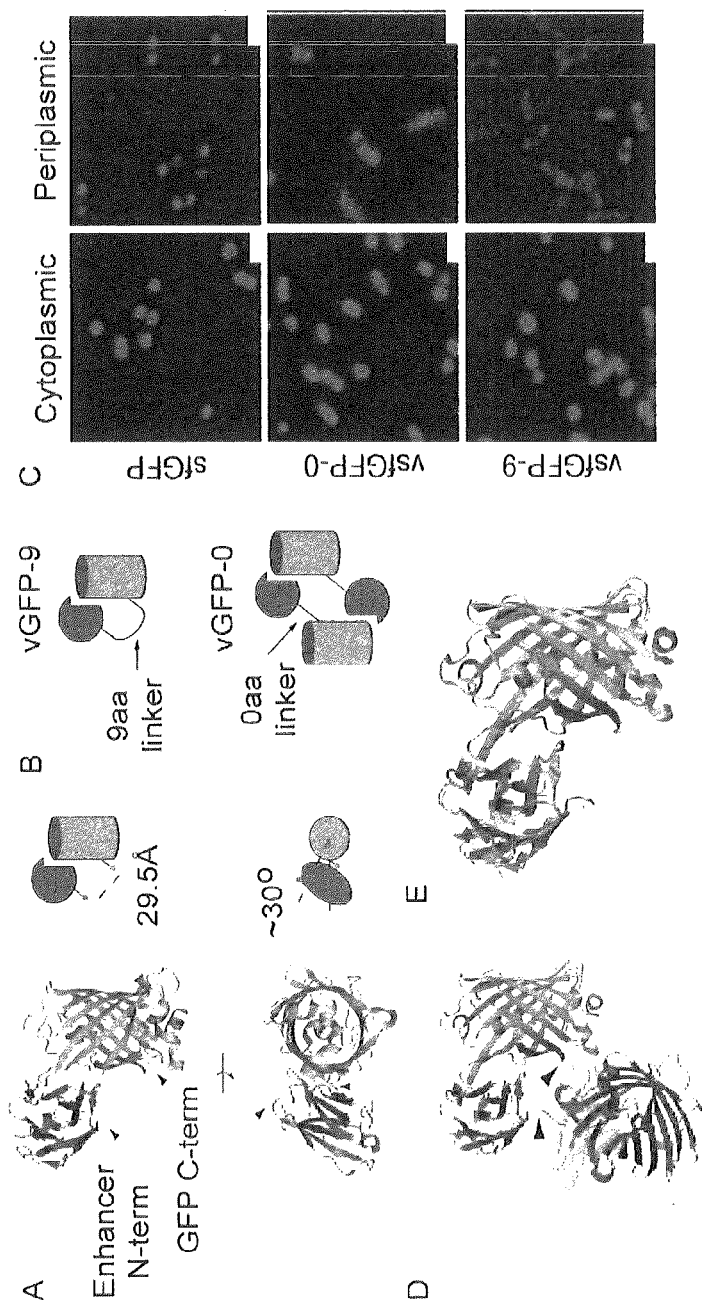
FIG. 8. The vGFP strategy for tunable dimerization. (A) (top) Crystal structure from PDB 3K1K (left) and schematic (right) of GFP (green) bound to Enhancer (red). The GFP C-terminus and the Enhancer N-terminus are indicated by arrowheads on the left and colored dots on the right. The distance between these termini is indicated. (bottom) As above but rotated by 90° about the horizontal axis. The angle between the termini is indicated. (B) Schematic of dimerization control in the vGFP fusion. (top) A 9aa linker in vGFP-9 enables reflexive binding of the Enhancer domain to the fused GFP domain. (bottom) A 0aa linker in vGFP-0 precludes reflexive binding, and thus enables formation of a dimer with two Enhancer-GFP binding interactions. (C) Fluorescence micrographs (scale bar, 2 μm) of E. coli expressing cytoplasmic (left) and periplasmic (right) sfGFP, vsfGFP-0, and vsfGFP-9. (D) Cartoon representation of the unit cell of the vsfGFP-0 crystal structure showing expected dimeric configuration. The GFP and Enhancer domains of one monomer are green and of the other monomer are red. Arrowheads indicate linkers between sfGFP and Enhancer domains. (E) Superposition of the Enhancer:GFP complex in vsfGFP-0 (green, GFP; red, Enhancer) (this study) and PDB 3K1K (cyan for both proteins).

The crystal structure of the GFP Enhancer nanobody (18) shows that the Enhancer binds to the edge of the GFP β-barrel. The crystal structure of GFP, whether alone (33) or in complex with the Enhancer, does not include the C-terminal 9 amino acids, as these are structurally flexible. We noted that the C-terminus of the ordered amino acids (Ile-229) of the GFP β-barrel emerges at a radial location that overlaps the Enhancer binding site but emerges from the opposite "lid" of the β-barrel. Furthermore, the N-terminus of the Enhancer is found at a similar radial position and lies on the most proximal surface of the Enhancer to the GFP C-terminus, at a distance of 29.5 Å (C-terminal carboxyl carbon of the ordered portion of GFP to N-terminal amino N of the Enhancer) (FIG. 8A).

A direct fusion of these two domains would be incompatible with the existing GFP-Enhancer crystal structure without drastically disrupting either the β-barrel or the Enhancer's modified immunoglobulin domain. However, we reasoned that the 9 unstructured C-terminal amino acids of GFP (assuming a 3.5 Å axial Cα-Cα distance for extended β-strands (34)) would be sufficient as a linker to allow the native complex to form (FIG. 8B, top). Further examination of the relative orientation of the C-terminal residues of the GFP β-barrel and the N-terminus of the Enhancer led to a second idea: direct fusion of the Enhancer to the structured C-terminus of the GFP β barrel would enable the fused Enhancer to interact with a second GFP molecule while leaving the Enhancer binding site available on the fused (first) GFP. Thus, we further predicted that a direct fusion would produce a dimeric complex containing two complexes of GFP bound to Enhancer (FIG. 8B, bottom). We refer to the direct β-barrel fusion to the Enhancer as vGFP-0 and to the fusion including the 9 unstructured C-terminal amino acids of GFP as vGFP-9.

Based on entropic considerations, we expected that vGFP-9, while also capable of forming a dimer, would favor formation of a monomer via intramolecular binding of GFP to the linked Enhancer. We predicted vGFP-9 would thus form a stable and bright monomeric fluorophore with the improved spectral characteristics of an enhanced GFP without the need for multiple components; in other words, it could serve as a drop-in replacement for GFP. vGFP-0, in contrast, would theoretically have a single particle brightness of twice that of vGFP-9 (and even greater compared to unenhanced GFP), providing a distinct advantage in applications where dimerization is beneficial (or not detrimental).

II. Altering Linker Length Enables Control of vGFP Dimerization

We initially used EGFP as the base GFP to create vEGFP-9. However, vEGFP-9 was less bright than EGFP itself as measured by FACS (FIG. 12A). The initial vEGFP-9 protein was expressed in the cytoplasm of *E. coli*, which may prevent proper folding of the fused Enhancer nanobody (13, 14, 20). In keeping with this, we noted lower protein levels of vEGFP-9 than EGFP (FIG. 12B) and that vEGFP-9 (but not EGFP) purified by immobilized metal ion affinity chromatography (IMAC) from the cytoplasm formed aggregates (FIG. 12C-E). Therefore, we attached an ompA signal sequence to the N-terminus of vEGFP-9 to express it in the periplasm. Again, however, vEGFP-9 showed relatively low fluorescence. EGFP itself does not fluoresce brightly in the *E. coli* periplasm (30, 31), and while the periplasmic vEGFP-9 does fluoresce, we found that despite the ompA signal sequence, some vEGFP protein was localized to the cytoplasm (data not shown).

Therefore, we switched to another GFP variant, sfGFP, that is fluorescent in the bacterial periplasm (31, 32). We reasoned that sfGFP might confer proper folding to the Enhancer nanobody in the cytoplasm as well as enable bright fluorescence of vsfGFP constructs in the periplasm, surmounting the problem of divergent redox requirements for fluorophore and antibody folding. Both vsfGFP-0 and vsfGFP-9 expressed in the cytoplasm produced bright, uniform fluorescence throughout *E. coli* (FIGS. 8C, left and 13A, left). IMAC-purified cytoplasmic vsfGFP proteins analyzed by gel filtration demonstrated a clear peak at the expected dimer size for vsfGFP-0 with no larger species and a predominant monomer peak for vsfGFP-9 with a small shoulder at a retention time corresponding to a dimer (verified by SDS-PAGE) (FIG. 13B). sfGFP is known to form a weak dimer, especially at high concentrations; however, the fraction of vsfGFP-9 found as a dimer at two high concentrations (5 mg/mL and 10 mg/ml) was lower than that of sfGFP (FIGS. 13C and D).

Figure 14:
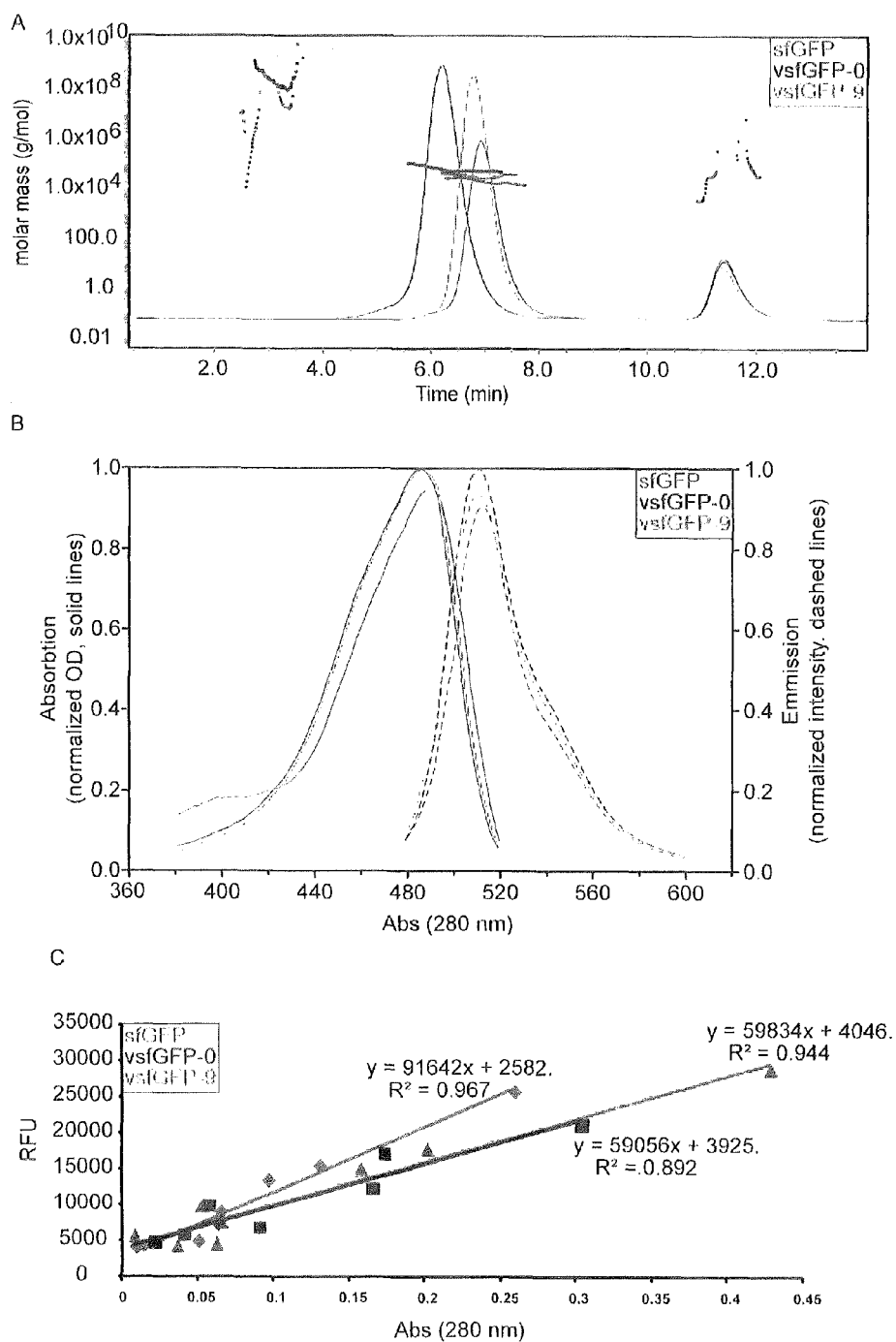
FIG. 14. In vitro biophysical characterization of sfGFP and vsfGFP variants. (A) Traces of the SEC-MALLS analysis of the sfGFP (green), vsfGFP-0 (blue), and vsfGFP-9 (red) samples showing relative protein concentrations (solid lines, arbitrary units) and measured molar masses (dots, left axis). (B) Fluorescence excitation (solid lines) and emission (dashed lines) spectra of purified sfGFP (green), vsfGFP-0 (blue), and vsfGFP-9 (red) proteins. Curves are normalized to peak absorption or emission. (C) Relative brightness of sfGFP and vsfGFP variants. Relative brightness was calculated as the slope of the regression between the fluorescence (in relative fluorescent units (RFU)) and the concentration (measured by absorption at 280 nm) of purified sfGFP (green), vGFP-0 (blue), and vGFP-9 (red) proteins. s: extinction coefficient.

The vGFP design theoretically converts between a monomer and a dimer by varying the linker length between the GFP and the Enhancer nanobody. We tested this prediction in vsfGFP and found a monotonic increase in monomer:dimer ratio as linker length increased from 0 to 9aa (FIG. 13C-E). In further support of this, we measured the molecular weights of vsfGFP-0 and vsfGFP-9 using size-exclusion chromatography with multi-angle laser light scattering (SEC-MALLS, FIG. 14A). We found that sfGFP and vsfGFP-9 were monomers (measured (predicted) molecular weights (MW) of 25140 (27604) and 39090 (40286), respectively), while vsfGFP-0 was a dimer (measured MW 78530, predicted dimeric MW 78422). Furthermore, these purified proteins all showed low levels of higher order aggregates. We therefore focused the rest of our studies on vsfGFP-0 and vsfGFP-9.

III. Crystal Structure of the Dimeric vsfGFP-0

To verify the prediction that vGFP-0 would create a dimer containing the native Enhancer-GFP interaction, we determined the crystal structure of vsfGFP-0 to a resolution of 2.60 Å (statistics in Table 3). The asymmetric unit contained two vsfGFP-0 proteins with non-crystallographic 2-fold symmetry. We found clear electron density for the linker, verifying that the expected dimer between two vsfGFP-0 molecules was formed (FIG. 8D, arrowheads). The complex between the Enhancer and sfGFP in vsfGFP-0 (each domain from a different protein) was similar to that previously reported for the Enhancer:GFP complex (FIG. 8E). We further examined the binding interface between the Enhancer and GFP, and found that the contacts were highly similar to those found in the Enhancer:GFP complex (FIG. 15A, RMSD=0.86 Å over all atoms displayed) (18). Because the binding interface was preserved, we expected that the positions of key residues in the vicinity of the chromophore would also match those in the previously published complex. Looking at residues within 4.0 Å of the chromophore, we again saw a similar configuration compared with the Enhancer-GFP complex (FIG. 15B, RMSD=0.40 Å over all atoms displayed). Therefore, given the structural similarities, we expected to find an equivalent enhancement of fluorescence intensity via the same mechanism (stabilization of the phenolate anion state of the GFP chromophore (18)) in the vsfGFP constructs as well.

IV. vsfGFP Variants Provide Superior Brightness Relative to sfGFP In Vitro and In Vivo We first tested the structural prediction that the vsfGFP proteins would exhibit enhanced fluorescence using purified proteins. We found that both vsfGFPs had nearly identical excitation and emission spectra to the parental sfGFP (FIG. 14B) and that these were similar to the spectra for EGFP bound to Enhancer (see FIG. 10b from (18)). We therefore measured relative brightness at the same excitation (488 nm) and emission (510 nm) wavelengths for all proteins. sfGFP, vGFP-0, and vGFP-9 (>95% purity as assessed by SDS-PAGE and gel filtration analysis) were adjusted to similar protein concentrations and assayed for relative fluorescence at multiple dilutions. We found that vsfGFP-0 and vsfGFP-9 had relative specific brightnesses of 1.51- and 1.58-fold higher, respectively, than sfGFP on a molar basis (Table 2 and FIG. 14C).

TABLE 2

Relative brightness of sfGFP and vsfGFP variants derived from slope of the regression between the fluorescence the concentration of purified proteins.

| Protein | MW | ε | Slope | Brightness (per mole) | Relative brightness |
|---|---|---|---|---|---|
| sfGFP | 27604 | 19035 | 91642 | 1.74E+09 | 1 |
| vsfGFP-0 | 39210.9 | 44600 | 59056 | 2.63E+09 | 1.51 |
| vsfGFP-9 | 40286.1 | 46090 | 59834 | 2.76E+09 | 1.58 |

Figure 9:
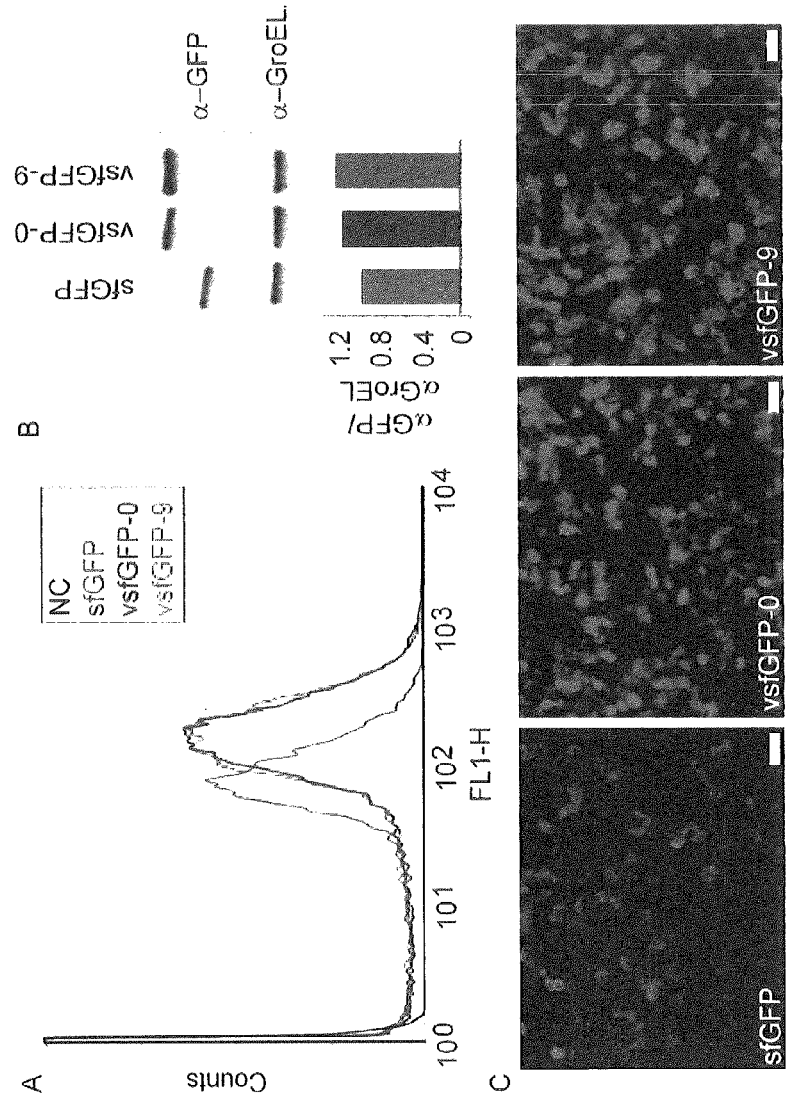
FIG. 9. In vivo brightness of the sfGFP and the vsfGFP variants. (A) Flow cytometry analysis of *E. coli* expressing sfGFP (green), vsfGFP-0 (blue), and vsfGFP-9 (red) proteins. NC, negative control (bacteria carrying empty plasmid). Geometric means for NC, sfGFP, vsfGFP-0, and vsfGFP-9 are 1, 4.86, 11.58, and 12.46, respectively. (B) Quantification of GFP protein levels in *E. coli*. (top) Immunoblot of samples from panel A using α-GFP antibody. α-GroEL was used as a loading control. (bottom) Densitometric quantification of GFP levels relative to GroEL. (C) Fluorescence micrographs (40×) of 293T cells expressing sfGFP, vsfGFP-0, and vsfGFP-9 proteins using constant illumination and capture parameters (scale bar, 20 μm).

Because effective fluorescence depends on protein structure as well as the environment in which it is measured, we next asked whether the vsfGFP proteins were also brighter in living cells. As noted above, FACS analysis of bacterial cells showed that vEGFP-9 had lower brightness than EGFP (FIG. 12A). In contrast, E. coli expressing vsfGFP-0 and vsfGFP-9 were 2.7 and 2.9 times higher, respectively, than those expressing sfGFP (FIG. 9A). To verify that higher brightness was not due to differences in expression, we checked steady-state protein levels by Western blot. Under identical induction conditions, vsfGFP-0 and vsfGFP-9 were expressed at 1.2 and 1.3 times the level of sfGFP, leaving a brightness factor of 2.25 and 2.23 fold attributed to the Enhancer (FIG. 9B). There was no visible degradation in these α-GFP blots, suggesting that fluorescence was due to full-length proteins. To further verify this, we induced expression of sfGFP, vsfGFP-0, or vsfGFP-9 in a 3 hour pulse and found no visible protein degradation over the subsequent 24 hours (FIG. 16A). Therefore, under identical conditions, vsfGFP proteins are expressed at slightly higher levels than sfGFP in E. coli but show increased fluorescence beyond the level expected from this higher expression.

We then tested the vsfGFP variants in vivo in eukaryotic cells (human 293T). The fluorescence of vsfGFP-0 within transfected cells was not uniform, with many highly fluorescent foci. However, the fluorescence signals from sfGFP and vsfGFP-9 were evenly distributed in the cytoplasm in all expressing cells (FIG. 9C). By quantitation of microscopy images taken at the same illumination and acquisition settings (FIG. 16B) and by FACS analysis (FIG. 16C), both vsfGFP-0 and vsfGFP-9 were brighter than sfGFP in 293T cells. The 2.7 and 2.3 fold higher brightness (vsfGFP-0 and vsfGFP-9, respectively) calculated by FACS again could not be explained by increased steady-state expression levels of the vsfGFP variants compared to sfGFP (FIG. 16D).

V. vGFP Variants are Brighter than GFP on a Single Molecule Basis

While the vsfGFP variants demonstrated higher brightness in vivo in both bacteria and human cells, we wanted to demonstrate conclusively that this could not be ascribed to protein levels. We turned to fluorescence correlation spectroscopy (FCS) to measure the brightness of individual vsfGFP molecules (or particles). As controls, we verified that EGFP and sfGFP proteins we purified by IMAC and gel filtration produced brightness, diffusion constant, and photostability values that were similar to published values; furthermore, as expected from nonfunctional folding of the Enhancer, purified vEGFP-9 from the cytoplasm showed similar brightness compared with EGFP (Table 1). In contrast, vsfGFP-9 demonstrated 32.5% higher brightness on a single molecule basis compared with sfGFP at 5 μW laser power (FIG. 10A). The diffusion coefficient was also close to that of sfGFP (Table 1), separately verifying that vsfGFP-9 is indeed monomeric, and that the monomers are fluorescent. vsfGFP-0 showed 154% higher brightness than sfGFP at 5 μW, with a diffusion coefficient ~30% lower than sfGFP. Both of these are consistent with vsfGFP-0 being a dimer with twice the single-particle brightness of vsfGFP-9.

We further explored whether the mechanism of enhanced brightness was due to the alteration of acid-base equilibria at the sfGFP chromophore. We considered "dark" states of GFP, which are typically caused by either photon-induced isomerization (35) or protonation of the fluorophore (36) and can be inferred from modeling of the FCS autocorrelation functions as a function of laser power or pH. We expected that, given the structural stabilization of the deprotonated phenolate anion state of the chromophore, the vsfGFP variants might be more resistant to dark states arising from chromophore protonation. Indeed, both vsfGFP constructs retained fluorescence better than sfGFP at low pH (3% residual fluorescence at pH 3.5 for sfGFP, 21% for vsfGFP-9, and 23% for vsfGFP-0; FIG. 10B). Modeling using one dark state (see methods) demonstrated a fast dark state whose relaxation time ($\tau_{iso}$) decreased at higher laser power but affected a similar fraction ($F_{iso}$) of sfGFP, vsfGFP-9, and vsfGFP-0 (Table 1, FIG. 10C). The dependence on laser power and time scale for relaxation indicated this was due to photon-induced isomerization. Modeling with two dark states at pH 3.5-5.5 extracted the same photon-induced dark state ($F_{iso}$ and $\tau_{iso}$) as well as a slower, pH-dependent dark state ($F_{prot}$ and $\tau_{prot}$) that affected a larger fraction of sfGFP than vsfGFP-9 and vsfGFP-0 particles (FIG. 10D, Table 4). The pH dependence and slow time scale led us to ascribe this second dark state to chromophore protonation. Therefore, binding of the Enhancer domain to sfGFP indeed conferred increased tolerance of fluorescence to acid pH, as expected from our and previous structural analyses.

VI. High Brightness and Tunable Dimerization Create an Attractive Platform for Molecular Probes In general, antibodies (including nanobodies) require oxidizing conditions to form disulfide bonds necessary for their function, but GFP and most derivatives do not fluoresce when expressed in oxidizing environments (30, 31). The bright fluorescence of vsfGFP-0 and vsfGFP-9 in both the reducing cytoplasm and the oxidizing periplasm of E. coli therefore suggested that fusion of antibodies to vsfGFP variants could provide a general solution to constructing fluorescently labeled antibodies. We therefore fused an anti-cytokeratin-8 (CK8) nanobody (37) to the N-terminus of sfGFP, vsfGFP-0, and vsfGFP-9, with and without periplasmic signal sequences. We found that all constructs produced brightly fluorescent bacteria (data not shown).

Figure 11:
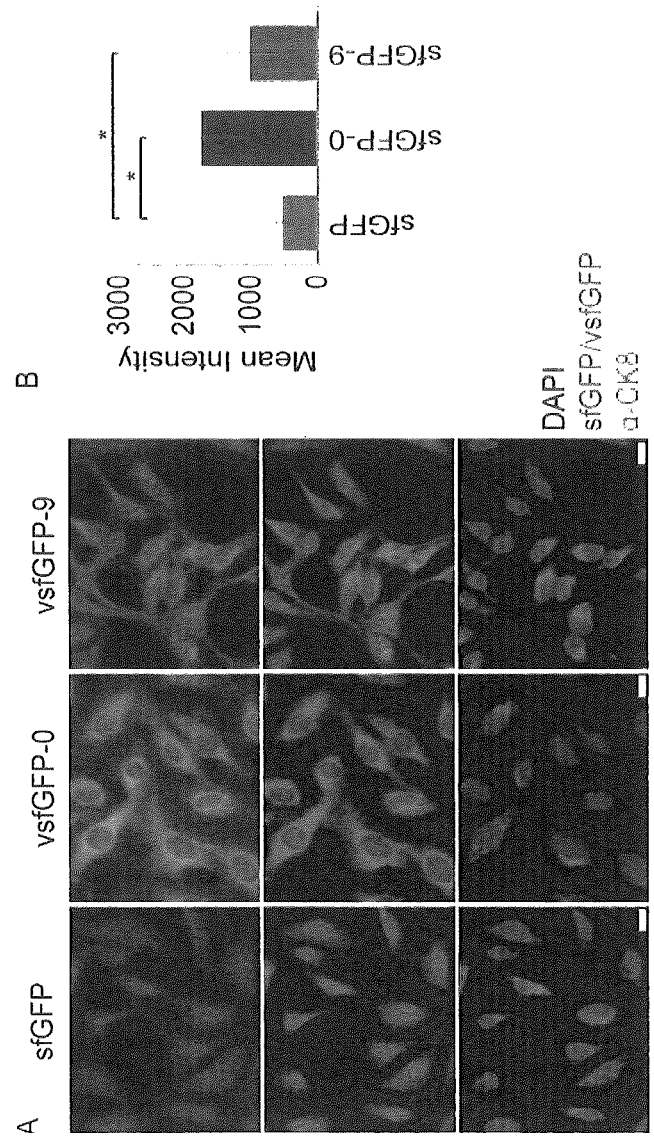
FIG. 11. vsfGFP variants outperform sfGFP as fluorophores for an antibody-based molecular probe. (A) Fluorescence micrographs (40×) of Hela cells co-stained with rabbit α-CK8 antibody (red) and an α-CK8 nanobody fused to vsfGFP-0, vsfGFP-9, or sfGFP (green). Nuclei are stained with DAPI (blue). Top, grayscale image of the green channel. Middle, merge of green (nanobody fusions) and blue (nuclei) channels. Bottom row, merge of red (rabbit α-CD8) and blue (nuclei) channels (Scale bar, 20 μm). Illumination and capture parameters were constant for all images of the green channel; illumination and capture parameters were optimized for each image of the blue and red channels. (B) Mean of raw pixel intensities in the green (nanobody fusions) channel within a 10 pixel region surrounding nuclei. Error bars represent standard deviations. *, p<0.00001 (Student's t-test).
Figure 17:
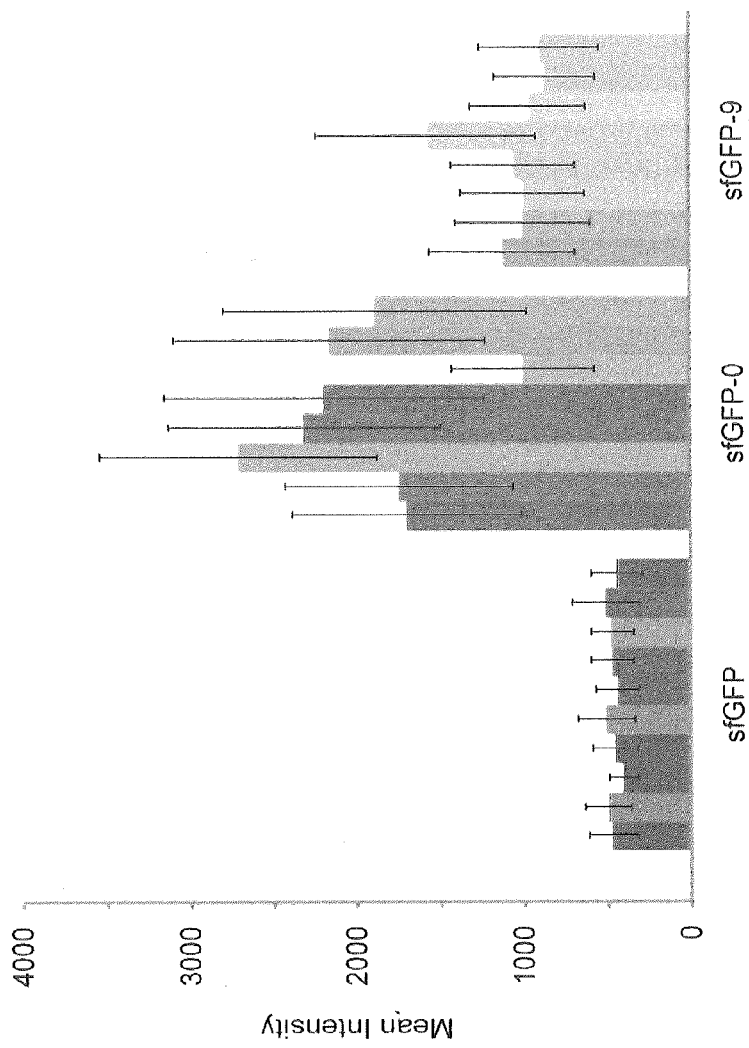
FIG. 17. Fusion to vsfGFP proteins results in brighter molecular probes than fusion to sfGFP. Quantification of multiple fields from immunofluorescence staining of Hela cells with equimolar amounts of α-CK8 fusions to sfGFP, vsfGFP-0, or vsfGFP-9. Mean signal intensity of all pixels in the green (α-CK8 fusion) within 10 pixels of nuclei (identified from the blue (DAPI) channel) of Hela cells. Error bars represent standard deviations. Each bar represents one camera field. Green channel images were acquired with the same illumination and capture parameters and pixel intensities were calculated from raw, unsealed images. The leftmost bar in each set corresponds to the data plotted in FIG. 5B.

To test whether the anti-CK8 nanobody was functional when expressed in the cytoplasm, we purified the full length cytoplasmic fusion proteins from E. coli and used equimolar concentrations to perform direct immunofluorescence staining of fixed Hela cells. Co-staining with a conventional anti-CK8 rabbit monoclonal antibody demonstrated that the sfGFP and vsfGFP fusions all properly stained cytokeratin filaments (FIG. 11A). No staining was seen with purified, unfused anti-CK8 nanobody, sfGFP, or vsfGFP proteins (data not shown). To systematically compare the brightness of staining we quantified fluorescence intensity proximal to DAPI stained nuclei and found that the anti-CK8-vsfGFP-9 fusion resulted in 2.0 fold higher signal than the anti-CK8-sfGFP fusion, while the anti-CK8-vsfGFP-0 fusion resulted in a further 1.7 fold increase (FIG. 11B and FIG. 17). Therefore, the vsfGFP constructs enable convenient and economical production of functional, fluorescently labeled nanobodies in the cytoplasm of E. coli that provide up to 3.4 fold times the signal of the equivalent sfGFP-labeled nanobodies.

Discussion

Based on an analysis of the Enhancer:GFP crystal structure, we have devised the vGFP strategy for tuning the dimerization of GFP by fusion with the Enhancer nanobody, creating both monomeric (vGFP-9) and dimeric (vGFP-0) forms. vsfGFP fusions retain the Enhancer-mediated brightness boost. The monomeric vsfGFP-9 has similarly stability to sfGFP in vivo, provides brighter fluorescence signal in both bacteria and eukaryotes, and has slightly decreased dimerization in vitro. Therefore, vsfGFP-9 is an ideal drop-in replacement for sfGFP in essentially all current applications. In addition, use of sfGFP in the vGFP strategy surmounts a vexing problem for genetically encoded fluorescent antibody probes. When fused in a vsfGFP construct, both the sfGFP and Enhancer domains are functional in either the reducing cytoplasm or the oxidizing periplasm of unmodified bacteria, providing two solutions to the problem of opposing redox requirements for folding of fluorescent proteins and nanobodies.

Our initial efforts with vEGFP-9 demonstrated reduced fluorescence compared with EGFP itself in the bacterial cytoplasm but reasonable (though less than expected) fluorescence in the periplasm. In the bacterial cytoplasm, EGFP is known to fold properly and fluoresce brightly. Many nanobodies require the formation of a disulfide bond for proper folding and function, and therefore they are not functional when expressed in the cytoplasm of unmodified bacteria (though several exceptions have been reported) (13, 22-24). Given that higher order aggregates were observed during vEGFP-9 purification and that vEGFP-9 brightness was essentially similar to EGFP when corrected for expression level, it appears that the vEGFP-9 fusion protein did not form the proper Enhancer:GFP complex and therefore showed no boost in brightness; in other words, the Enhancer was not functional when expressed in the E. coli cytoplasm. Indeed, the GFP-binding Enhancer contains two cysteines, and we suspect that these must form a disulfide bond to enable Enhancer function. In the periplasm, EGFP is very dim or non-fluorescent, while most nanobodies readily fold into functional binding domains. Interestingly, the brightness of vEGFP-9 in the periplasm, suggests that the properly folded Enhancer might rescue the misfolding of EGFP. This is one of few demonstrations of proper EGFP folding in the bacterial periplasm (11, 21) and demonstrates a novel chaperone-like function for the Enhancer. Nanobody binding has been shown to stabilize otherwise unordered structures, for example, enabling measurement of electron density for peptide loops during crystallography (38). Our results now demonstrate that this stabilization can influence protein folding and maturation in vivo and thus extends the potential utility of nanobodies as customizable chaperones.

Expression and folding of nanobody-fluorescent protein fusions in the periplasm in general would provide a reasonable solution for producing fluorescently labeled antibodies. However, cytoplasmic expression is generally superior due to higher yields and simpler purification. Previous studies have highlighted individual nanobodies that can fold in the cytoplasm (23, 25, 26). An alternative solution using cytoplasmic expression of DsbC (a periplasmic disulfide bond isomerase) to facilitate cytoplasmic folding of nanobodies was recently reported (22). In contrast to vEGFP-9, vsfGFP-9 was monomeric and bright in the cytoplasm of bacteria, indicating proper Enhancer folding without modification of the host or expression of additional proteins. Furthermore, fusion of a second nanobody to vsfGFP-0 or vsfGFP-9 resulted in functional, fluorescent molecular probes that are superior (up to 3.4 fold higher) in brightness to sfGFP fusions. Our results demonstrate that sfGFP can mediate the proper cytoplasmic folding of two separate nanobodies fused to its N- and C-terminus and also validate a practical, low cost, cytoplasmic strategy for creation of fluorescently labeled antibodies.

We have also applied the vGFP strategy to the sfGFP variants sfYFP and sfCFP. The Enhancer does not bind to wtCFP due to a mutation relative to wtGFP on the surface of the β-barrel that interacts with the Enhancer (39), but sfCFP does not have this mutation. Similar brightness enhancement and tunable dimerization were observed for vsfYFP and vsfCFP constructs (data not shown). Therefore, in general, all GFP variants should be amenable to the vGFP strategy, providing an additional level of control over oligomerization and potentially increasing brightness.

We have carefully measured the single molecule fluorescence of the Enhancer:GFP complex for the first time. Previous reports had only measured bulk brightness, which was rationalized based on the crystal structure of the complex (18, 39). These previous studies, while providing a reasonable explanation for the enhanced brightness, left open alternative explanations including a combination of altered protein stability, folding efficiency, extinction coefficient, and quantum yield that, when averaged over a population of molecules, resulted in an effective brightness increase of 1.5×. We have now shown that at the single molecule level, Enhancer:sfGFP complexes are indeed 1.3× brighter than sfGFP alone. Therefore, we conclude that the increased brightness of individual Enhancer:sfGFP complexes is due to the previously proposed Enhancer-mediated optimization of the GFP fluorophore configuration (18), leading to the increased brightness we observe in bulk measurements in vitro as well as in bacterial and eukaryotic cells in vivo.

These in vitro, in vivo, and single molecule results are confirmed by the crystal structure of vsfGFP-0. This structure demonstrates the overall quaternary structure we had predicted in our initial vGFP design. Furthermore, the binding interface between sfGFP and the Enhancer and the internal configuration of the sfGFP chromophore environment are similar to those found in the Enhancer:GFP complex. Therefore, the increased brightness of the vsfGFP proteins is well explained by existing structural and thermodynamic studies of the Enhancer:GFP complex (18, 39).

The stabilization of the phenolate anion, and thus the 7-fold decrease in pH sensitivity, by the Enhancer occurs through the imposition of constraints from outside the GFP β-barrel impacting the local chromophore environment within the β-barrel. The use of a nanobody or other GFP-binding protein to modify the fluorescence properties of GFP suggests a novel strategy for future improvements of GFP or other fluorescent proteins. Mutations in the GFP protein itself may not be able to access the entire range of constraints possible with external binding proteins; therefore, mutagenesis of GFP complexes with other proteins may prove to be a fruitful strategy for further modification of desirable GFP properties. Indeed, this strategy for improving GFP represents an engineered analog of allosteric control of enzymatic or other protein function by separate regulatory domains.

In short, we have invented and implemented the vGFP strategy, incorporating GFP-binding nanobodies and rational structural design. We have verified that for vsfGFP, the strategy enables control of oligomerization state while retaining enhanced brightness. Furthermore, vsfGFP variants provide a platform that facilitates folding of fused proteins and that is robust to redox environment. The strategy is applicable to other GFP variants and potentially may be further generalized to other fluorescent and nonfluorescent proteins, depending on the availability of appropriate binding proteins. Furthermore, identification of nanobodies with different relative GFP binding configurations may enable the engineering of higher order complexes that contain, for example, 4 or more GFP proteins. Thus, the vGFP strategy further expands the utility and versatility of GFP and other fluorescent proteins.

Experimental Procedures

Plasmid Construction.

All nanobody proteins were codon optimized for *E. coli* and synthesized by DNA 2.0 (Menlo Park, Calif., USA). All plasmids used in this study are listed in Table 5. All primers used for cloning in this study were purchased from Sigma (Singapore) and are listed in Table 6. Genes encoding the Enhancer (GFP binding protein) (1) and cytokeratin 8 nanobodies (CK8) (2) were codon optimized using Gene Designer (3) and synthesized by DNA 2.0 (Menlo Park, Calif., USA). DNA encoding fluorescent proteins and fluorescent protein nanobodies were cloned into XbaI and HindIII restriction sites of the pBAD33 under the L-arabinose-inducible $P_{araB}$ promoter and expressed in *E. coli* BL21(DE3) (Novagen, Billerica, Md., USA). Amplification of all fragments was performed using Phusion Hot Start II High Fidelity DNA Polymerase (Thermo Scientific, Singapore) with initial denaturation for 2 min at 98° C. followed by 30 cycles of denaturation (98° C., 10 s), annealing (60° C., 30 s), and extension (72° C., 1 min) with final extension for 5 minutes at 72° C. Standard reactions contained 1× Phusion High-Fidelity PCR master mix with HF buffer (NEB, Singapore), 1 ng template plasmid, 0.2 mM dNTP mix (NEB, Singapore), and 0.1 µM of each primer pair.

The gene encoding sfGFP was amplified by PCR from plasmid pSLC-114 using primer pair P1-P2 containing the restriction sites for XbaI and HindIII. The amplified fragment was digested and cloned into pSLC-6 using XbaI and HindIII restriction sites to give the plasmid pSLC-253.

Overlapping PCR was used to generate DNA fragments encoding vGFP variants (vsfGFP-0, vsfGFP-2, vsfGFP-4, vsfGFP-6 and vsfGFP-9). The primer pairs P4-P5, P6-P7, P8-P9, P10-P11, P12-P13 were used to amplify DNA encoding sfGFP and Enhancer from pSLC-253 and pSLC-252 plasmids, respectively. A second. PCR was carried out to stitch together the above fragments using primer pairs P1-P3. The overlapping PCR products were then digested and cloned into pSLC-6 using XbaI and HindIII restriction sites to produce vGFP constructs (pSLC-254, pSLC-151, pSLC-152, pSLC-153, and pSLC-255).

The ompA signal sequence was to direct periplasmic expression of the sfGFP, vsfGFP-0, and vsfGFP-9 genes. The primer pair P14-P15 containing the restriction sites for XbaI and NdeI was used to amplify the ompA signal sequence from plasmid pSLC-252. The amplified fragment was digested and inserted into the XbaI and NdeI restriction sites of plasmids pSLC-253, pSLC-254, and pSLC-255 to generate plasmids pSLC-256, pSLC-257, and pSLC-258.

A DNA fragment encoding EGFP was generated from plasmid pEGFP-C1 (Clontech, Singapore) with the primer pair P16-P17 containing the restriction sites for XbaI and HindIII. The amplified fragment was digested and cloned into pBAD33 using XbaI and HindIII restriction sites to give plasmid pSLC-259.

Overlapping PCR was used to generate a gene encoding vEGFP-9 by amplifying EGFP with primer pair P16-P19 from pSLC-259 and amplifying the Enhancer with primer pair P18-P20 from pSLC-252. Subsequently, the above fragments were joined together with primer pair P16-P20 to generate a gene encoding vEGFP-9. This fragment was digested with XbaI and HindIII restriction enzymes and cloned into pSLC-6 to generate pSLC-260.

The ompA signal sequence was amplified from pSLC-252 with primer pair P14-P15 containing restriction sites for XbaI and NdeI. The amplified fragment was digested and inserted into pSLC-259 and pSLC-260 using XbaI and NdeI restriction sites to give plasmids pSLC-261 and pSLC-262, respectively.

Genes encoding sfGFP, vsfGFP-0, and vsfGFP-9 were amplified with primer pair P21-P22 from plasmids pSLC-253, pSLC-254, and pSLC-255, respectively. The amplified fragments were digested with EcoRI and cloned into the pSLC-209 EcoRI restriction site to generate the plasmids pSLC-263, pSLC-264, and pSLC-265.

An α-CK8 nanobody was fused to the N-terminal end of the sfGFP, vsfGFP-0, and vsfGFP-9 proteins (using a linker with the sequence SGSGSGSGSG (SEQ ID NO: 21)) for molecular probe production. DNA encoding the CK8 nanobody was amplified from pSLC-266 with primer pair P23-P25 and DNA encoding sfGFP, vsfGFP-0, and vsfGFP-9 fragments were amplified with primer pair P26-P24 from pSLC-253, pSLC-254, and pSLC-255 respectively. The above fragments were joined together with a second PCR with primer pair P23-P24 to give CK8-sfGFP, CK8-vsfGFP-0, and CK8-vsfGFP-9. The above fragments were cloned into pSLC-6 using XbaI and HindIII restriction sites to produce plasmids pSLC-267, pSLC-268, and pSLC-269.

For periplasmic expression of CK8-sfGFP, CK8-vsfGFP-0, and CK8-vsfGFP-9, the ompA signal sequence was amplified from pSLC-252 with primer pair P14-P15 containing the restriction sites for XbaI and NdeI. The amplified fragment was digested and inserted into pSLC-267, pSLC-268, and pSLC-269 using XbaI and NdeI restriction sites to give the plasmids pSLC-270, pSLC-271, and pSLC-272, respectively.

Bacterial Culture Conditions.

Lysogeny broth (LB, Life Technologies, Singapore) medium supplemented with glucose was used to repress expression of proteins during routine cloning and growth. LB medium supplemented with 0.2% arabinose was used to induce expression for flow cytometry, immunodetection of proteins, and microscopic analysis. For flow cytometry and protein analysis, E. coli BL21 (DE3) cultures were first grown aerobically at 37° C. in LB supplemented with 2% glucose. Prior to induction, the cells were harvested by centrifugation, washed twice with phosphate-buffered saline (PBS, pH 7.4), and resuspended in LB medium supplemented with 0.2% arabinose. For protein purification, E. coli BL21 (DE3) cultures were grown aerobically at 18° C. in LB medium and induced with 0.05% arabinose.

Flow Cytometry Analysis.

E. coli BL21 (DE3) carrying sfGFP, vsfGFP-0, or vsfvGFP-9 expressing plasmids were grown in lysogeny broth (LB) supplemented with 2% glucose. After 3 hours of induction in LB supplemented with 0.2% arabinose, cultures were harvested and resuspended in PBS to an OD of 0.1 at 600 nm. Transfected 293T cells were harvested by trypsinization, inactivated with culture media, then collected by centrifugation and resuspended in PBS. Flow cytometry analysis for GFP expression was performed on a FACSCalibur (Becton Dickinson, San Jose, Calif.).

Time Course Analysis of GFP Expression for Protein Stability Analysis.

Strains carrying sfGFP or vsfGFP constructs in E. coli BL21 (DE3) were induced with 0.2% arabinose for 3 hours in LB medium. The cells were harvested, washed twice with PBS, and resuspended in LB medium supplemented with 2% glucose for 24 hours. Samples were collected at 0, 3, 8 and 24 hours and analyzed by immunoblotting.

Protein Purification.

E. coli BL21 (DE3) cells were harvested by centrifugation at 10,000×g for 10 min at 4° C. before being treated with TN buffer (50 mM Tris-HCl pH 7.4, 300 mMNaCl) supplemented with 10 mM imidazole and cOmplete Protease Inhibitor Cocktail (Roche, Singapore). Cells were sonicated using alternating 2 second on and off cycles for 10 min at 40% power at 4° C. using a Branson Sonicator (Thomas Scientific). The resulting lysate was centrifuged at 20,000×g for 1 hour at 4° C. The supernatant was filtered through 0.2 μm filtration system and used for purification of His-tagged proteins using metal affinity chromatography. Proteins were eluted with 300 mM imidazole. This eluate was loaded onto a Superdex 200 gel filtration column (GE Healthcare, Singapore) installed on an ÄKTApurifier (GE Healthcare, Singapore). The column was pre-calibrated with Bovine Lung Aprotinin (6,500 D) Horse Heart Cytochrome C (12,400 D), Bovine Erythrocytes Carbonic Anhydrase (29,000 D), Bovine Serum Albumin (66,000 D), Yeast Alcohol Dehydrogenase (150,000 D), and Blue Dextran (all from Sigma, Singapore) in TN buffer with a flow rate of 0.5 or 1 mL/min with 1 mL fractions.

Excitation and Emission Spectra Scanning.

Fluorescence excitation and emission spectra were recorded SpectraMax M2 spectrophotometer (Molecular Devices, Sunnyvale, Calif., USA). Samples were diluted to 15 μM in 1× TN buffer at various pH values. Excitation spectra were measured using emission at 520 nm. Emission spectra were measured using excitation at 480 nm. Steps were set to 2 nm. Data analysis was performed using Microsoft Excel.

Measurement of Bulk Relative Brightness.

The concentrations of proteins in solution were quantified by UV absorption at 280 nm and Bradford assay (Bio-Rad, Singapore) (all values were within 20% of each Other). The concentrations of sfGFP, vGFP-0, and vGFP-9 were normalized using TN buffer, which was also used as a negative control. Serial dilutions of protein samples were assayed for relative fluorescence (RF) with a SpectraMax M5 Microplate Reader (Molecular Devices, Sunnyvale, Calif.) using Optiplex 96 F microtitre plates (PerkinElmer, UK) at excitation and emission wavelengths of 490 nm and 510 nm, respectively. The slope of the regression between RFU and UV absorption was used to calculate relative brightness.

Transfection.

293T cells were grown in Dulbecco's minimal essential medium (DMEM) supplemented with 10% fetal calf serum (FCS) and 2 mM glutamine. For transient expression of sfGFP and vGFP, 293T cells (2×10$^5$ cells/well) were seeded in 6-well microplate, grown to 80% confluence, and washed with Opti-MEM serum-free medium (Life Technologies, Singapore), then 0.5 mL of Opti-MEM serum-free medium was added. Next, Lipofectamine 2000 (10 μl/well, Life Technologies, Singapore) was mixed with 250 μl of Opti-MEM serum-free medium. 2.5 μg of each pTetO plasmid construct (pSLC-263, pSLC-264, or pSLC-265) was mixed with 2.5 μg of FUW-M2rtTA in 250 μl of the same medium followed by incubation for 20 mM at room temperature. The above mixtures were added to the cells and incubated for 16 h at 37° C. prior to replacement with serum-containing medium supplemented with 0.5 μg/ml Doxycycline (Sigma, Singpaore) for induction. The cells then were subjected to flow cytometry and microscopic analysis. Images were taken with a Zeiss Cell Observer microscope with a 40× objective using AxioVision software. Images were analyzed using ImageJ (National Institutes of Health) and Adobe Photoshop® CS2.

Immunofluorescence Analysis.

Hela cells were grown and maintained in Dulbecco's minimal essential medium (DMEM) supplemented with 10% fetal calf serum (FCS) and 2 mM glutamine. For immunofluorescence staining, Hela cells were cultured on Millicell EZ SLIDE 8-well glass slides (Millipore, Singapore) at a density of 4×10³ cells per well and cultured overnight at 37° C. in a 5% CO2 atmosphere. Cells were fixed with 100% methanol at −20° C., washed once with PBS, permeabilized with 0.2% Triton X-100 in PBS for 10 mM, washed twice with PBS, and blocked with 10% FBS in PBS for 1 hour. The fixed and permeabilized cells were incubated with CK8-sfGFP, CK8-vsfGFP-0, or CK8-vsf-GFP-9 (each at 400-500 nM). The cells were co-stained with CK8 Rabbit monoclonal antibody (1:100, Abcam, San Francisco, Calif., USA) followed by Alexa Fluor® 594 Goat Anti-Rabbit (1:500; Molecular Probes). Nuclei were visualized by 4,6-diamidino-2-phenylindole staining (DAPI; 0.02 ug/ml). Images were captured with a Zeiss Cell Observer microscope with a 40× objective using AxioVision software. Images were analyzed using ImageJ (National Institutes of Health, Bethesda, Md.) and Adobe Photoshop® CS2.

For bacterial microscopic analysis, images were taken with a Zeiss Axiovert 200M microscope with a 100× objective using MetaMorph software. Images were analyzed using ImageJ (National Institutes of Health, Bethesda, Md.) and Adobe Photoshop® CS2.

Immunodetection of Proteins.

Cells were grown as described above (under Bacterial culture conditions). 200 μl of bacterial culture was collected by centrifugation and resuspended in 200 μl of 2× Laemmli Sample Buffer supplemented with 335 mM 2-mercaptoethanol. of the sample was separated by SDS-polyacrylamide gel electrophoresis and transferred to a nitrocellulose membrane using a Trans-Blot® SD Semi-Dry Transfer system (all from Bio Rad, Singapore). Primary antibodies (and dilutions) used were anti-GFP mouse monoclonal antibody (1:6000; Santa Cruz Biotechnology, Shanghai, China), anti-GroEL rabbit polyclonal antibody (1:6000; Sigma, Singapore), anti-RNA Polymerase β (Santa Cruz Biotechnology, Shanghai, China), and anti-β-Actin mouse monoclonal antibody (1:60000; Sigma, Singapore). The secondary antibodies were ECL™ Anti-rabbit IgG and ECL™ Anti-mouse IgG, both conjugated with Horseradish peroxidase (HRP) and used at a 1:10,000 dilution. Immunoblots were developed with Amersham ECL Prime (GE Healthcare, Singapore), and visualized in a ChemiDoc™ MP System (Bio-Rad, Singapore). Relative protein concentrations were determined by densitometry analysis using the measure function of ImageJ (National Institutes of Health, Bethesda, Md., USA).

SEC-MALLS Experiments.

sfGFP and vGFP proteins were analyzed with SEC-MALLS (size-exclusion chromatography with multi-angle laser light scattering) to verify the oligomeric state and size of the purified proteins. A Superdex 200 gel filtration column connected to an AKTA micro gel filtration system was equilibrated at 0.3 mL/min with TN buffer. 0.1 ml of protein sample at 5 mg/ml in TN buffer was then loaded, and the eluate was passed successively through a MiniDawn TREOS-angle light scattering detector (Wyatt, Santa Barbara, Calif., USA) coupled to an Optilab T-rEX refractive index monitor (Wyatt). Molecular masses were calculated using the AstraV software (Wyatt) using a dn/dc value of 0.18 ml/g.

Crystallography.

Crystals were grown over a reservoir containing 0.1M Sodium acetate at pH 4.6 with 30% (v/v) PEG 400 at 18° C. after combining 200 nL of 14 mg/mL protein solution in 20 mM Hepes pH 7.5, 150 mM NaCl with 200 nL of reservoir solution dispensed by a Phoenix HT crystallization robot into 96-well plates (CrystalQuick, 96 well, LBR, low profile (Greiner Bio-One 609871)). Crystals were harvested directly from 96-well plates, flash-frozen in liquid nitrogen and shipped to the Brookhaven National Laboratory for data collection at beamline X29 at the national synchrotron light source using a 1.075 A wavelength. A highly redundant dataset was collected and data were processed using HKL2000 (4). The structure was solved by molecular replacement using a poly-alanine model of a GFP antibody complex as search ensemble (PDB 3K1K) and the phaser/phenix AutoMRsoftware (5, 6). A single solution was found in space group P 41 21 2 comprising two antibody/GFP ensembles within the asymmetric unit. Five percent of the reflections were marked for cross-validation, the structure was refined using phenix.refine, and the model was built manually using coot (7). Coordinates are deposited in PDB under ID 4PFE. Pymol was used for atom distance measurements. vsfGFP-0 was aligned using the "super" command to chains A (GFP) and C (Enhancer) of PDB 3K1K. RMSD values are as reported by pymol for the given residues using the "rms" command.

Fluorescence Correlation Spectroscopy (FCS).

Theory.

FCS extracts information from fluorescence signal fluctuations as fluorophores pass through a small observation volume (around $10^{-15}$ L). This small observation volume is created by focusing a laser to a diffraction limited volume. Processes generating the fluctuations include chemical reactions, rotational diffusion, translational diffusion, or flow. The signals are then transformed to extract information embedded in the fluctuations by a temporal autocorrelation. The normalized autocorrelation function (ACF) can be written as:

$$G(\tau) = \frac{\langle F(t)F(t+\tau)\rangle}{\langle F(t)\rangle^2} \quad (1)$$

where F(t) is the fluorescence intensity at time t; < > denotes time average and τ is the lag time.

Assuming a Gaussian laser profile, the theoretical ACF for 3D free diffusion of one species with a single dark state is given by (8)):

$$G_{3D}(\tau) = \frac{1}{N}\left(1+\frac{\tau}{\tau_D}\right)^{-1}\left[1+\frac{1}{K^2}\left(\frac{\tau}{\tau_D}\right)\right]^{-1/2} f_{iso}(\tau) + G_\infty \quad (2)$$

where N is the average number of molecules in the observation volume; $\tau_D$ is the diffusion time the fluorophore taking to pass through the observation volume; $G_\infty$ is the convergence value of the ACF for long times with the expected value of 1;

$$K = \frac{\omega_z}{\omega_0} \quad (3)$$

where $\omega_0$ and $\omega_z$ are the radial and axial distances where the excitation intensity reaches $1/e^2$ of its value at the center of the observation volume and K describes the shape of the observation volume. $F_{iso}$ represents the fraction of particles in the single dark state and is calculated as:

$$F_{iso}(\tau) = \left(\frac{F_{iso}}{1-F_{iso}}\right)\exp\left(-\frac{\tau}{\tau_{iso}}\right) + 1 \quad (4)$$

where $\tau_{dark}$ is the relaxation time for this dark state. Typical dark states have kinetics occurring *on* a timescale that is much faster than the diffusion time (9, 10).

For a fluorophore, other fast blinking processes that are a reversible transition between a bright fluorescent state to a dark non-fluorescent state can also be expressed by this dark state dynamic and accounted in its ACF. It is known that low pH introduces an extra blinking process by the protonation and de-protonation equilibrium for EGFP (11). Therefore, the ACF under such circumstances should be revised as below to incorporate two dark states:

$$G_{3D}(\tau) = \frac{1}{N}\left(1 + \frac{\tau}{\tau_D}\right)^{-1}\left[1 + \frac{1}{K^2}\left(\frac{\tau}{\tau_D}\right)\right]^{-1/2} \times f_{iso}(\tau) \times f_{prot}(\tau) + G_\infty \quad (5)$$

Eq.2 was chosen to fit the experimental data for all green fluorescent proteins at pH from 6.5 to 10.5 and sfGFP data at pH 3.5 and 4.5, since the blinking induced by protonation is dominant. The free parameters for a fit are N, $\tau_D$, $\tau_{iso}$, $F_{iso}$ and $G_\infty$. Eq. 5 was chosen to fit data at pH from 3.5 to 5.5. The free parameters for a fit are N, $\tau_{iso}$, $F_{iso}$, $\tau_{prot}$, $F_{prot}$, and $G_\infty$. $\tau_D$ was fixed as the average value from high pHs.

From Eq. 2, the amplitude of the ACF is:

$$G(0) = \frac{1}{N}\left(\frac{1}{1-F_{iso}}\right) + G(\infty) \quad (6)$$

from where the average number of particles in the observation volume is given by:

$$N = \frac{1}{(G(0)-G(\infty))(1-F_{iso})} \quad (7)$$

and the average number of particles in singlet state in the observation volume is given by:

$$N_s = N(1-F_{iso}) = \frac{1}{(G(0)-G(\infty))} \quad (8)$$

The size of the observation volume $V_{eff}$ can be estimated from a calibration using a dye with known diffusion coefficient by the following equations:

$$\tau_D = \frac{\omega_0^2}{4D} \quad (9)$$

$$V_{eff} = \pi^{3/2}\omega_0^2\omega_z = K\pi^{3/2}\omega_0^3 \quad (10)$$

Then, the absolute concentration ($C_i$) of a sample and its diffusion coefficient (D) can be determined by Eq. 11 and 12:

$$C_i = \frac{N}{N_A V_{eff}} \quad (11)$$

$$D = \frac{\tau_{D0} \times D_0}{\tau_0} \quad (12)$$

where $\tau_{D0}$ and $D_0$ are the diffusion time and diffusion coefficient of the calibration dye.

The brightness ($\eta$) of a fluorescent protein is measured in thousands of photon counts per particle and second (kcps) and is defined as:

$$\eta = \frac{F_{mean}}{N} \quad (13)$$

The background stemming from detector noise or scattered light from the sample decreases the amplitude of the ACF, which leads to an overestimated N. From a sample with only a single fluorescent species, one can determine the brightness from the average fluorescent intensity, $F_{mean}$, and the apparent ACF amplitude, $G_{app}(0)=1/N_{app}$. For the calculation of the actual brightness, the ACF amplitude has to be corrected for the background ($\beta$), which can be determined from a blank measurement (12). The actual brightness should be corrected as:

$$\eta = \frac{F_{mean} - \beta}{N} \quad (14)$$

where N is the actual number of particles, and is given by:

$$1/N = \frac{\eta^2 N}{(\eta N)^2} \quad (15)$$

It is related to the apparent number of particles, $N_{app}$, by:

$$1/N_{app} = \frac{\eta^2 N}{(\eta N + \beta)^2} \quad (16)$$

From Eq. 12, the fluorescent intensity measured is given by:

$$F_{mean} = \eta N + \beta \quad (17)$$

Dividing (14) by (13) and using (15) we obtain $$N/N_{app} = \frac{\eta^2 N}{(\eta N + \beta)^2} \times \frac{(\eta N)^2}{\eta^2 N} = \frac{(\eta N)^2}{(\eta N + \beta)^2} = \frac{(F_{mean} - \beta)^2}{F_{mean}^2} \quad (18)$$

This can be rewritten as, $$N = \frac{N_{app} \times (F_{mean} - \beta)^2}{F_{mean}^2} \quad (19)$$

With N, the actual brightness η can be determined.

Instrument.

The FCS setup was described previously in detail (13). Briefly, FCS was performed using a customized Olympus FV 300 confocal microscope (Olympus, Tokyo, Japan). Excitation was provided by the 488 nm laser line of an Argon ion laser that is focused into samples by a water-immersion objective (60×, NA 1.2; Olympus, Tokyo, Japan). The laser power, measured before the objective, was 5-30 μW. The emitted light, which passed an internal 3× magnification stage in the confocal microscope, passed through a 150 μm pinhole. A 50/50 beam splitter (Thorlabs, Newton, N.J., USA) was used to split the emission light into two channels, to eliminate the afterpulsing effect of the detectors in FCS measurements (14). The light then was focused through band-pass filters 513/17-25 (Semrock, Rochester, N.Y., USA) onto avalanche-photodiode detectors (SPCM-AQR-14; Pacer, Berkshire, UK). Autocorrelation curves were computed online using a hardware correlator (Flex02-01D; Correlator.com, Bridgewater, N.J., USA).

Sample Preparation.

All stocks of fluorescent proteins were diluted in 1× TN buffer (50 mM Tris-HCl pH 7.4, 300 mM NaCl) to 10 nM (calculated based on UV absorption). For measurements at various pH values, pH of 1×TN buffer was adjusted using HCl or NaOH. All sample solutions mentioned below were placed on an 8 well chamber slide (Lab-Tek, New York, N.Y., USA) for measurement. The chamber was coated with BSA (Albumin from Bovine Serum, Sigma-Aldrich, Singapore) to avoid protein adhesion. BSA (1 g/100 L in 1× TN buffer) solution was placed in the chamber and then incubated at 4° C. for 24 h.

Calibration.

Calibration measurements were routinely performed before the measurement using Atto488 (D=400 μm²s⁻¹). A droplet of 60ℓ of 5 nM sample solution was used. The laser power before the objective was 30 μW. The estimated observation volume $V_{eff}$ was $6.60 \times 10^{-16}$ L. FCS data was fitted with Eq. 2; typical results of all fitting parameters are listed in Table 7. To calculate diffusion coefficients for the fluorescent proteins at different laser power, Atto488 was measured at 5, 10, 20 and 30 μW.

Background.

The background was measured using 300 μL 1×TN buffer. The laser power measured before the objective was 5, 10, 20 and 30 μW. The measured background consisted of both detector dark counts (220±2 Hz) and the light scattered from the solution. Both the total background and the background from solution were listed in Table 8. The background from solution increased proportionally to the laser power.

Experiments.

For all green fluorescent proteins, 300 μL of the sample solution was used. Laser power measured before the objective was 5, 10, 20 and 30 μW. Laser power applied for measurements at various pH values was 20 μW. The measuring time was 20 s. The measurements were performed at room temperature.

TABLE 3

Data processing and refinement statistics of vsfGFP-0 crystal structure.

| Data collection | vsfGFP-0 |
|---|---|
| Resolution range (Å) | 47.16-2.603 (2.696-2.603)* |
| Space group | P 41 21 2 |
| Unit cell | 83.426 83.426 228.691 90 90 90 |
| Unique reflections | 25661 (2495) |
| Multiplicity | 32.0 (28.9) |
| Completeness (%) | 99.95 (99.48) |
| Mean I/sigma(I) | 20.97 (3.90) |
| Wilson B-factor | 59.47 |
| R-merge | 11.2 (60.3) |
| R-work | 0.1985 (0.2900) |
| R-free | 0.2553 (0.4025) |
| Number of atoms | 5555 |
| macromolecules | 5370 |
| ligands | 44 |
| water | 141 |
| Protein residues | 684 |
| RMS(bonds) | 0.008 |
| RMS(angles) | 0.99 |
| Ramachandran favored (%) | 98 |
| Ramachandran outliers (%) | 0 |
| Clashscore | 5.73 |
| Average B-factor | 53.00 |
| macromolecules | 53.40 |
| ligands | 45.20 |
| solvent | 39.40 |

*Values in parentheses for highest resolution shell

TABLE 4

FCS measurements of different types of green fluorescent proteins

| Fluorescent Protein | pH | $\tau_D$ (μs) | Brightness (kcps) | $\tau_{iso}$ (μs) | $F_{iso}$ (%) | $\tau_{prot}$ (μs) | $F_{prot}$ (%) |
|---|---|---|---|---|---|---|---|
| sfGFP | 3.5 | 140 | 0.46 ± 0.05 | — | — | 76 ± 5 | 92 ± 1 |
|  | 4.5 | 140 | 1.51 ± 0.21 | — | — | 230 ± 147 | 84 ± 2 |
|  | 5.5 | 140 | 5.69 ± 0.54 | 11 ± 11 | 20 ± 4 | 506 ± 132 | 52 ± 4 |
|  | 6.5 | 127 ± 6 | 11.46 ± 0.26 | 6 ± 5 | 20 ± 8 | — | — |
|  | 7.5 | 132 ± 4 | 12.52 ± 0.20 | 7 ± 2 | 18 ± 4 | — | — |
|  | 8.5 | 142 ± 11 | 11.98 ± 0.46 | 11 ± 12 | 19 ± 5 | — | — |
|  | 9.5 | 146 ± 9 | 10.34 ± 0.36 | 12 ± 11 | 22 ± 8 | — | — |
|  | 10.5 | 151 ± 11 | 9.74 ± 0.33 | 14 ± 9 | 16 ± 5 | — | — |
| vsfGFP-9 | 3.5 | 136 | 3.39 ± 0.57 | 5 ± 2 | 23 ± 4 | 753 ± 91 | 71 ± 4 |
|  | 4.5 | 136 | 7.92 ± 2.13 | 7 ± 2 | 17 ± 3 | 1158 ± 696 | 38 ± 16 |
|  | 5.5 | 136 | 10.05 ± 1.40 | 10 ± 5 | 16 ± 1 | 2361 ± 739 | 32 ± 11 |
|  | 6.5 | 131 ± 3 | 14.97 ± 0.13 | 8 ± 4 | 18 ± 3 | — | — |
|  | 7.5 | 132 ± 5 | 14.91 ± 0.12 | 7 ± 1 | 18 ± 3 | — | — |
|  | 8.5 | 133 ± 7 | 14.72 ± 0.30 | 8 ± 3 | 17 ± 3 | — | — |
|  | 9.5 | 146 ± 14 | 12.72 ± 0.43 | 11 ± 6 | 16 ± 2 | — | — |
|  | 10.5 | 138 ± 7 | 11.84 ± 0.24 | 12 ± 6 | 16 ± 3 | — | — |

TABLE 4-continued

FCS measurements of different types of green fluorescent proteins

| Fluorescent Protein | pH | $\tau_D$ (μs) | Brightness (kcps) | $\tau_{iso}$ (μs) | $F_{iso}$ (%) | $\tau_{prot}$ (μs) | $F_{prot}$ (%) |
|---|---|---|---|---|---|---|---|
| vsfGFP-0 | 3.5 | 204 | 5.11 ± 0.74 | 23 ± 9 | 13 ± 3 | 1327 ± 216 | 58 ± 6 |
|  | 4.5 | 204 | 11.93 ± 1.50 | 13 ± 4 | 13 ± 1 | 1155 ± 536 | 24 ± 10 |
|  | 5.5 | 204 | 16.16 ± 1.87 | 9 ± 5 | 14 ± 2 | 2098 ± 1659 | 24 ± 9 |
|  | 6.5 | 193 ± 7 | 22.83 ± 0.20 | 6 ± 3 | 13 ± 3 | — | — |
|  | 7.5 | 202 ± 7 | 24.04 ± 0.25 | 9 ± 4 | 11 ± 2 | — | — |
|  | 8.5 | 203 ± 8 | 23.57 ± 0.36 | 9 ± 3 | 12 ± 3 | — | — |
|  | 9.5 | 216 ± 18 | 20.39 ± 0.72 | 22 ± 23 | 12 ± 3 | — | — |
|  | 10.5 | 207 ± 8 | 20.19 ± 0.35 | 12 ± 9 | 12 ± 2 | — | — |

TABLE 5

Plasmids used in this work.

| Plasmid | Description | Relevant information |
|---|---|---|
| pBAD33 | Plasmid carrying arabinose-inducible promoter | Guzman et al. 1995 *JBact* 177(14): 4121-30 |
| pSLC-114 | pUC19-sfGFP | Mike Caparon Lab, Washington University in St. Louis |
| pSLC-151 | pBAD-vsfGFP-2 | This study |
| pSLC-152 | pBAD-vsfGFP-4 | This study |
| pSLC-153 | pBAD-vsfGFP-6 | This study |
| pSLC-209 | pTetO-FUW | Addgene plasmid 20724 |
| pSLC-210 | pFUW-M2rtTA | Addgene plasmid 20342 |
| pSLC-252 | pBAD-Enhancer | This study |
| pSLC-253 | pBAD-sfGFP | This study |
| pSLC-254 | pBAD-vsfGFP-0 | This study |
| pSLC-255 | pBAD-vsfGFP-9 | This study |
| pSLC-256 | pBAD-perisfGFP | This study |
| pSLC-257 | pBAD-perivsfGFP-0 | This study |
| pSLC-258 | pBAD-perivsfGFP-9 | This study |
| pSLC-259 | pBAD-EGFP | This study |
| pSLC-260 | pBAD-vEGFP | This study |
| pSLC-261 | pBAD-periEGFP | This study |
| pSLC-262 | pBAD-perivEGFP | This study |
| pSLC-263 | pTetO-FUW-sfGFP | This study |
| pSLC-264 | pTetO-FUW-vsfGFP-0 | This study |
| pSLC-265 | pTetO-FUW-vsfGFP-9 | This study |
| pSLC-266 | pBAD-CK8 | This study |
| pSLC-267 | pBAD-CK8-sfGFP | This study |
| pSLC-268 | pBAD-CK8-vsfGFP-0 | This study |
| pSLC-269 | pBAD-CK8-vsfGFP-9 | This study |
| pEGFP-C1 | Expression plasmid for EGFP | Clontech |

TABLE 6

Primer sequences used in this study.

| Primer name | Nucleotide sequence (5' to 3') | Description | SEQ ID NO: |
|---|---|---|---|
| P1 | TCTAGAATAATTTTGTTTAACTTTAAGAAGG AGATATACATATGAGCAAAGGAGAAGAAC TTTTCACTGGA | sfGFP and vsfGFP constructs | 22 |
| P2 | AAGCTTTTAATGATGATGATGATGTTT GTAGAGCTCATCCAT | sfGFP construct | 23 |
| P3 | AAGCTTTTAATGATGATGATGATGGGA AACGGTAACTTGCGTACCCTG | vsfGFP constructs | 24 |
| P4 | TTGTAACTGCTGCTGGGATTGCCCAGGTGC AGTTGGTCGA | vsfGFP-0 construct | 25 |
| P5 | TCGACCAACTGCACCTGGGCAATCCCAGCA GCAGTTACAA | vsfGFP-0 construct | 26 |
| P6 | CTGCTGCTGGGATTACACATGCCCAGGTGC AGTTGGTCGA | vsfGFP-2 construct | 27 |
| P7 | TCGACCAACTGCACCTGGGCATGTGTAATC CCAGCAGCAG' | vsfGFP-2 construct | 28 |
| P8 | CTGGGATTACACATGGCATGGCCCAGGTGC AGTTGGTCGA | vsfGFP-4 construct | 29 |
| P9 | TCGACCAACTGCACCTGGGCCATGCCATGT GTAATCCCAG | vsfGFP-4 construct | 30 |
| P10 | TTACACATGGCATGGATGAGGCCCAGGTGC AGTTGGTCGA | vsfGFP-6 construct | 31 |

TABLE 6-continued

Primer sequences used in this study.

| Primer name | Nucleotide sequence (5' to 3') | Description | SEQ ID NO: |
|---|---|---|---|
| P11 | TCGACCAACTGCACCTGGGCCTCATCCATG CCATGTGTAA | vsfGFP-6 construct | 32 |
| P12 | GCATGGATGAGCTCTACAAAGCCCAGGTGC AGTTGGTCGA | vsfGFP-9 construct | 33 |
| P13 | TCGACCAACTGCACCTGGGCTTTGTAGAGC TCATCCATGC | vsfGFP-9 construct | 34 |
| P14 | TCTAGAATAATTTTGTTTAACTTTAAGAAGG AGATATAATGAAAAAGACAGCAATCGCCA | periplasmic signal sequence | 35 |
| P15 | CATATGTGCACCGCCAGATTCGACCAACT | periplasmic signal sequence | 36 |
| P16 | TCTAGAATAATTTTGTTTAACTTTAAGAAG GAGATATACATATGGTGAGCAAGGGCGAG GAG | EGFP and vEGFP constructs | 37 |
| P17 | AAGCTTTTAATGATGATGATGATGATGCTT GTACAGCTCGTCCATG | EGFP and vEGFP constructs | 38 |
| P18 | TTCGACCAACTGCACCTGGGCCTTGTACAG CTCGTCCATG | vEGFP constructs | 39 |
| P19 | CATGGACGAGCTGTACAAG GCCCAGGTGCAGTTGGTCGAA | vEGFP constructs | 40 |
| P20 | AAGCTTTTAATGATGATGATGATGATGGGA AACGGTAACTTGCGTACCCTG | vEGFP constructs | 41 |
| P21 | GAATTCGCCACCATGAGCAAAGGAGAAGA AC | TetO-FUW construct | 42 |
| P22 | GAATTCTTAATGATGATGATGATGATG | TetO-FUW construct | 43 |
| P23 | TCTAGAATAATTTTGTTTAACTTTAAGAAGG AGATATACATATGGCGCAAGTT CAGCTGCAAGAG | CK8_vsfGFP constructs | 44 |
| P24 | AAGCTTTTAATGATGATGATGATGATG | CK8_vsfGFP constructs | 45 |
| P25 | TCCAGTGAAAAGTTCTTCTCCTTTGCTGCCG CTGCCGCTACCGGAA | CK8_vsfGFP constructs | 46 |
| P26 | TTCCGGTAGCGGCAGCGGCAGCAAAGGAG AAGAACTTTTCACTGGA | CK8_vsfGFP constructs | 47 |

TABLE 7

Typical values of fitting parameters for calibration using Atto488

| Fitting Parameters | Fitting Value |
|---|---|
| N | 2.23 ± 0.05 |
| $\tau_D$ (µs) | 45 ± 1 |
| $\tau_{iso}$ (µs) | 6 ± 2 |
| $F_{iso}$ (%) | 17 ± 2 |
| K | 5.51 ± 0.70 |
| $G(\infty)$ | 0.9999 ± 0.0001 |

Data = mean ± s.d.

TABLE 8

Background measurement at different laser power

| Laser Power (µW) | Total Background | Background from Solution |
|---|---|---|
| | Photon Counts per second (Hz) | |
| 5 | 238 ± 2 | 18 ± 2 |
| 10 | 256 ± 5 | 36 ± 5 |
| 20 | 288 ± 4 | 68 ± 4 |
| 30 | 329 ± 13 | 109 ± 13 |

Data = mean ± s.d.

REFERENCES

1. Kirchhofer A, et al. (2009) Modulation of protein properties in living cells using nanobodies. *Nature structural & molecular biology* 17(1):133-138.
2. Rothbauer U, et al. (2006) Targeting and tracing antigens in live cells with fluorescent nanobodies. (Translated from eng) *Nat Methods* 3(11):887-889 (in eng).
3. Villalobos A, Ness J E, Gustafsson C, Minshull J, & Govindarajan S (2006) Gene Designer: a synthetic biology tool for constructing artificial DNA segments. (Translated from eng) *BMC bioinformatics* 7:285 (in eng).
4. Otwinowski Z & Minor W (1997) Processing of X-ray Diffraction Data Collected in Oscillation Mode. in *Macromolecular Crystallography, part A*, eds Carter C W J & Sweet R M (Academic Press, New York), pp 307-326.
5. Adams P D, et al. (2004) Recent developments in the PHENIX software for automated crystallographic structure determination. (Translated from eng) *J Synchrotron Radiat* 11(Pt 1):53-55 (in eng).
6. McCoy A J, Grosse-Kunstleve R W, Storoni L C, & Read R J (2005) Likelihood-enhanced fast translation functions. (Translated from eng) *Acta Crystallogr D Biol Crystallogr* 61(Pt 4):458-464 (in eng).
7. Emsley P & Cowtan K (2004) Coot: model-building tools for molecular graphics. (Translated from eng) *Acta Crystallogr D Biol Crystallogr* 60(Pt 12 Pt 1):2126-2132 (in eng).
8. Aragon S & Pecora R (2008) Fluorescence correlation spectroscopy as a probe of molecular dynamics. *The Journal of Chemical Physics* 64(4):1791-1803.
9. Widengren J, Mets U, & Rigler R (1995) Fluorescence correlation spectroscopy of triplet states in solution: a theoretical and experimental study. *The Journal of Physical Chemistry* 99(36):13368-13379.
10. Widengren J, Mets U, & Rigler R (1999) Photodynamic properties of green fluorescent proteins investigated by fluorescence correlation spectroscopy. *Chemical Physics* 250(2):171-186.
11. Haupts U, Maiti S, Schwille P, & Webb W W (1998) Dynamics of fluorescence fluctuations in green fluorescent protein observed by fluorescence correlation spectroscopy. *Proceedings of the National Academy of Sciences* 95(23):13573-13578.
12. Koppel D E (1974) Statistical accuracy in fluorescence correlation spectroscopy. *Physical Review A* 10(6):1938-1945.
13. Pan X, et al. (2007) Multifunctional fluorescence correlation microscope for intracellular and microfluidic measurements. *Review of scientific instruments* 78(5): 053711.
14. Zhao M, et al. (2003) Afterpulsing and its correction in fluorescence correlation spectroscopy experiments. *Applied optics* 42(19):4031-4036.

INDUSTRIAL APPLICABILITY

The compositions described herein can be useful in the following industrial applications: High sensitivity reporter gene for promoter and protein analysis (including but not limited to expression screens, protein localization and interaction studies using light and electron microscopy and histology, and cell marking/identification assays); Genetic labeling of nanobodies with fluorescent tags for brighter and more easily produced molecular probes; Controlled dimerization and multimerization of proteins including enzymes (which may improve efficiency), binding proteins (which may improve avidity and enable sensing and purification applications), and any other molecule that can be bound by a nanobody.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, issued patents, and patent applications cited herein are hereby incorporated by reference in their entirety for, all purposes.

---

What is claimed is:

1. A fluorescent fusion protein comprising:
   a fluorescent protein;
   a single domain antibody that binds to the fluorescent protein; and
   a linker linking the C-terminal of the fluorescent protein to the N-terminal of the single domain antibody.

2. The fluorescent fusion protein of claim 1, wherein the fluorescent protein is a green fluorescent protein (GFP) or variant thereof.

3. The fluorescent fusion protein of claim 2, wherein the GFP is selected from wild-type GFP (SEQ ID NO:11), super-folder GFP (sfGFP) (SEQ ID NO:6), cyan fluorescent protein (CFP) (SEQ ID NO:18), sfCFP (SEQ ID NO:4), yellow fluorescent protein (YFP) (SEQ ID NO:16), or sfYFP (SEQ ID NO:8).

4. The fluorescent fusion protein of claim 2, wherein the GFP is at least 90% identical to SEQ ID NOs: 11, 6, 18, 4, 16, or 8.

5. The fluorescent fusion protein of claim 1, wherein the linker comprises 0 to 9 amino acids.

6. The fluorescent fusion protein of claim 1, wherein the fluorescent fusion protein converts between a monomeric complex and dimeric complex by varying the linker length.

7. The fluorescent fusion protein of claim 5, wherein the linker comprises 9 amino acids, and the fusion protein has a single particle brightness about 1.3 times greater than the single particle brightness of GFP alone under identical excitation conditions.

8. The fluorescent fusion protein of claim 5, where the linker comprises 0 amino acids, and the fusion protein has a single particle brightness about 2.5 times greater than the single particle brightness of GFP alone under identical excitation conditions.

9. The fluorescent fusion protein of claim 7, where the fluorescence is increased about 7-fold compared to GFP or sfGFP alone at a pH of 3.5.

10. The fluorescent fusion protein of claim 8, where the fluorescence is increased about 7-fold compared to GFP or sfGFP alone at a pH of 3.5.

11. The fluorescent fusion protein of claim 1, where the single domain antibody is a single chain $V_HH$ nanobody.

12. The fluorescent fusion protein of claim 9, where the nanobody comprises an amino acid sequence at least 90% identical to SEQ ID NO:1.

13. A nucleic acid molecule comprising a nucleic acid sequence encoding the fluorescent fusion protein of claim 1.

14. An expression cassette comprising the nucleic acid molecule of claim 13.

15. A cell comprising the fluorescent fusion protein of claim 1, wherein the cell is selected from a bacterial cell, a eukaryotic cell, or a mammalian cell.

16. A method for producing a fusion protein comprising a fluorescent protein and a single domain antibody that binds to the fluorescent protein, the method comprising fusing the single domain antibody to the fluorescent protein via a linker.

17. The method of claim 16, where the C-terminus of the fluorescent protein is linked to the N-terminus of the single domain antibody.

18. The method of claim 16, wherein the linker comprises 0 to 9 amino acids, and the length of the linker determines an oligomeric structure of the fusion protein.

19. The method of claim 18, wherein the fusion protein is a dimer and comprises a linker of zero, one, two, or three amino acids.

20. The method of claim 18, wherein the fusion protein is a monomer and comprises a linker of four, five, six, seven, eight, or nine amino acids.

21. The method of claim 16, wherein the fluorescent protein is GFP or a variant thereof.

22. A method for expressing a fluorescent fusion protein in the periplasm of a bacterial cell, comprising: transfecting the expression cassette of claim 14 into a bacterial cell, and expressing the fusion protein encoded by the expression cassette in the periplasm.

23. The fluorescent fusion protein of claim 6, wherein the dimer comprises two GFP polypeptides and two single domain antibody polypeptides.

* * * * *

SEQUENCE LISTING

```
<160> NUMBER OF SEQ ID NOS: 47

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
```

```
              85                  90                  95
Tyr Cys Asn Val Asn Val Gly Phe Glu Tyr Trp Gly Gln Gly Thr Gln
            100                 105                 110

Val Thr Val Ser
        115

<210> SEQ ID NO 2
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggcccagg tgcagttggt cgaatctggc ggtgccctgg ttcaaccggg tggtagcctg      60
cgtctgtcct gtgcggcgtc tggcttccca gttaatcgtt atagcatgcg ttggtaccgt     120
caagcgcctg gcaaggagcg tgagtgggtc gcgggtatga gctcggcggg tgatcgtagc     180
agctacgaag attccgttaa aggccgcttt accatcagcc gtgacgatgc gcgcaatacc     240
gtatacctgc aaatgaacag cctgaagccg aggacaccg cagtctatta ctgcaatgtt      300
aatgtgggtt ttgaatactg gggccagggt acgcaagtta ccgtttccta a              351

<210> SEQ ID NO 3
<211> LENGTH: 717
<212> TYPE: DNA
<213> ORGANISM: Artificial Sequence
<220> FEATURE:
<223> OTHER INFORMATION: Description of Artificial Sequence: Synthetic
      sfCFP polynucleotide

<400> SEQUENCE: 3
atgagcaaag gagaagaact tttcactgga gttgtcccaa ttcttgttga attagatggt      60
gatgttaatg ggcacaaatt ttctgtccgt ggagagggtg aaggtgatgc tacaaacgga     120
aaactcaccc ttaaatttat ttgcactact ggaaaactac ctgttccgtg ccaacacttt     180
gtcactactc tgacctgggg tgttcaatgc ttttcccgtt atccggatca catgaaacgg     240
catgactttt tcaagagtgc catgcccgaa ggttatgtac aggaacgcac tatatctttc     300
aaagatgacg ggacctacaa gacgcgtgct gaagtcaagt ttgaaggtga tacccttgtt     360
aatcgtatcg agttaaaggg tattgatttt aagaagatg gaaacattct tggacacaaa      420
ctcgagtaca actttaactc acacaatgta tacatcacgg cagacaaaca aaagaatgga     480
atcaaagcta acttcaaaat tcgccacaac gttgaagatg gttccgttca actagcagac     540
cattatcaac aaaatactcc aattggcgat ggccctgtcc ttttaccaga caaccattac     600
ctgtcgacac aatctgtcct ttcgaaagat cccaacgaaa agcgtgacca catggtcctt     660
cttgagtttg taactgctgc tgggattaca catggcatgg atgagctcta caaataa        717

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      sfCFP polypeptide

<400> SEQUENCE: 4

Met Ser Lys Gly Glu Glu Leu Phe Thr Gly Val Val Pro Ile Leu Val
1               5                   10                  15
```

Glu Leu Asp Gly Asp Val Asn Gly His Lys Phe Ser Val Arg Gly Glu
          20                  25                  30

Gly Glu Gly Asp Ala Thr Asn Gly Lys Leu Thr Leu Lys Phe Ile Cys
         35                  40                  45

Thr Thr Gly Lys Leu Pro Val Pro Trp Pro Thr Leu Val Thr Thr Leu
 50                  55                  60

Thr Trp Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
             85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 717
<212> TYPE: DNA
<213> ORGANISM: Artificial Sequence
<220> FEATURE:
<223> OTHER INFORMATION: Description of Artificial Sequence: Synthetic
      sfGFP polynucleotide

<400> SEQUENCE: 5
atgagcaaag gagaagaact tttcactgga gttgtcccaa ttcttgttga attagatggt     60
gatgttaatg ggcacaaatt ttctgtccgt ggagagggtg aaggtgatgc tacaaacgga    120
aaactcaccc ttaaatttat ttgcactact ggaaaactac ctgttccgtg gccaacactt    180
gtcactactc tgacctatgg tgttcaatgc ttttcccgtt atccggatca catgaaacgg    240
catgactttt tcaagagtgc catgcccgaa ggttatgtac aggaacgcac tatatctttc    300
aaagatgacg gaacctacaa gacgcgtgct gaagtcaagt ttgaaggtga taccttgtt     360 aatcgtatcg agttaaaggg tattgatttt aagaagatg gaaacattct ggacacaaa     420 ctcgagtaca actttaactc acacaatgta tacatcacgg cagacaaaca aagaatgga    480 atcaaagcta acttcaaaat tcgccacaac gttgaagatg gttccgttca actagcagac    540
cattatcaac aaaatactcc aattggcgat ggccctgtcc ttttaccaga caaccattac    600
ctgtcgacac aatctgtcct ttcgaaagat cccaacgaaa agcgtgacca catggtcctt    660
cttgagtttg taactgctgc tgggattaca catggcatgg atgagctcta caaataa      717

<210> SEQ ID NO 6
<211> LENGTH: 238
<212> TYPE: PRT
<213> ORGANISM: Artificial Sequence
<220> FEATURE:
<223> OTHER INFORMATION: Description of Artificial Sequence: Synthetic sfGFP polypeptide

<400> SEQUENCE: 6

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 7
<211> LENGTH: 717
<212> TYPE: DNA
<213> ORGANISM: Artificial Sequence
<220> FEATURE:
<223> OTHER INFORMATION: Description of Artificial Sequence: Synthetic sfYFP polynucleotide

<400> SEQUENCE: 7

```
atgagcaaag gagaagaact tttcactgga gttgtcccaa ttcttgttga attagatggt      60
gatgttaatg ggcacaaatt ttctgtccgt ggagagggtg aaggtgatgc tacaaacgga     120
aaactcaccc ttaaatttat ttgcactact ggaaaactac ctgttccgtg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggacctacaa gacgcgtgct gaagtcaagt ttgaaggtga tacccttgtt     360
aatcgtatcg agttaaaggg tattgatttt aaagaagatg gaaacattct tggacacaaa     420
```

```
ctcgagtaca actttaactc acacaatgta tacatcacgg cagacaaaca aaagaatgga      480
atcaaagcta acttcaaaat tcgccacaac gttgaagatg gttccgttca actagcagac      540
cattatcaac aaaatactcc aattggcgat ggccctgtcc ttttaccaga caaccattac      600
ctgtcgtatc aatctgtcct ttcgaaagat cccaacgaaa agcgtgacca catggtcctt      660
cttgagtttg taactgctgc tgggattaca catggcatgg atgagctcta caaataa         717
```

<210> SEQ ID NO 8
<211> LENGTH: 238
<212> TYPE: PRT
<213> ORGANISM: Artificial Sequence
<220> FEATURE:
<223> OTHER INFORMATION: Description of Artificial Sequence: Synthetic
      sfYFP polypeptide

<400> SEQUENCE: 8

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 9

```
acacatggca tggatgagct ctacaaa                                           27
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 10

Thr His Gly Met Asp Glu Leu Tyr Lys
1               5

<210> SEQ ID NO 11
<211> LENGTH: 238
<212> TYPE: PRT
<213> ORGANISM: Unknown
<220> FEATURE:
<223> OTHER INFORMATION: Description of Unknown: wtGFP
      polypeptide

<400> SEQUENCE: 11

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 12
<211> LENGTH: 717
<212> TYPE: DNA
<213> ORGANISM: Unknown
<220> FEATURE:
<223> OTHER INFORMATION: Description of Unknown: wtGFP
      polynucleotide

<400> SEQUENCE: 12

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcaagat acccagatca tatgaaacag     240
catgactttt tcaagagtgc catgcccgaa ggttatgtac aggaaagaac tatattttc      300
aaagatgacg ggaactacaa gacacgtgct gaagtcaagt ttgaaggtga tacccttgtt     360
aatagaatcg agttaaaagg tattgatttt aaagaagatg gaaacattct tggacacaaa     420
ttggaataca actataactc acacaatgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
ctgtccacac aatctgccct ttcgaaagat cccaacgaaa agagagacca catggtcctt     660
cttgagtttg taacagctgc tgggattaca catggcatgg atgaactata caaatag        717
```

<210> SEQ ID NO 13
<211> LENGTH: 720
<212> TYPE: DNA
<213> ORGANISM: Artificial Sequence
<220> FEATURE:
<223> OTHER INFORMATION: Description of Artificial Sequence: Synthetic
      EGFP polynucleotide

<400> SEQUENCE: 13

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 14
<211> LENGTH: 239
<212> TYPE: PRT
<213> ORGANISM: Artificial Sequence
<220> FEATURE:
<223> OTHER INFORMATION: Description of Artificial Sequence: Synthetic
      EGFP polypeptide

<400> SEQUENCE: 14

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30
```

-continued

```
Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 15
<211> LENGTH: 720
<212> TYPE: DNA
<213> ORGANISM: Artificial Sequence
<220> FEATURE:
<223> OTHER INFORMATION: Description of Artificial Sequence: Synthetic
      EYFP polynucleotide

<400> SEQUENCE: 15

| | | | | | | |
|---|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccctgaccta | cggcgtgcag | tgcttcagcc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaagtaa | 720 |

<210> SEQ ID NO 16
<211> LENGTH: 239
<212> TYPE: PRT
<213> ORGANISM: Artificial Sequence

```
<220> FEATURE:
<223> OTHER INFORMATION: Description of Artificial Sequence: Synthetic
      EYFP polypeptide

<400> SEQUENCE: 16

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 17
<211> LENGTH: 720
<212> TYPE: DNA
<213> ORGANISM: Artificial Sequence
<220> FEATURE:
<223> OTHER INFORMATION: Description of Artificial Sequence: Synthetic
      ECFP polynucleotide

<400> SEQUENCE: 17
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccct gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagaccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 18
<211> LENGTH: 239
<212> TYPE: PRT
<213> ORGANISM: Artificial Sequence
<220> FEATURE:
<223> OTHER INFORMATION: Description of Artificial Sequence: Synthetic
      ECFP polypeptide

<400> SEQUENCE: 18

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 19
<211> LENGTH: 495
<212> TYPE: DNA
<213> ORGANISM: Artificial Sequence
<220> FEATURE:
<223> OTHER INFORMATION: Description of Artificial Sequence: Synthetic
      cytokeratin-8 nanobody polynucleotide

<400> SEQUENCE: 19

```
atgaagaaaa ccgctatcgc aattgccgtc gcactggccg gcttcgccac cgtcgcacag    60
gcgcaccacc accatcacca tgcgcaagtt cagctgcaag agagcggtgg tggcttggtt    120
caagctggcg gtagcctgac gctgagctgc acctatagcg gcctgacgtt cgatgactac    180
```

```
aatatgggct ggttccgcca gggtccgggt aaggaacgtg agcgtgtgag cgcgatcagc    240
tttcgtggta ttacctacta tgtggactcc gtcaaaggtc gcttcactat cagccgtgac    300
aatgcgaaga aaacgctgta cttgcaaatg aacggcctga ccccggatga taccgcgacg    360
tattactgtg cgggttctcg ctttctgagc ccgtttgttc gtgacggtga caccaaactg    420
attaacgatt ggggccaggg tacccaggtt acggtgagca gctcgggttc tggttccggt    480
agcggcagcg gctaa                                                    495
```

<210> SEQ ID NO 20
<211> LENGTH: 164
<212> TYPE: PRT
<213> ORGANISM: Artificial Sequence
<220> FEATURE:
<223> OTHER INFORMATION: Description of Artificial Sequence: Synthetic
    cytokeratin-8 nanobody polypeptide

<400> SEQUENCE: 20

```
Met Lys Lys Thr Ala Ile Ala Ile Ala Val Ala Leu Ala Gly Phe Ala
1               5                   10                  15

Thr Val Ala Gln Ala His His His His His His Ala Gln Val Gln Leu
            20                  25                  30

Gln Glu Ser Gly Gly Gly Leu Val Gln Ala Gly Gly Ser Leu Thr Leu
        35                  40                  45

Ser Cys Thr Tyr Ser Gly Leu Thr Phe Asp Asp Tyr Asn Met Gly Trp
    50                  55                  60

Phe Arg Gln Gly Pro Gly Lys Glu Arg Glu Arg Val Ser Ala Ile Ser
65                  70                  75                  80

Phe Arg Gly Ile Thr Tyr Tyr Val Asp Ser Val Lys Gly Arg Phe Thr
                85                  90                  95

Ile Ser Arg Asp Asn Ala Lys Lys Thr Leu Tyr Leu Gln Met Asn Gly
            100                 105                 110

Leu Thr Pro Asp Asp Thr Ala Thr Tyr Tyr Cys Ala Gly Ser Arg Phe
        115                 120                 125

Leu Ser Pro Phe Val Arg Asp Gly Asp Thr Lys Leu Ile Asn Asp Trp
    130                 135                 140

Gly Gln Gly Thr Gln Val Thr Val Ser Ser Ser Gly Ser Gly Ser Gly
145                 150                 155                 160

Ser Gly Ser Gly
```

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 21

```
Ser Gly Ser Gly Ser Gly Ser Gly Ser Gly
1               5                   10
```

<210> SEQ ID NO 22
<211> LENGTH: 71
<212> TYPE: DNA
<213> ORGANISM: Artificial Sequence
<220> FEATURE:
<223> OTHER INFORMATION: Description of Artificial Sequence: Synthetic
    primer -continued

<400> SEQUENCE: 22
tctagaataa ttttgtttaa ctttaagaag gagatataca tatgagcaaa ggagaagaac    60
ttttcactgg a    71

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagcttttaa tgatgatgat gatgatgttt gtagagctca tccat    45

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagcttttaa tgatgatgat gatgatggga acggtaact tgcgtaccct g    51

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgtaactgc tgctgggatt gcccaggtgc agttggtcga    40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgaccaact gcacctgggc aatcccagca gcagttacaa    40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgctgctgg gattacacat gcccaggtgc agttggtcga    40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 28
tcgaccaact gcacctgggc atgtgtaatc ccagcagcag                    40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgggattac acatggcatg gcccaggtgc agttggtcga                    40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcgaccaact gcacctgggc catgccatgt gtaatcccag                    40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttacacatgg catggatgag gcccaggtgc agttggtcga                    40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcgaccaact gcacctgggc ctcatccatg ccatgtgtaa                    40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcatggatga gctctacaaa gcccaggtgc agttggtcga                    40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 34
tcgaccaact gcacctgggc tttgtagagc tcatccatgc                                40

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctagaataa ttttgtttaa ctttaagaag gagatataat gaaaaagaca gcaatcgcca          60

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
catatgtgca ccgccagatt cgaccaact                                           29

<210> SEQ ID NO 37
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tctagaataa ttttgtttaa ctttaagaag gagatataca tatggtgagc aagggcgagg          60
ag                                                                         62

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aagcttttaa tgatgatgat gatgatgctt gtacagctcg tccatg                        46

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttcgaccaac tgcacctggg ccttgtacag ctcgtccatg                               40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 40
catggacgag ctgtacaagg cccaggtgca gttggtcgaa                    40

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aagcttttaa tgatgatgat gatgatggga acggtaact tgcgtaccct g        51

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaattcgcca ccatgagcaa aggagaagaa c                             31

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaattcttaa tgatgatgat gatgatg                                  27

<210> SEQ ID NO 44
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctagaataa ttttgtttaa ctttaagaag gagatataca tatggcgcaa gttcagctgc  60
aagag                                                             65

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aagcttttaa tgatgatgat gatgatg                                  27

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic

```
        primer

<400> SEQUENCE: 46
tccagtgaaa agttcttctc ctttgctgcc gctgccgcta ccggaa            46

<210> SEQ ID NO 47
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttccggtagc ggcagcggca gcaaaggaga gaactttc actgga              46
```